US012698264B2

(12) United States Patent
Wender et al.

(10) Patent No.: US 12,698,264 B2
(45) Date of Patent: Aug. 4, 2026

(54) SYNTHESIS OF TIGILANOL TIGLATE AND ANALOGS THEREOF

(71) Applicant: THE BOARD OF TRUSTEES OF THE LELAND STANFORD JUNIOR UNIVERSITY, Stanford, CA (US)

(72) Inventors: Paul A. Wender, Menlo Park, CA (US); Nguyen Hong Quang Luu, Menlo Park, CA (US); Zachary Gentry, Palo Alto, CA (US); Edward Njoo, Freemont, CA (US); David Fanelli, Stanford, CA (US); Owen Dennis McAteer, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 304 days.

(21) Appl. No.: 18/264,939

(22) PCT Filed: Mar. 10, 2022

(86) PCT No.: PCT/US2022/019718
§ 371 (c)(1),
(2) Date: Aug. 10, 2023

(87) PCT Pub. No.: WO2022/192521
PCT Pub. Date: Sep. 15, 2022

(65) Prior Publication Data

US 2024/0132460 A1 Apr. 25, 2024

Related U.S. Application Data

(60) Provisional application No. 63/159,163, filed on Mar. 10, 2021.

(51) Int. Cl.

| | |
|---|---|
| ***C07D 303/14*** | (2006.01) |
| ***A61K 31/122*** | (2006.01) |
| ***A61K 36/47*** | (2006.01) |

(52) U.S. Cl.
CPC .......... *C07D 303/14* (2013.01); *A61K 31/122* (2013.01); *A61K 36/47* (2013.01); *A61K 2236/15* (2013.01); *A61K 2236/33* (2013.01); *A61K 2236/53* (2013.01)

(58) Field of Classification Search
CPC .................................................... C07D 303/14
USPC .......................................................... 549/523
See application file for complete search history.

(56) References Cited

U.S. PATENT DOCUMENTS

| | | | |
|---|---|---|---|
| 9,770,431 | B2 | 9/2017 | Reddell et al. |
| 10,183,921 | B2 | 1/2019 | Reddell et al. |
| 2016/0158187 | A1 | 6/2016 | Reddell et al. |
| 2016/0280627 | A1 | 9/2016 | Hogberg et al. |

FOREIGN PATENT DOCUMENTS

| | | | | |
|---|---|---|---|---|
| EP | 1939192 A1 * | 7/2008 | | C07D 407/06 |
| WO | 2007/070985 A1 | 6/2007 | | |
| WO | WO-2008010831 A1 * | 1/2008 | | C07D 209/52 |

OTHER PUBLICATIONS

Zhang, Feng, et al., "CRISPR/Cas9 for genome editing: progress, implications and challenges," Human Molecular Genetics, vol. 23 (2014), pp. R40-R46.
Yin, Gang, et al., "Aglycosylated antibodies and antibody fragments produced in a scalable in vitro transcription-translation system," mAbs, vol. 4, No. 2 (2012), pp. 217-225.
Winter, Greg, et al., "Man-made antibodies," Nature, vol. 349 (1991), pp. 293-299.
Taylor, P.R., et al., "Macrophage Receptors and Immune Recognition," Annu. Rev. Immunol., vol. 23 (2005), pp. 901-944.
Steinberger, Peter, et al., "Generation and Characterization of a Recombinant Human CCR5-specific Antibody," J. Biol. Chem., vol. 275, No. 46 (2000), pp. 36073-36078.
Schenk, Mirjam, et al., "TREM-1-expressing intestinal macrophages crucially amplify chronic inflammation in experimental colitis and inflammatory bowel diseases," J. Clin. Invest., vol. 117 (2007), pp. 3097-3106.
Riechmann, Lutz, et al., "Reshaping human antibodies for therapy," Nature, vol. 332 (1988), pp. 323-329.
Radar, Christoph, et al., "A phage display approach for rapid antibody humanization: Designed combinatorial V gene libraries," Proc. Nat. Acad. Sci. U.S.A., vol. 95 (1998), pp. 8910-8915.
Queen, Cary, et al., "A humanized antibody that binds to the interleukin 2 receptor," Proc. Natl. Acad. Sci. U.S.A., vol. 86 (1989), pp. 10029-10033.
Presta, Leonard, "Antibody engineering," Current Opinion in Biotechnology, vol. 3 (1992), pp. 593-596.
Poukoulidou, Thekla, et al., "TREM-1 expression on neutrophils and monocytes of septic patients: relation to the underlying infection and the implicated pathogen," BMC Infectious Diseases, vol. 11 (2011) (8 pages).

(Continued)

*Primary Examiner* — Andrew D Kosar
*Assistant Examiner* — John D McAnany
(74) *Attorney, Agent, or Firm* — Thomas Horstemeyer LLP

(57) ABSTRACT

Provided are methods for the isolation of phorbol from seed sources and the use of the phorbol for the generation of tigliane tiglate and derivatives thereof.

3 Claims, 15 Drawing Sheets

(56) References Cited

OTHER PUBLICATIONS

Oakley, Holly, et al., "Intraneuronal beta-Amyloid Aggregates, Neurodegeneration, and Neuron Loss in Transgenic Mice with Five Familial Alzheimer's Disease Mutations: Potential Factors in Amyloid Plaque Formation," The Journal of Neuroscience, vol. 26 (2006), pp. 10129-10140.

Nathan, Carl, et al., "TREM-1: A new regulator of innate immunity in sepsis syndrome," Nat. Med., vol. 7 (2001), pp. 530-532.

Marks, James D., et al., "By-passing Immunization: Human Antibodies from V-gene Libraries Displayed on Phage," J. Mol. Biol., vol. 222 (1991), pp. 581-597.

Maccallum, Robert M., et al., "Antibody-antigen Interactions: Contact Analysis and Binding Site Topography," J. Mol. Biol., vol. 272 (1996), pp. 732-745.

Liu, Qingkun, et al., "Peripheral TREM1 responses to brain and intestinal immunogens amplify stroke severity," Nat. Immunol., vol. 20, No. 8 (2019), pp. 1023-1034.

Lefranc, Marie-Paule, et al., "IMGT unique numbering for immunoglobulin and T cell receptor variable domains and IG superfamily V-like domains," Developmental and Comparative Immunology, vol. 27 (2003), pp. 55-77.

Kozbor, D., et al., "A human hybrid myeloma for production of human monoclonal antibodies," The Journal of Immunology, vol. 133, No. 6 (1984), pp. 3001-3005.

Köhler, G., et al. "Continuous cultures of fused cells secreting antibody of predefined specificity," Nature, vol. 256 (1975), pp. 495-497.

Jones, Peter T., et al. "Replacing the complementarity-determining regions in a human antibody with those from a mouse," Nature, vol. 321 (1986), pp. 522-525.

Jankowsky, Joanna L., et al. "Mutant presenilins specifically elevate the levels of the 42 residue β-amyloid peptide in vivo: evidence for augmentation of a 42-specific γ secretase," Human Molecular Genetics, vol. 13, No. 2 (2004), pp. 159-170.

International Search Report and Written Opinion, PCT Application No. PCT/US2022/019718, mailed Jul. 5, 2022.

Ahmed, Waled Abdo, et al., "Phorbol Ester as Toxic Constituents of Tropical Jatropha Curcas Seed Oil," European Journal of Scientific Research, vol. 31, No. 3 (2009), pp. 429-436.

Wender, Paul A., et al., "The First Formal Asymmetric Synthesis of Phorbol," Journal of American Chemical Soc., vol. 119 (1997), p. 7897.

Johnson, D. E.; Burtness, B.; Leemans, C. R.; Lui, V. W.Y.; Bauman, J. E.; Grandis, J. R. Head and Neck Squamous Cell Carcinoma. Nat. Rev. Dis. Prim. 2020, 6 (1) DOI: 10.1038/s41572-020-00224-3.

Osazuwa-Peters, N.; Simpson, M. C.; Zhao, L.; Boakye, E. A.; Olomukoro, S. I.; Deshields, T.; Loux, T. M.; Varvares, M. A.; Schootman, M. Suicide Risk among Cancer Survivors: Head and Neck versus Other Cancers. Cancer 2018, 124 (20), 4072-4079 DOI: 10.1002/cncr.31675.

Barnett, C. M. E.; Broit, N.; Yap, P. Y.; Cullen, J. K.; Parsons, P. G.; Panizza, B. J.; Boyle, G. M. Optimising Intratumoral Treatment of Head and Neck Squamous Cell Carcinoma Models with the Diterpene Ester Tigilanol Tiglate. Invest. New Drugs 2019, 37 (1), 1-8 DOI: 10.1007/s10637-018-0604-y.

Panizza, B. J.; de Souza, P.; Cooper, A.; Roohullah, A.; Karapetis, C. S.; Lickliter, J. D. Phase I Dose-Escalation Study to Determine the Safety, Tolerability, Preliminary Efficacy and Pharmacokinetics of an Intratumoral Injection of Tigilanol Tiglate (EBC-46). EBioMedicine 2019, 50, 433-441 DOI: 10.1016/j.ebiom.2019.11.037.

Boyle, G. M.; D'Souza, M. M. A.; Pierce, C. J.; Adams, R. A.; Cantor, A. S.; Johns, J. P.; Maslovskaya, L.; Gordon, V. A.; Reddell, P. W.; Parsons, P. G. Intra-Lesional Injection of the Novel PKC Activator EBC-46 Rapidly Ablates Tumors in Mouse Models. PLoS One 2014, 9 (10), 1-12 DOI: 10.1371/journal.pone.0108887.

Moses, R. L.; Boyle, G. M.; Howard-Jones, R. A.; Errington, R. J.; Johns, J. P.; Gordon, V.; Reddell, P.; Steadman, R.; Moseley, R. Novel Epoxy-Tiglianes Stimulate Skin Keratinocyte Wound Healing Responses and Re-Epithelialization via Protein Kinase C Activation. Biochem. Pharmacol. 2020, 178 (March), 114048 DOI: 10.1016/j.bcp.2020.114048.

Lamont, R. W.; Conroy, G. C.; Reddell, P.; Ogbourne, S. M. Population Genetic Analysis of a Medicinally Significant Australian Rainforest Tree, Fontainea Picrosperma C.T. White (Euphorbiaceae): Biogeographic Patterns and Implications for Species Domestication and Plantation Establishment. BMC Plant Biol. 2016, 16 (1), 1-12 DOI: 10.1186/s12870-016-0743-2.

Grant, E. L.; Wallace, H. M.; Trueman, S. J.; Reddell, P. W.; Ogbourne, S. M. Floral and Reproductive Biology of the Medicinally Significant Rainforest Tree, Fontainea Picrosperma (Euphorbiaceae). Ind. Crops Prod. 2017, 108 (Jul.), 416-422 DOI: 10.1016/j.indcrop.2017.07.013.

Grant, E. L.; Conroy, G. C.; Lamont, R. W.; Reddell, P. W.; Wallace, H. M.; Ogbourne, S. M. Short Distance Pollen Dispersal and Low Genetic Diversity in a Subcanopy Tropical Rainforest Tree, Fontainea Picrosperma (Euphorbiaceae). Heredity (Edinb). 2019, 123 (4), 503-516 DOI: 10.1038/s41437-019-0231-1.

Godfree, R. C.; Knerr, N.; Godfree, D.; Busby, J.; Robertson, B.; Encinas-Viso, F. Historical Reconstruction Unveils the Risk of Mass Mortality and Ecosystem Collapse during Pancontinental Megadrought. Proc. Natl. Acad. Sci. U. S. A. 2019, 116 (31), 15580-15589 DOI: 10.1073/pnas.1902046116.

Honnay, O.; Jacquemyn, H. Susceptibility of Common and Rare Plant Species to the Genetic Consequences of Habitat Fragmentation. Conserv. Biol. 2007, 21 (3), 823-831 DOI: 10.1111/j.1523-1739.2006.00646.x.

Newman, D. J.; Cragg, G. M. Natural Products as Sources of New Drugs from 1981 to 2014. 2016 DOI: 10.1021/acs.jnatprod.5b01055.

Goel, G.; Makkar, H. P. S.; Francis, G.; Becker, K. Phorbol Esters: Structure, Biological Activity, and Toxicity in Animals. Int. J. Toxicol. 2007, 26 (4), 279-288 DOI: 10.1080/10915810701464641.

Ryves, W. J.; Evans, A. T.; Olivier, A. R.; Parker, P. J.; Evans, F. J. Activation of the PKC-Isotypes Alpha, Beta 1, Gamma, Delta and Epsilon by Phorbol Esters of Different Biological Activities. FEBS Lett. 1991, 288 (1-2), 5-9 Doi: 0014-5793(91)80989-G [pii].

Beans, E. J.; Fournogerakis, D.; Gauntlett, C.; Heumann, L. V; Kramer, R.; Marsden, M. D.; Murray, D.; Chun, T.-W.; Zack, J. A.; Wender, P. A. Highly Potent, Synthetically Accessible Prostratin Analogs Induce Latent HIV Expression in Vitro and Ex Vivo. Proc. Natl. Acad. Sci. U. S. A. 2013, 110 (29), 11698-11703 DOI: 10.1073/pnas.1302634110.

Wender, P. A.; Debrabander, J.; Harran, P. G.; Jimenez, J.-M.; Koehler, M. F. T.; Lippa, B.; Park, C.-M.; Siedenbiedel, C.; Pettit, G. R. The Design, Computer Modeling, Solution Structure, and Biological Evaluation of Synthetic Analogs of Bryostatin 1. Proc. Natl. Acad. Sci. U. S. A. 1998, 95 (Copyright (C) 2010 American Chemical Society (ACS). All Rights Reserved.), 6624-6629 DOI: 10.1073/pnas.95.12.6624.

Wender, P. A.; Koehler, K. F.; Sharkey, N. A.; Dell'Aquila, M. L.; Blumberg, P. M. Analysis of the Phorbol Ester Pharmacophore on Protein Kinase C as a Guide to the Rational Design of New Classes of Analogs (Tumor Promotion/ Teleocidin/Phorbol Ester Receptor/ Epidermal Growth Factor). Proc. Natl. Acad. Sci 1986, 83 (June), 4214-4218.

Wender, P. a; Kee, J.-M.; Warrington, J. M. Practical Synthesis of Prostratin, DPP, and Their Analogs, Adjuvant Leads against Latent HIV. Science 2008, 320 (5876), 649-652 DOI: 10.1126/science.1154690.

Pagani, A.; Gaeta, S.; Savchenko, A. I.; Williams, C. M.; Appendino, G. An Improved Preparation of Phorbol from Croton Oil. Beilstein J. Org. Chem. 2017, 13, 1361-1367 DOI: 10.3762/bjoc.13.133.

Schmidt, R.; Hecker, E. Autoxidation of Phorbol Esters under Normal Storage Conditions. Cancer Res. 1975, 35 (5), 1375-1377.

Evans, D. A.; Chapman, K. T. The Directed Reduction of B-Hydroxy Ketones Employing Me4NHB(OAc)3. Tetrahedron Lett. 1986, 27 (49), 5939-5942 DOI: 10.1016/S0040-4039(00)85367-8.

(56) References Cited

OTHER PUBLICATIONS

Jin, Y.; Shi, L.; Zhang, D.; Wei, H.; Si, Y.; Ma, G. A Review on Daphnane-Type Diterpenoids and Their Bioactive Studies. Molecules 2019, 24 (1842), 1-14.

Hanson, R. M. Epoxide Migration (Payne Rearrangement) and Related Reactions. Org. React. 2004, 1-156.

Wender, P. A.; Buschmann, N.; Cardin, N. B.; Jones, L. R.; Kan, C.; Kee, J.-M.; Kowalski, J. A.; Longcore, K. E. Gateway Synthesis of Daphnane Congeners and Their Protein Kinase C Affinities and Cell-Growth Activities. Nat. Chem. 2011, 3 (8), 615-619 DOI: 10.1038/nchem.1074.

Ghogare, A. A.; Greer, A. Using Singlet Oxygen to Synthesize Natural Products and Drugs. Chem. Rev. 2016, 116 (17), 9994-10034 DOI: 10.1021/acs.chemrev.5b00726.

Gupta, V. K.; Mittal, A.; Jhare, D.; Mittal, J. Batch and Bulk Removal of Hazardous Colouring Agent Rose Bengal by Adsorption Techniques Using Bottom Ash as Adsorbent. RSC Adv. 2012, 2 (22), 8381-8389 DOI: 10.1039/c2ra21351f.

Boudreault, P. L.; Mattler, J. K.; Wender, P. A. Studies on the Regio- and Diastereo-Selective Epoxidation of Daphnanes and Tiglianes. Tetrahedron Lett. 2015, 56 (23), 3423-3427 DOI: 10.1016/j.tetlet.2015.01.126.

Simone, G. Tigliane Diterpenoids: Isolation, Chemistry and Preliminary Biosynthetic Studies of a Medicinal Relevant Class of Natural Compounds, Universita Del Piemonte Orientale, 2019.

Newton, A. C. & Brognard, J. Reversing the paradigm: protein kinase C as a tumor suppressor. Trends Pharmacol. Sci. 38, 438-447 (2017).

Kim, J. T. et al. Latency reversal plus natural killer cells diminish HIV reservoir in vivo. Nat. Commun. 13, 121 (2022).

Ramakrishna, S. et al. Modulation of target antigen density improves CAR T-cell functionality and persistence. Clin. Cancer Res. 25, 5329-5341 (2019).

Hardman, C. et al. Synthesis and evaluation of designed PKC modulators for enhanced cancer immunotherapy. Nat. Commun. 11, 1-11 (2020).

Marro, B. S. et al. Discovery of small molecules for the reversal of T-cell exhaustion. Cell Rep. 29, 3293-3302 (2019).

Farlow, M. R. et al. A randomized, double-blind, placebo-controlled, phase II study assessing safety, tolerability, and efficacy of bryostatin in the treatment of moderately severe to severe Alzheimer's disease. J. Alzheimers Dis. 67, 555-570 (2019).

Cullen, J. K. et al. Activation of PKC supports the anticancer activity of tigilanol tiglate and related epoxytiglianes. Sci Rep. 11, 1-14 (2021).

Miller, J. et al. Dose characterization of the investigational anticancer drug tigilanol tiglate (EBC-46) in the local treatment of canine mast cell tumors. Front. Vet. Sci. 6, 1-10 (2019).

FDA Approves First Intratumoral Injection to Treat Non-Metastatic Mast Cell Tumors in Dogs https://www.fda.gov/news-events/press-announcements/fda-approves-first-intratumoral-injection-treat-non-metastatic-mast-cell-tumors-dogs (2020).

De Ridder, T. R. et al. Randomized controlled clinical study evaluating the efficacy and safety of intratumoral treatment of canine mast cell tumors with tigilanol tiglate (EBC-46). J. Vet. Intern. Med. 35, 415-429 (2020).

Grant, E. L. et al. Floral attraction and flower visitors of a subcanopy, tropical rainforest tree, Fontainea Picrosperma. Ecol. Evol. 11, 10468-10482 (2021).

Grant, E. Reproductive Biology, Flowering and Genetics of Fontainea picrosperma (Euphorbiaceae). PhD thesis, Univ. Sunshine Coast (2020).

Wender, P. A., Quiroz, R. V. & Stevens, M. C. Function through synthesis-informed design. Acc. Chem. Res. 48, 752- 760 (2015).

Kim, K. E., Kim, A. N., McCormick, C. J. & Stoltz, B. M. Late-stage diversification: a motivating force in organic synthesis. J. Am. Chem. Soc. 143, 16890-16901 (2021).

Newman, D. J. & Cragg, G. M. Natural products as sources of new drugs over the nearly four decades from Jan. 1981 to Sep. 2019. J. Nat. Prod. 83, 770-803 (2020).

Kawamura, S., Chu, H., Felding, J. & Baran, P. S. Nineteen-step total synthesis of (+)-phorbol. Nature 532, 90-93 (2016).

Ahmed, W. A. & Salimon, J. Phorbol ester as toxic constituents of tropical Jatropha curcas seed oil. Eur. J. Sci. Res. 31, 429-436 (2009).

Hou, Z., Yao, G. & Song, S. Daphnane-type diterpenes from genus Daphne and their anti-tumor activity. Chin. Herbal Medicines 13, 145-156 (2021).

Zhang, G., Kazanietz, M. G., Blumberg, P. M. & Hurley, J. H. Crystal structure of the Cys2 activator-binding domain of protein kinase Co in complex with phorbol ester. Cell 81, 917-924 (1995).

Sagadevan, A., Hwang, K. C. & Su, M.-D. Singlet oxygen-mediated selective C-H bond hydroperoxidation of ethereal hydrocarbons. Nat. Commun. 8, 1812 (2017).

Benner, N. L. et al. Functional DNA delivery enabled by lipid-modified charge-altering releasable transporters (CARTs). Biomacromolecules 19, 2812-2824 (2018).

* cited by examiner tigilanol tiglate (1)
*12% yield over 12 steps*
*> 2.5 g prepared*

C5β-hydroxy phorbol diacetate (7)
*37% yield over 6 steps*
*> 10 g prepared* phorbol (2)
isolated from
*Croton tiglium seeds*

Tigilanol tiglate (1)

Kirkinine

Yuanhuapin

Gnidimacrin

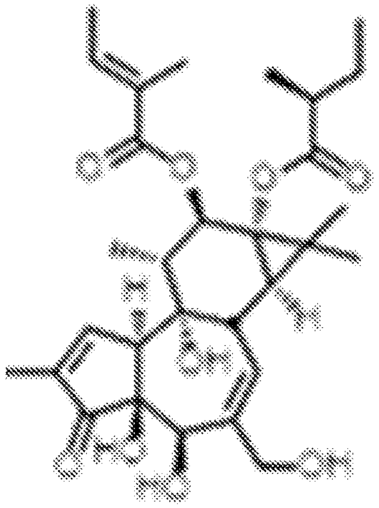
SUW400 (13)
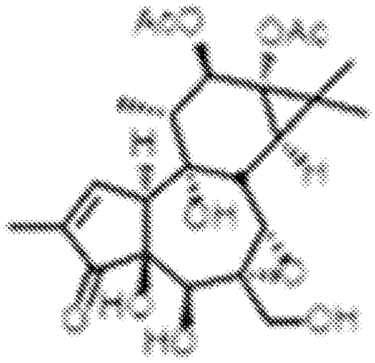
SUW401 (14)
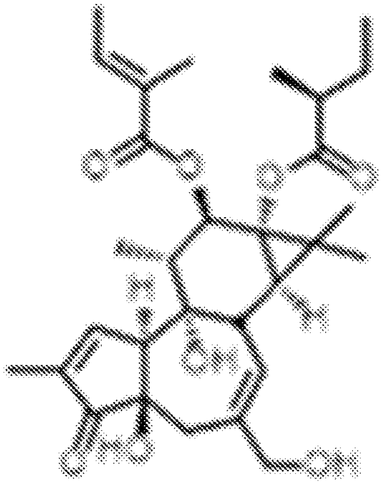
SUW402 (15)
*Fig. 4A*
| | PKC $K_i$ (nM) | |
|---|---|---|
| Compound | beta-I | theta |
| tigilanol tiglate (1) | 2.4 (2.3-2.5) | 26.6 (25.4-27.7) |
| SUW400 (13) | 2.0 (1.9-2.1) | 24.9 (23.1-26.9) |
| SUW401 (14) | > 1000 | > 1000 |
| SUW402 (15) | 0.55 (0.53-0.57) | 0.95 (0.92-0.98) |
*Fig. 4B*

5 6 7 8 4 9 11 10 12

13a
($R^1$ = $^nC_{11}H_{23}$, $R^2$ = Me)
13b
($R^1$ = $R^2$ = Me)

22a
($R^1$ = $^nC_{11}H_{23}$, $R^2$ = Me)
22b
($R^1$ = $R^2$ = Me)

23a
($R^1$ = $^nC_{11}H_{23}$, $R^2$ = Me)
23b
($R^1$ = $R^2$ = Me)

10
($R^1$ = $^nC_{11}H_{23}$, $R^2$ = Me)

*Binding Affinity ($K_i$, nM)*

| | **10** | **13a** |
|---|---|---|
| ***PKC α*** | 1.2 | |
| ***PKC β*** | 6.1 | 3.6 |
| ***PKC γ*** | 9.2 | |
| ***PKC δ*** | | 3.4 |

22a 23a 26 25 24

| Conditions: | 23a | 26 | 25 | 24 | 22a |
|---|---|---|---|---|---|
| $CDCl_3$/acetone (1:1 v/v) | 30 % | 0 | 0 | 5 % | 50 % |
| acetone | 0 % | 0 | 21 % | 5 % | 30 % |
| $CHCl_3$/acetone (3:1 v/v) | 95 % | 0 | 0 | 0 | 0 |

23a ($R^1$ = $^nC_{11}H_{23}$, $R^2$ = Me)

23b ($R^1$ = $R^2$ = Me)

27

28 (R = H)

29 (R = (E)-$CH_3$-$CH_3$=C($CH_3$)-CO)

30

1

27

14

| $R^1$ | $R^2$ | Yield over 2 steps | Binding Affinity ($K_i$, nM) PKC? |
|---|---|---|---|
| | | | |

Newton, A. C. Critical Reviews in Biochemistry and Molecular Biology. 2018, *53*(2), 208-230.

Croton tiglium seeds

Phorbol

EBC-46 Analogs

Trigowin A

Tigilanol Tiglate (EBC-46)

Tigliane analogs

SYNTHESIS OF TIGILANOL TIGLATE AND ANALOGS THEREOF

CROSS-REFERENCE TO RELATED APPLICATION

This application claims the benefit of U.S. Provisional Application No. 63/159,163 entitled "SYNTHESIS OF TIGILANOL TIGLATE (EBC-46) AND ANALOGS FOR PKC-RELATED DISEASES" filed on Mar. 10, 2021, the entire disclosure of which is incorporated herein by reference.

STATEMENT REGARDING FEDERALLY SPONSORED RESEARCH OR DEVELOPMENT

This invention was made with Government support under grant CA031845 awarded by the NIH National Cancer Institute. The Government has certain rights in the invention.

TECHNICAL FIELD

The present disclosure is generally related to methods of isolating phorbols from seed sources and the synthesis of tigilanol tiglate and analogs thereof.

BACKGROUND

Ligands that modulate protein kinase C (PKC) signaling (Newton et al., *Trends Pharmacol. Sci.* 38: 438-447 (2017)) have been implicated in therapeutic approaches to HIV/AIDS eradication (Kim et al., *Nat. Commun.* 13: 121 (2022)), antigen-enhanced antibody and CART cell therapies (Ramakrishna et al., *Clin. Cancer Res.* 25: 5329-5341 (2019); Hardman et al., *Nat. Commun.* 11: 1-11 (2020)), suppression of T cell exhaustion in cancer immunotherapy (Marro et al., *Cell Rep.* 29: 3293-3302 (2019)), Alzheimer's disease (Sun et al., *J. Pharmacol. Exp. Ther.* 349: 393-401 (2014)) and multiple sclerosis (Kornberg et al., *Proc. Nat. Acad. Sc. U.S.A.* 115: 2186-2191 (2018)). Some modulators have advanced toward clinical evaluation (Gutierrez et al., *Aids* 30: 1385-1392 (2016); Farlow et al., *J. Alzheimer's Dis.* 67: 555-570 (2019)), including tigilanol tiglate (1, EBC-46), a naturally occurring tigliane diterpenoid recently evaluated in phase I clinical trials for the treatment of a broad range of cancers in humans and currently in trials for head and neck squamous cell carcinomas (Panizza et al., *EBioMedicine* 50: 433-441 (2019)). Intratumoral injection of EBC-46 induces rapid tumor ablation, in part by a proposed isoform-selective modulation of PKC (Cullen et al., *Sc. Rep.* 11: 1-14 (2021); Miller et al., *Front. Vet. Sc.* 6: 1-10 (2019)). Following administration, EBC-46 induces a localized immune response and rupture of tumor vasculature, leading to hemorrhagic necrosis, subsequent clearance of the solid tumor, and facilitated wound healing (Moses et al., *Biochem. Pharmacol.* 178: 114048 (2020); Boyle et al., *PLoS One* 9: 1-12 (2014)). Recently, EBC-46, branded STELFONTA®, received approval by the US Food and Drug Administration (FDA) and the European Medicines Agency for treatment of non-metastatic mast cell tumors in canines. In a recent clinical study, a 75% complete response was observed in canines after a single intratumoral injection and 88% remission after a second dose (De Ridder et al., *J. Vet. Intern. Med.* 35: 415-429 (2020)), prompting its current evaluation in human trials.

Currently, the only source of EBC-46 is the dioecious blushwood tree (*Fontainea picrosperma*), a rainforest Euphorbiaceae, limited in number and endemic to a small region of Northeastern Australia (Lamont et al., *BMC Plant Biol.* 16: 1-12 (2016); Grant et al., *Ecol. Evol.* 11: 10468-10482 (2021)). As reported, to access EBC-46 and ester variants from rain forest tree seeds, the seeds are extracted with ethanol, and the resultant extract is partitioned between petroleum ether and water. The contents of the organic phase are then converted to EBC-46 following six chromatographic purifications and five low-yielding synthetic steps (~5% yield) (Paul et al., U.S. Pat. No. 9,770,431 B2, (2017)). Prompted by its limited natural source, environmental considerations and its emerging clinical value, efforts to improve EBC-46 production have been directed at cultivating its source plant, *F. picrosperma*, in designed plantations (Lamont et al., *BMC Plant Biol.* 16: 1-12 (2016)). However, this source, while avoiding rain forest harvesting, would still be pollinator limited and at risk of disruption by climate variations and invasive pathogens (Grant et al., *Ecol. Evol.* 11: 10468-10482 (2021); Grant, E. *University of Sunshine Coast, Queensland* (2020)). More geographically distributed and diverse sources would offer a more sustainable supply for research and clinical needs.

SUMMARY

One aspect of the disclosure encompasses embodiments of a method for the synthesis of tigilanol tiglate, the method comprising the steps as shown in the schema shown in FIG. 3 of the disclosure.

Another aspect of the disclosure encompasses embodiments of a method for the synthesis of tigilanol tiglate, the method comprising the steps as shown in the schema shown in FIG. 3 of the disclosure.

Yet another aspect of the disclosure encompasses embodiments of a method of isolating Phorbol (2) from Croton tiglium seeds, the method comprising the steps of: (a) pulverizing Croton tiglium seeds; (b) extracting the pulverized seeds by refluxing with methanol and concentrating the product thereof to an oil; (c) extracting the oil with a plurality of methanol washes and pooling the methanol washes; (d) adding cesium carbonate to the methanol washes with prolonged stirring; (e) acidifying the product of the preceding step with 6M sulfuric acid to a pH of 5.5; (f) filtering the acidified product and concentrating the filtrate therefrom under reduced pressure at 30° C.; (g) saturating the aqueous suspension from step (f) sodium chloride; (h) washing the aqueous phase with diethyl ether; and (i) extracting the diethyl ether with tetrahydrofuran (THF) and concentrating the THF extract under reduced pressure at 30° C.; drying the THF extract concentrate and purifying by silica gel vacuum column chromatography.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 2A illustrates representative members of the tigliane and daphnane families with shared B-ring functionality.

FIG. 2B illustrates the X-ray crystal structure of phorbol 13-acetate bound to the C1 domain of PKC-δ (left) and predicted binding of EBC-46 to the C1 domain of PKC-δ (right) (dotted lines represent hydrogen bonds).

FIGS. 4A-4C illustrate novel analogs, binding assay data, and microscope images of PKC translocation.

FIG. 4A illustrates analogs of tigilanol tiglate (1).

FIG. 4B illustrates PKC binding data of 13, 14, and 15 versus tigilanol tiglate (1).

FIG. 4C illustrates PKC-$\beta_I$-GFP translocation in CHO-K1 cells mediated by 1 and 13 (1000 nM) (scale bars represent 10 microns).

FIG. 9A illustrates a successful synthetic sequence toward 5β-hydroxy-6α,7α-epoxy tigliane and preliminary binding assessment of 10 and 13a.

DETAILED DESCRIPTION

Figure 1:
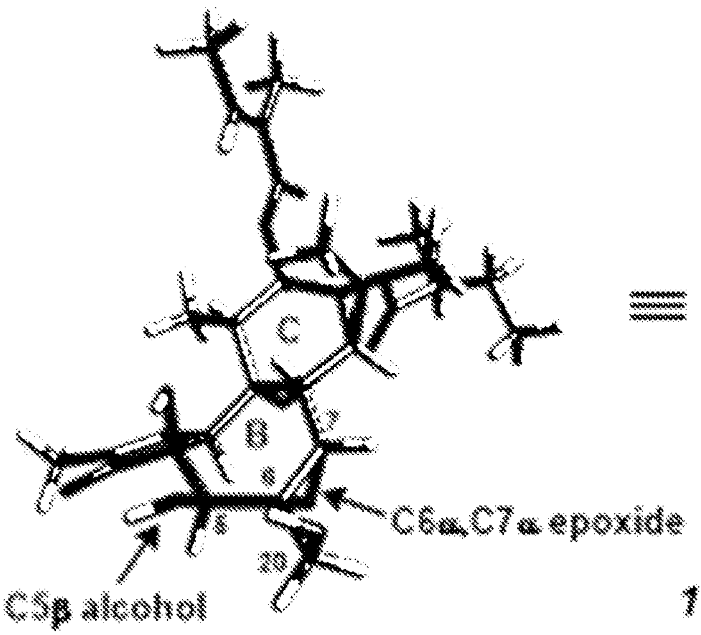
FIG. 1 illustrates a retrosynthetic analysis of tigilanol tiglate (1) from phorbol and a computer-generated model of its 3-dimensional structure.
Figure 1:
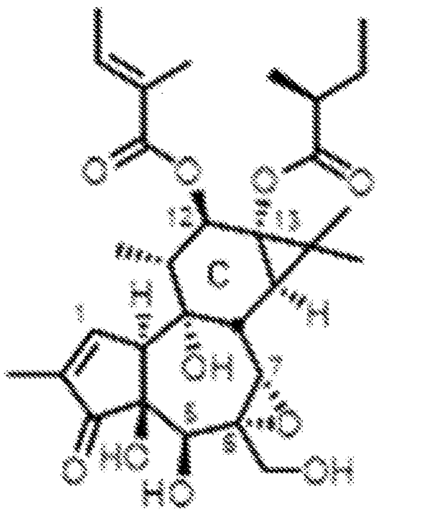
Figure 1:
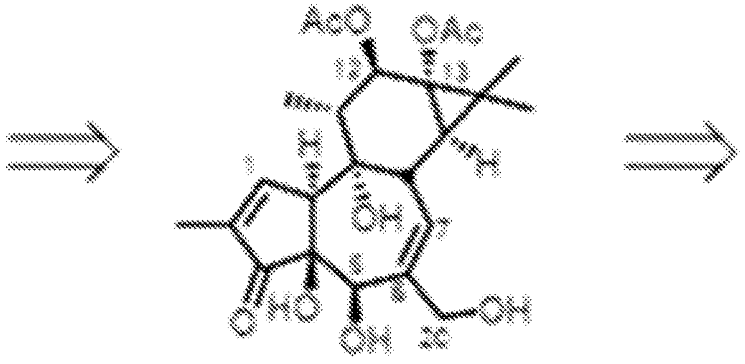
Figure 1:
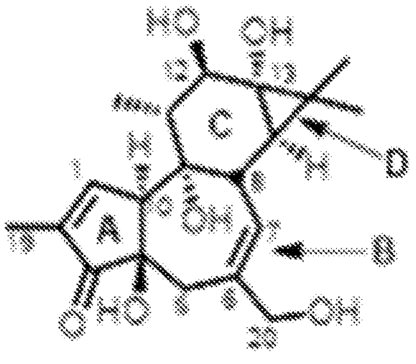

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, medicine, neurology, and the like, which are within the skill of the art.

The following examples are put forth so as to provide those of ordinary skill in the art with a complete disclosure and description of how to perform the methods and use the compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

5

6

It must be noted that, as used in the specification and the appended claims, the singular forms "a," "an," and "the" include plural referents unless the context clearly dictates otherwise.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Abbreviations human immunodeficiency virus, HIV; antiretroviral therapy, ART; protein kinase C, PKC;

Definitions

The term "direct bond" refers to a chemical bond such as a covalent bond or an ionic bond.

The term "substituted" refers to any one or more hydrogens on the designated atom that can be replaced with a selection from the indicated group, provided that the designated atom's normal valence is not exceeded, and that the substitution results in a stable compound. When a substituent is keto (i.e., C—C(=O)—C), then 2 hydrogens on the atom can be replaced. Keto substituents are not present on aromatic moieties. When a ring system (e.g., carbocyclic or heterocyclic) is said to be substituted with a double bond, it is intended that the carbonyl group or double bond be part of the ring.

The term "aliphatic group" refers to a saturated or unsaturated linear or branched hydrocarbon group and encompasses alkyl, alkenyl, and alkynyl groups, for example.

The terms "alkyl" or "alkyl group" as used herein refer to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, s-pentyl, and nonyl. The term "lower alkyl" means an alkyl group having less than 10 carbon atoms.

The terms "alkenyl" or "alkenyl group" as used herein refer to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

The term "substituted," as in "substituted alkyl", "substituted cycloalkyl," "substituted cycloalkenyl," substituted aryl, "substituted biaryl," "substituted fused aryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

The terms "halo", "halogen", or "halogen radical" as used herein refer to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "cycloalkyl" refers to a non-aromatic mono- or multicyclic ring system of about 3 to about 10 carbon atoms, preferably of about 5 to about 10 carbon atoms. Advantageous ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, tricyclo[3.3.1.1$^{3.7}$]decane, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Advantageous ring sizes of rings of the ring system include about 5 to about 6 ring atoms. Examples of monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

The terms "aralkyl" and "heteroaralkyl" as used herein refer to aryl and heteroaryl moieties, respectively, that are linked to a main structure by an intervening alkyl group, e.g., containing one or more methylene groups.

The term "fluorobenzyl" refers to a benzyl group wherein the phenyl moiety is substituted with one or more fluorine atoms, including 2, 3, 4 and 5 fluorine atom substituents.

Similarly, "halobenzyl" refers to benzyl substituted with one or more different halogens, including fluorine, chlorine, bromine, and iodine (not astatine).

The terms "sulfide" and "thioether" as used herein, alone or in combination, refer to a sulfur atom covalently linked to two atoms; the formal oxidation state of said sulfur is (II). These terms may be used interchangeably.

The term "sulfanyl" as used herein, alone or in combination, refers to the —S—R group, wherein R may be a group such as: alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl ($—SCH_3$) and iso-propylsulfanyl ($—SCH(CH_3)_2$) and the like.

The term "sulfoxide" as used herein, alone or in combination, refers to a sulfur atom covalently linked to three atoms, at least one of which is an oxygen atom; the formal oxidation state of said sulfur atom is (IV).

The term "sulfinyl" as used herein, alone or in combination, refers to the groups —S(O)—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfinyl group includes methylsulfinyl ($—S(O)CH_3$) and the like.

The term "sulfone" as used herein, alone or in combination, refers to a sulfur atom covalently linked to four atoms, at least two of which are oxygen atoms; the formal oxidation state of said sulfur atom is (VI).

The term "sulfonyl" as used herein, alone or in combination, refers to the groups $—S(O_2)—R$, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfonyl group includes methylsulfonyl ($—S(O_2)CH_3$) and the like.

The term "phosphine" as used herein, alone or in combination, refers to a phosphorus atom covalently linked to at least one carbon atom, wherein the formal oxidation state of said phosphorus is (III).

The term "phosphinyl" as used herein, alone or in combination, refers to the monoradical derived from a phosphite group, as defined above.

The term "phosphonate" as used herein, alone or in combination, refers to a phosphorus atom covalently linked to four atoms, three of which are oxygen and one of which is carbon wherein the formal oxidation state of said phosphorus is (V).

The term "phosphonyl" as used herein, alone or in combination, refers to the monoradical derived from a phosphonate group, as defined above.

The term "phosphate" as used herein, alone or in combination, refers to a phosphorus atom covalently linked to four oxygen atoms, wherein the formal oxidation state of said phosphorus is (V).

The term "phosphatidyl" as used herein, alone or in combination, refers to the monoradical derived from a phosphate group, as defined above.

The terms ketone, ester, ether, and acyl have their art recognized meanings.

To the extent that the disclosed compounds, and salts thereof, may exist in their tautomeric form, all such tautomeric forms are contemplated herein as part of the present disclosure.

All stereoisomers of the compounds of the present disclosure, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" refers to a compound of the present disclosure that can be modified by making acid or base salts thereof. Pharmaceutically acceptable salt refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Examples of pharmaceutically acceptable salts include, but are not limited to, mineral or organic acid salts of basic residues such as amines; and alkali or organic salts of acidic residues such as carboxylic acids.

In the event that embodiments of the present disclosure form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are advantageous, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

The terms "treat", "treatment", "treating", and the like as used herein refer to acting upon a disease or disorder with an agent to affect the disease or disorder by improving or altering it. The improvement or alteration may include an improvement in symptoms or an alteration in the physiologic pathways associated with the disease or disorder. "Treatment," as used herein, covers one or more treatments of a disease in a host (e.g., a mammal, typically a human or non-human animal of veterinary interest), and includes: (a) reducing the risk of occurrence of the disease in a subject determined to be predisposed to the disease but not yet diagnosed as infected with the disease (HIV/AIDS) (b) impeding the development of the disease, and/or (c) relieving the disease, e.g., causing regression of the disease and/or relieving one or more disease symptoms.

DESCRIPTION

Protein kinase C (PKC) modulators are candidates for the therapeutic treatment of a variety of major diseases. Some PKC modulators are in clinical trials for Alzheimer's disease (AD), HIV/AIDS eradication, and cancer. However, these highly potent PKC modulators are also difficult to formulate, display non-optimal efficacy as drugs, and possess unacceptable toxicities. Administration of these compounds often elicits acute toxicities due to bolus effects arising from the high concentration of agent at the site of administration or systemically. This bolus toxicity can be decreased by slow administration, but this adds complications to both preclinical animal studies and the clinical use of these compounds. For example, the highly potent PKC modulator bryostatin 1 is administered over 24 hours via intravenous injection of a diluted saline solution. In other cases, toxicities arrive from the undesired biodistribution of the compound which is determined by the properties of the compound. The combination of formulation problems, bolus toxicity, toxicities arising from undesired biodistribution, and efficacy severely reduces the therapeutic window for such compounds. Additionally, many PKC modulators suffer from stability problems, undergoing adventitious aerobic or metabolic oxidation. This compromises their shelf stability before administration and limits their lifetime during circulation in a patient after administration. While the properties of many PKC modulators can be improved to combat stability problems, often that improvement is accompanied by higher toxicities or lower efficacies. In contrast to bolus administration which provides short-lived but high exposure to the modulator, controlled release of free agent from a modified precursor (prodrug) allows for sustained release of the modulator at optimal concentrations for extended periods (Rautio et al., (2008), *Nat. Rev. Drug. Discov.* 7: 255). This offers improved efficacy and tolerability.

The reversible attaching of a masking group to one of these functional elements results in compounds that have altered properties and are temporarily ineffective as PKC modulators until the free agent is released by enzymatic or biological cleavage in vivo (Ettmayer et al., (2004) *J. Med. Chem.* 47:2393; Liederer & Borchardt (2006) *Pharm. Sci.* 95: 1177). These compounds display rates of release and biodistribution that can be tuned and controlled by design. Specifically, it has now been demonstrated that these compounds have delayed activity profiles in an HIV latency reversal assay (t½=24-72 h) versus the parent compound (t½ less than 24 h), but limited toxicity (mouse kill at 150 μg for the prodrugs, versus 60 μg for the parent compound). Additionally, the prodrugs of the disclosure display improved efficacy over the parent compound at comparable doses (nearly 100% cell activation by a prodrug versus 60-80% by the parent compound).

Accordingly, provided is a strategy for the design of prodrugs of PKC modulators that show efficacy coupled with low levels of toxicity and improved stability. These prodrug compounds are useful in academic research (animal studies), as candidates for preclinical research, and as therapeutic agents. By taking advantage of a pharmacophore-based strategy, this method provides access to prodrugs of PKC modulators of diverse scaffolds, including, but not limited to tigliane diterpenes, ingenane diterpenes, daphnane diterpene orthoesters (DDOs), diacylglycerols (DAGs), and bryostatins.

Given the immediate clinical and research value of EBC-46 and its analogs, a practical and more sustainable solution to the supply problem would be realized through a time and step economical (Wender et al., *Acc. Chem. Res.* 48: 752-760 (2015)) semi-synthesis from a more available and diversified source (Wang & Hui *Org. Biomol. Chem.* 19: 3791-3812 (2021)). Similar strategies that combine the power of biological and chemical synthesis have enabled rapid access to other clinical candidates like Taxol and prostratin as well as their analogs (Wang & Hui *Org. Biomol. Chem.* 19: 3791-3812 (2021); Wender et al., *Acc. Chem. Res.* 41: 40-49 (2008); Kim et al., *J. Am. Chem. Soc.* 143: 16890-16901 (2021); Newman et al., *J. Nat. Prod.* 83: 770-803 (2020); Liu et al., *RSC Adv.* 6: 48800-48809 (2016)).

Toward this end, phorbol esters represent potential precursors to EBC-46. While available through total synthesis (Wender et al., *J. Am. Chem. Soc.* 119: 7897-7898 (1997); Lee & Cha *J. Am. Chem. Soc.* 123: 5590-5591 (2001); Kawamura et al., *Nature* 532: 90-93 (2016)), they are more readily accessed from more than 7000 species of the globally distributed Euphorbiaceae and Thymeaeceae plant families (Wang et al., *Chem. Rev.* 115: 2975-3011 (2015)). While plant cultivars vary in phorbol ester content, the seeds of the Croton tiglium plant of the Euphorbiaceae family supply upwards of 1.6% w/w of phorbol (2) upon extraction and ester hydrolysis (Ahmed & Salimon *Eur. J. Sci. Res.* 31: 429-436 (2009)).

Given the low cost (ca. $40/kg) of these seeds and the diverse geographical distribution of their varied sources, a synthetic route to EBC-46 according to the disclosure and based on phorbol (2) as the starting material (FIG. 1) has now been developed. To obtain this material a scalable isolation protocol building on prior work (Pagani et al., *J. Org. Chem.* 13: 1361-1367 (2017); Zimmermann & Franzyk *J. Nat. Prod.* 81: 2134-2137 (2018)) was developed that, on average, afforded greater than 10 grams of phorbol (2) from 3 kg of seeds. This isolation protocol consists of grinding the seeds and base-mediated removal of the C20, C12, and C13 esters in the extract to produce an oil from which phorbol (2) is purified by column chromatography.

Figure 2A:
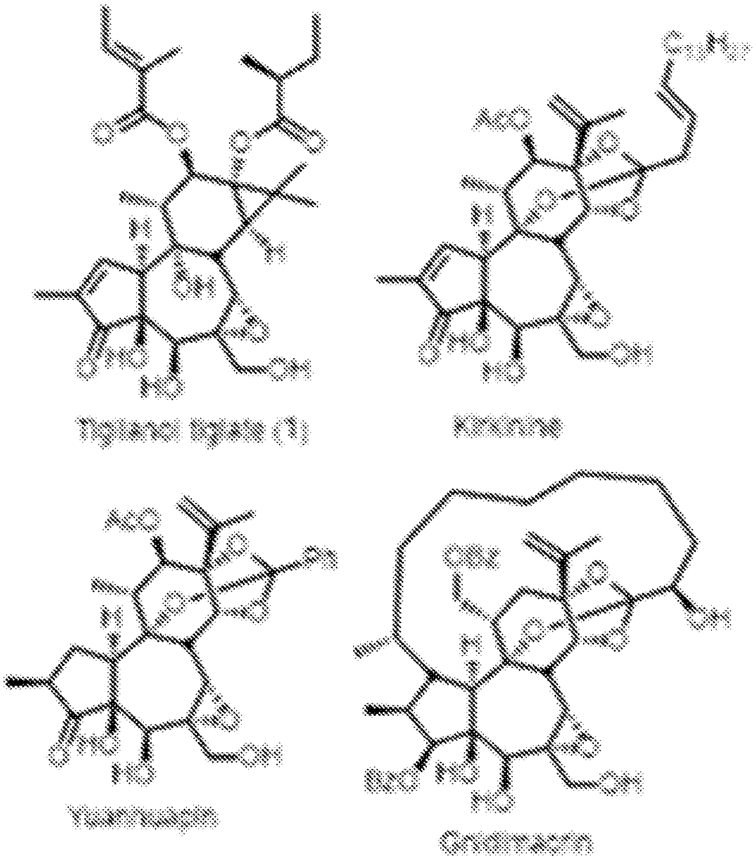
FIGS. 2A and 2B illustrate related tiglianes and daphnanes and 3D model of pharmacophore binding PKC.
Figure 2B:
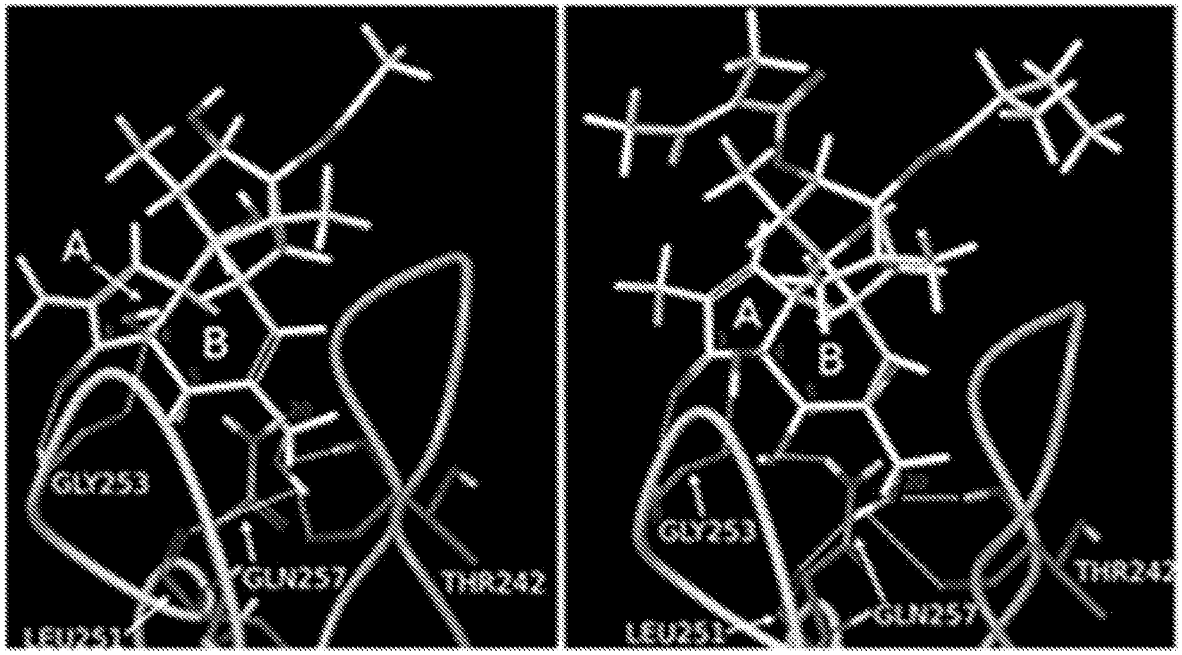

A key challenge associated with synthetically accessing EBC-46 and many related, biologically active tigliane and daphnane natural products is construction of their common B-ring 5β-hydroxy-6α,7α-epoxy functionality (FIG. 2A) (Wang et al., *Chem. Rev.* 115: 2975-3011 (2015); Hou et al., *Chinese Herbal Meds.* 13: 145-156. (2021)). Based on a pharmacophore model, this functionality, among other B-ring functional groups, was expected to influence PKC affinity, selectivity, and function (FIG. 2B) (Zhang et al., *Cell,* 81: 917-924 (1995); Wender et al., *Natural Products in Medicinal Chemistry* (Wiley-VCH Verlag GmbH & Co. KGaA: Weinheim), 475-544 (2014)). Thus, the core of this problem is oxy-functionalization of the 3-05 allylic hydrogen in the presence of activated allylic hydrogens at C8, C20, and other oxidizable functional groups (e.g., C10 and C19).

Phorbol has sensitivity to heat, light, acid, base, and air oxidation (Schmidt et al., *Cancer Res.* 35: 1375-1377 (1994)). Attempts at direct CH activation at C5 have thus far failed (Zimmermann & Franzyk *J. Nat. Prod.* 81: 2134-2137 (2018); Amin et al., *Fitoterapia* 148: 104802 (2021)). With a scalable source of phorbol (2) in hand, however, provided is a protocol that in one embodiment comprises six steps resulting in a highly diversifiable intermediate 7 from which EBC-46 and new analogs are readily derived.

Figure 3:
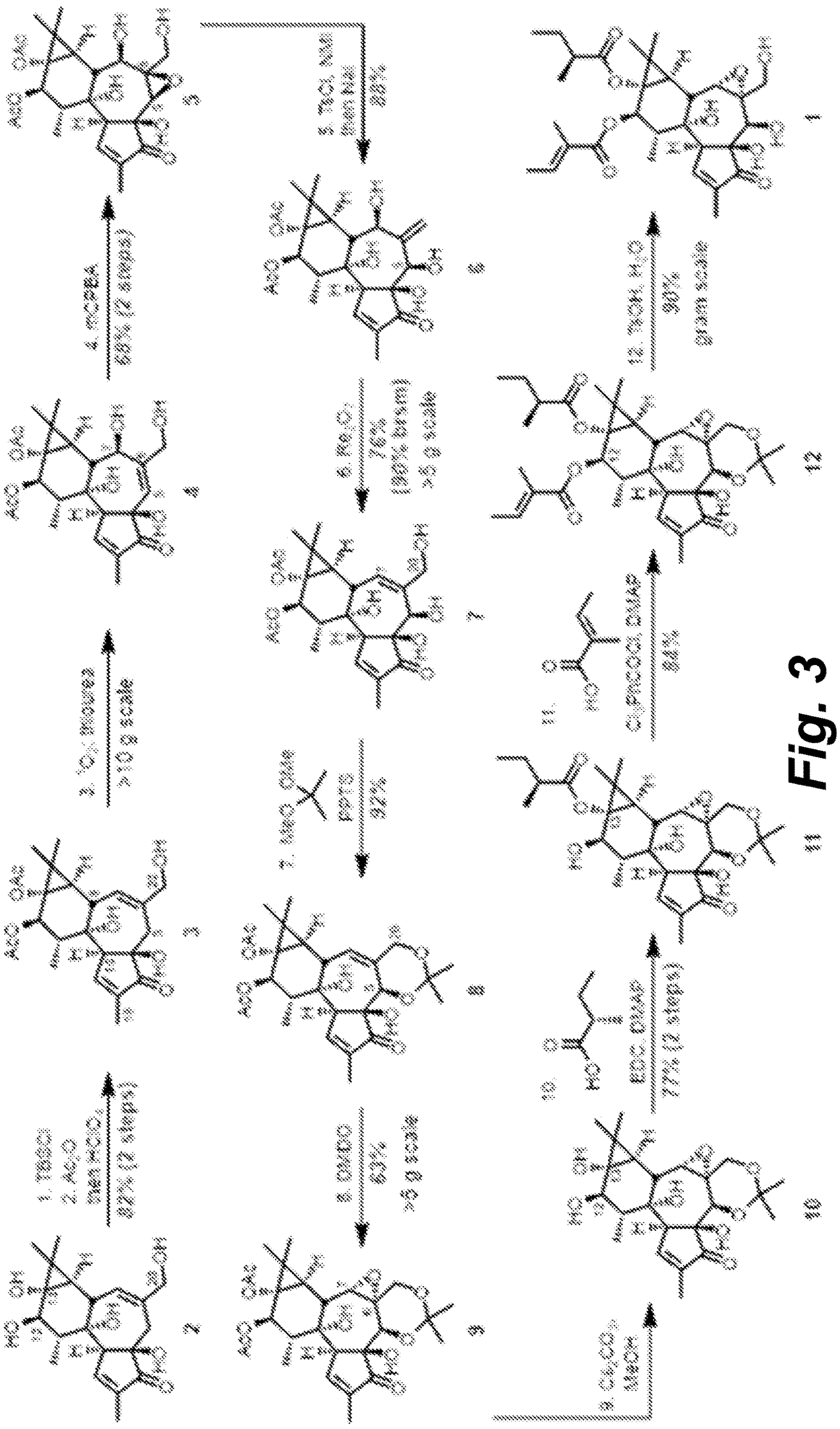
FIG. 3 illustrates a synthetic scheme of phorbol to tigilanol tiglate (the reaction sequence from phorbol (2) to tigilanol tiglate (1)). Reagents and conditions: 1. tert-butyldimethylsilyl chloride (TBSCl) (7 equiv), imidazole (15 equiv), dimethylformamide (DMF), 0° C.; 2. Acetic anhydride ($Ac_2O$) (15 equiv), triethylamine ($NEt_3$) (15 equiv), 4-dimethylaminopyridine (DMAP) (0.3 equiv), $CH_2Cl_2$; then MeOH, 0° C. to room temperature; then $HClO_4$ (25 equiv); 3. Rose bengal (1.5 mM), $O_2$, $CD_3OD$, 20° C.; then thiourea (3 equiv); 4, m-chloroperbenzoic acid (mCPBA) (2 equiv), 3:1 $CH_2Cl_2$:ether, 4° C.; 5. p-toluenesulfonyl chloride (TsCl) (1.2 equiv), N-methylimidazole (NMI) (0.1 equiv), $NEt_3$ (1.5 equiv), acetonitrile (MeCN), 0° C.; then $H_2O$; then sodium iodide (NaI) (3 equiv), 60° C.; 6. Rhenium(VII) oxide ($Re_2O_7$), (0.10 equiv), tetrahydrofuran (THF), 4° C.; 7. 2,2-dimethoxypropane (DMP) (300 equiv), pyridinium p-toluenesulfonate (PPTS) (0.15 equiv), acetone; then rotovap.; then acetone; 8. Dimethyldioxirane (DMDO) (3 equiv), acetone; 9. Cesium carbonate ($Cs_2CO_3$) in methanol (pH=11); 10. (S)-2-methylbutanoic acid (3 equiv), 1-ethyl-3-(3-dimethylaminopropyl)carbodiimide (EDC) (3.15 equiv), $NEt_3$ (3.30 equiv), DMAP (0.2 equiv), $CH_2Cl_2$; 11. Tiglic acid (2.2 equiv), 2,4,6-trichlorobenzoyl chloride (Yamaguchi reagent) (2 equiv), $NEt_3$ (4 equiv), DMAP (2.6 equiv), toluene; 12. p-toluenesulfonic acid in water (1 M), MeCN.

Anticipating that esters at C12 and C13 could be exchanged by late-stage diversification and would minimize interference with B-ring modifications, the first example started with a simple diacetate 3, which is prepared from phorbol (2), in 82% yield via t-butyldimethylsilyl (TBS) protection at C20 followed by acetylation at C12 and C13 and desilylative workup (FIG. 3).

Chemo-, regio- and stereo-selective oxidation at C5 of diacetate 3 in the presence of potentially oxidizable allylic sites at C8, C10, C19 and C20 was efficiently realized using a photosensitized singlet oxygen ene reaction with Rose bengal as a photosensitizer, green LEDs ($\lambda$=535 nm) as the photon source (Ghogare & Greer *Chem. Rev.* 116: 9994-10034 (2016); Sagadevan et al., *Nat. Commun.* 8: 1-8 (2017)), and d4-methanol as the solvent which minimizes singlet oxygen destruction (Sagadevan et al., *Nat. Commun.* 8: 1-8 (2017)). In situ reduction of the resultant hydroperoxide initially produced allylic alcohol 4 in moderate yield (66%). While this reaction can be routinely performed batch-wise on small scales (<500 mg), large scale batch reactions suffered from light penetration issues and raised concerns about accumulation of the potentially unstable hydroperoxide intermediate (Ghogare & Greer *Chem. Rev.* 116: 9994-10034 (2016)).

To address these scalability problems, a cyclic flow photoreactor utilizing a peristaltic pump and Tygon tubing was used (Levesque & Seeberger *Org. Lett.* 13: 5008-5011 (2011)). With this apparatus, the ene 4 was produced on a decagram scale (e.g., 19 grams) in 88% yield as determined by qNMR. While further purified for characterization purposes, this compound was sufficiently pure to be used directly in the following step thereby avoiding chromatographic purification.

It was envisioned that 4 could be converted to the C5 alcohols 6 or 7 via rhenium-catalyzed allylic transposition (Volchkov & Lee *Chem. Soc. Rev.* 43: 4384-4394 (2014); Morrill et al., *J. Org. Chem.* 71: 7813-7825 (2006)). However, reaction of 4 using literature conditions was sluggish and provided only minor amounts of the undesired C5α-hydroxy-C6,C20 alkene. As an effective alternative route to 6, it was found that epoxidation of the C5,C6 alkene in 4 with m-chloroperbenzoic acid (mCPBA) proceeded preferentially from the sterically more accessible β-face to give epoxide 5, with the desired C5β-O bond, in 77% yield. N-methylimidazole catalyzed chemo-selective tosylation of the primary C20 alcohol and subsequent reaction with sodium iodide gave exclusively the desired β-C5 alcohol 6 in 88% yield (Ferrier & Hall *J. Chem. Soc. Perkin Trans.* 1: 3029-3034 (1992)).

Upon treatment with catalytic $Re_2O_7$, the bis-allylic alcohol 6 underwent a highly chemo-selective 1,3-allylic alcohol transposition (Volchkov & Lee *Chem. Soc. Rev.* 43: 4384-4394 (2014); Morrill et al., *J. Org. Chem.* 71: 7813-7825 (2006)) affording C5β-hydroxy phorbol diacetate 7 in 76% yield (90% based on recovered 6), which serves as a diversification node (Wender et al., *Acc. Chem. Res.* 48: 752-760 (2015); Kim et al., *J. Am. Chem. Soc.* 143: 16890-16901 (2021)) for accessing unexplored B-ring analogs of 1. Other rhenium catalysts led to complex mixtures or lower conversion (Table 1).

Subsequent epoxidation of the C6,C7 alkene of 7 occurred only on the sterically more accessible and undesired β-face, as expected from earlier work (Wender et al., *Nat. Chem.* 3:615-619(2011); Boudreault et al., *Tetrahedron Lett.* 56: 3423-3427 (2015)). However, the facial selectivity exhibited by 7 can be reversed by conversion of 7 to its acetonide 8 (92%). Additionally, this protection of the C5 and C20 alcohols served to simplify subsequent functionalization of the C12 and C13 alcohols.

While initial epoxidation of acetonide 8 with mCPBA under a variety of conditions (Table 2) was slow and low yielding, treatment with the sterically smaller and more reactive dimethyl dioxirane (DMDO) stereoselectively gave α-epoxide 9 in 63% yield. This substrate-controlled facially selective epoxidation is unprecedented for this class of compounds and thus provides a potentially general method to access other structurally similar and biologically active tigliane and daphnane diterpenoids) Wang et al., *Chem. Rev.* 115: 2975-3011 (2015); Hou et al., *Chinese Herbal Meds.* 13: 145-156. (2021)).

Deacetylation of diester 9 provided the corresponding C12,C13 diol 10 in 86% yield as determined by qNMR. While further purified for characterization purposes, this compound was sufficiently pure to be used directly in the following step thereby avoiding chromatographic purification. Diol 10 serves as a second point of diversification for C12,C13 derivatization now with the desired C5β-hydroxy-C6α,C7α-epoxy B-ring in place (Cullen et al., *Sci. Rep.* 11: 1-14 (2021); Kim et al., *J. Am. Chem. Soc.* 143: 16890-16901 (2021); Wender et al., *Natural Products in Medicinal Chemistry* (Wiley-VCH Verlag GmbH & Co. KGaA: Weinheim), 475-544 (2014)). From 10, EBC-46 was prepared on gram-scale via selective diesterification (Johnson et al., *J.*

*Am. Chem. Soc.* 138: 6068-6073 (2016)) and acidic deprotection of the acetonide. In our laboratory, this overall route and greatly improved final esterification sequence has delivered over 2.5 grams of EBC-46. All steps were performed by two or more investigators to ensure reproducibility. Collectively, our synthetic strategy provides access to B-ring analogs from intermediate 7, A-ring analogs from intermediates 7-12, and C-ring analogs from intermediate 10.

Even modest structural changes dramatically affect PKC affinity and selectivity. To begin the investigation into the role of the C5β-hydroxy-C6α,C7α-epoxy functionality and the C12,C13 esters in determining PKC affinity and selectivity, a series of analogs was prepared (FIG. 4A). These novel analogs, along with EBC-46, were tested for their affinity to PKC-$\beta_I$ and PKC-θ, representative conventional and novel isoforms of PKC, respectively (FIG. 4B). Specifically, to determine the role of the C6α,C7α epoxide in PKC binding and selectivity, we synthesized a C6,C7-alkene analog (13, SUW400), otherwise inaccessible from EBC-46. Interestingly, this analog exhibits nearly identical binding affinity and selectivity to PKC-$\beta_I$ and PKC-θ when compared to EBC-46. This finding suggests that the C6α,C7α epoxide is not necessary for the isoform-selective binding exhibited by EBC-46.

Similarly, to determine the role of the C5β alcohol in PKC binding and selectivity, a C5-deoxy-C6,C7-alkene analog (15, SUW402) was synthesized. This analog shows stronger but less selective binding than both EBC-46 and SUW400. This finding suggests that the C5β alcohol plays an important role in isoform binding selectivity.

To begin investigating the role of the C12,C13 esters in PKC binding and selectivity, a diacetate analog (14, SUW401) was synthesized. This analog shows very low PKC binding affinity when compared to EBC-46. This finding suggests that the C12,C13 esters also play an important role in PKC binding.

Figure 4C:
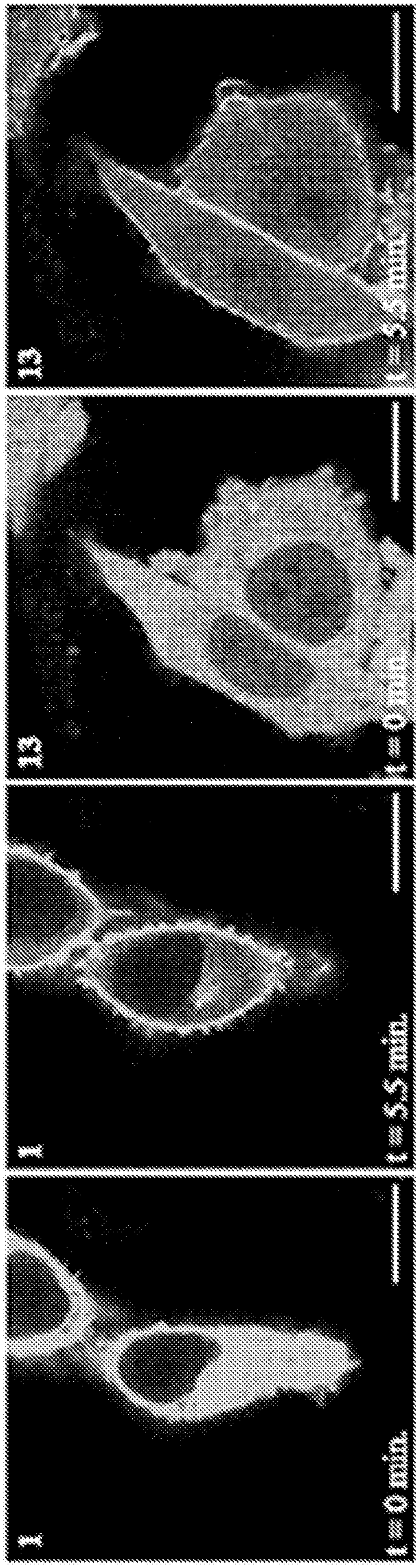
Figure 5:
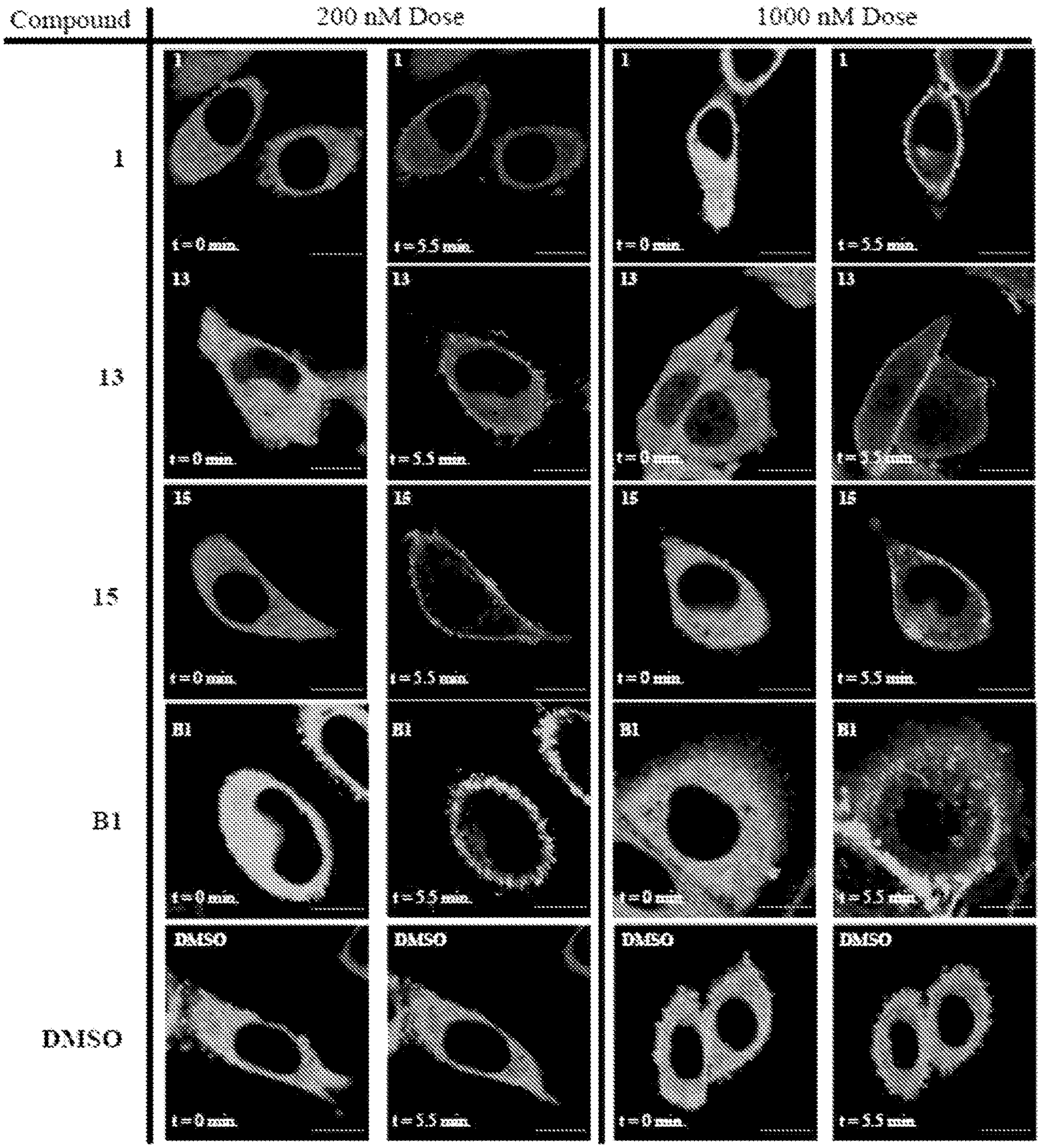
FIG. 5 illustrates the translocation of PKC-βI-GFP by tigilanol tiglate (1), SUW400 (13), and SUW402 (15) dosed at 200 nM (left panels) and 1000 nM (right panels) in CHO-K1 cells. Scale bars represent 10 μm. Bryostatin 1 (B1), a known PKC modulator, was used as a positive control and DMSO was used as a negative control.

Given the potent PKC affinity of EBC-46, SUW400, and SUW402, these compounds were tested in vitro for their ability to permeate CHO-K1 cells and translocate, in real time, an optically tagged PKC fusion protein (PKC-GFP) from the cytosol to the membrane—the hallmark of PKC activation (FIG. 5). Thus, EBC-46 showed modest translocation of PKC-$\beta_I$-GFP at low (200 nM) concentrations and robust translocation at high (1000 nM) (FIG. 4C). However, the more synthetically accessible SUW400 and SUW402 showed comparable translocation to EBC-46 at low (200 nM) as well as high (1000 nM) concentrations.

Accordingly, the present disclosure provides embodiments of a scalable laboratory preparation of tigilanol tiglate (1, EBC-46), an approved veterinary therapeutic and a human clinical lead for cancer and other indications. Previously, tigilanol tiglate was considered synthetically inaccessible and only available from a limited natural source, the latter raising environmental concerns. The synthetic strategy also enables, for the first time, access to numerous biologically active tiglianes, daphnanes and their novel analogs. This strategy will advantageous for determining the structural basis for PKC isoform selectivity and its role in mode of action and disease-specific activities.

One aspect of the disclosure encompasses embodiments of a method for the synthesis of tigilanol tiglate, the method comprising the steps as shown in the schema shown in FIG. 3 of the disclosure.

Another aspect of the disclosure encompasses embodiments of a method for the synthesis of tigilanol tiglate, the method comprising the steps as shown in the schema shown in FIG. 3 of the disclosure.

Yet another aspect of the disclosure encompasses embodiments of a method of isolating Phorbol (2) from Croton tiglium seeds, the method comprising the steps of: (a) pulverizing Croton tiglium seeds; (b) extracting the pulverized seeds by refluxing with methanol and concentrating the product thereof to an oil; (c) extracting the oil with a plurality of methanol washes and pooling the methanol washes; (d) adding cesium carbonate to the methanol washes with prolonged stirring; (e) acidifying the product of the preceding step with 6M sulfuric acid to a pH of 5.5; (f) filtering the acidified product and concentrating the filtrate therefrom under reduced pressure at 30° C.; (g) saturating the aqueous suspension from step (f) sodium chloride; (h) washing the aqueous phase with diethyl ether; and (i) extracting the diethyl ether with tetrahydrofuran (THF) and concentrating the THF extract under reduced pressure at 30° C.; drying the THF extract concentrate and purifying by silica gel vacuum column chromatography.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Synthetic efforts began with trigowiin A (4, FIG. 6), a tigliane diterpenoid isolated from a Vietnamese plant species, *Trigonostemon howii*, because this compound possesses moderate antiviral activity against chikungunya virus (CHKV). Given the structural similarity between trigowiin A and phorbol esters, and with the established pharmacophore for binding between phorbol esters and the C1 domain of PKC, development of trigowiin A and its analogs starting from phorbol was started. A protocol was modified and developed for producing phorbol starting from cheap Croton tiglium seeds. Croton tiglium seeds were ground, and the phorbol ester content was extracted via Soxhlet extraction with methanol. This extraction method minimized the presence of the glyceride contaminant that, upon saponification, would otherwise produce glycerol that coelutes with phorbol in the final purification step. The methanolic solution of phorbol esters was then degassed and immediately subjected to saponification with $Ba(OH)_2$ with carefully controlled pH (under 13) to limit the formation of 4α-phorbol, a base-induced rearrangement product from phorbol. This protocol allowed rapid production of gram quantities of phorbol for further synthetic development while saving time and cost of solvents compared to previously reported protocols. On average, it was possible to produce ca. 7.5 g of phorbol from 1.5 kg of seeds, consistent with the reported yield (1.2 g of phorbol per 100 mL of croton oil, equivalent to 200 g of Croton tiglium seeds) by Appendino and coworkers, and twice as high as the yield reported by Zimmerman and coworkers (3.5 g of phorbol per 1.5 kg of Croton tiglium seeds).

Figure 6:
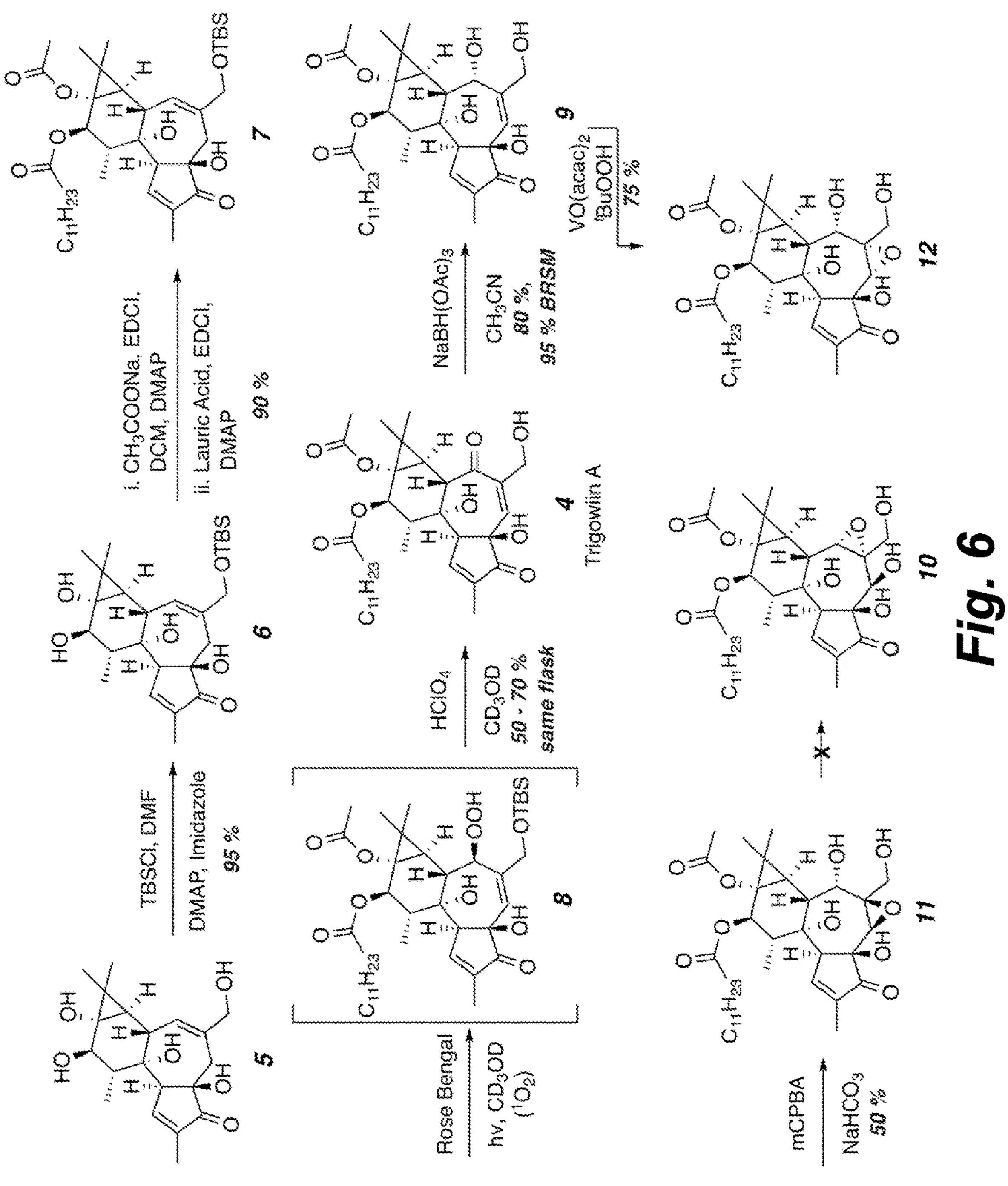
FIG. 6 illustrates the semi-synthesis of trigowiin A (4) and the first attempt to synthesize the 5β-hydroxy-6α,7α-epoxy system (10).

Having phorbol in hand, the primary alcohol at C20 was protected using tert-butyldimethyl silyl chloride (TBSCl) and dimethylformamide (DMF) to afford TBS-protected phorbol 6 in 90-95% yield (FIG. 6). From here, the unique reactivity of the C13-hydroxy over that of C12 was leveraged to perform sequential esterification on C13 followed by C12 in one flask via EDCI coupling reaction, yielding bis-ester 7 in 90% yield. Strategically, singlet oxygen allylic oxidation would lead to transposition of the alkene at C6,C7 to the C5,C6 positions as well as oxygenation at C7. Rose Bengal in d4-methanol gave the highest yield in the shortest time to produce hydroperoxide 8 in near quantitative yield. Hydroperoxide 8 was stable even at room temperature. Hydroperoxide 8 was treated with 2 equivalents of $HClO_4$, and trigowiin A (4) was produced in 50-70% yield as a result of acidic deprotection of the C20-silyl ether moiety and elimination to form the C7-enone. Trigowiin A binds with PKC β and PKC δ at 19.3 and 20.3 nM, respectively.

As trigowiin A (4) can be produced quickly in three steps from phorbol with an overall yield of 41 to 57% yield, derivatization strategies for preparation of both novel and naturally occurring tigliane analogs were devised. Under sodium borohydride ($NaBH_4$) reduction of 4 in methanol, the C7-enone moiety was selectively reduced to give C7-α-hydroxy 9. However, the A-ring enone would also rapidly undergo reduction, leading to variable yield of 9. Under a modified Evans-Saksena reduction protocol, compound 9 could be produced cleanly as a single product with sodium triacetoxyborohydride ($NaBH(OAC)_3$) with 80% yield, 95% yield BRSM. • Epoxidation with mCPBA afforded epoxide 11 in an unoptimized 50% yield. Structurally, epoxide 11 shares the same oxidation state in the B ring as tigilanol tiglate. There was a possibility of forming the 5β-hydroxy-6α,7α-epoxy system in compound 10 as this moiety is shared with a variety of tigliane and daphnane congeners, and more importantly, tigilanol tiglate (1).

A Payne rearrangement was attempted, but β-epoxide 11 was resistant to acidic ($pTsOH·H_2O$, $Ti(^iOPr)_4$ etc.) conditions, and unstable under basic protic conditions (DBU, $BnNMe_3OH$, etc.). Synthesis of yuanhuapin analogs indicated that C5,C6-alkenes on related structures were prone to form a bicyclic ether from the C9-hydroxy functionality under metal-catalyzed epoxidation conditions. Tigilanol tiglate (1) can spontaneously undergo Payne rearrangement to EBC-211 upon incubation in neutral aqueous media. 5β-hydroxy-phorbol esters 13 represented attractive precursors for subsequent stereoselective epoxidation at C6,C7. Selenium dioxide oxidation of 7 or other protecting groups at the C20-hydroxyl group slowly led to oxidation at C20. A relay oxidation sequence was laid out in FIG. 7 for C5-hydroxylation of phorbol esters at C5.

Figure 7:
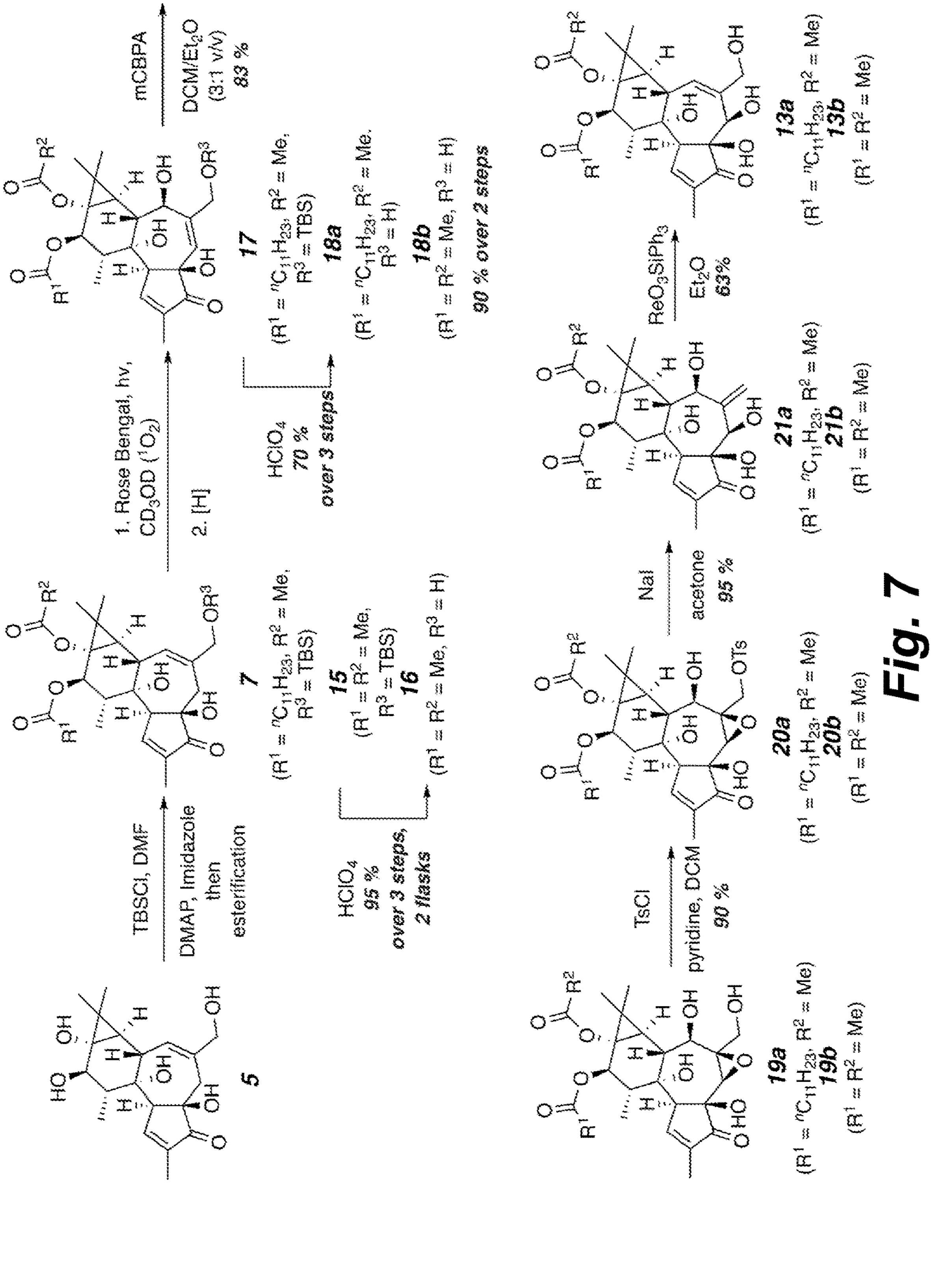
FIG. 7 illustrates a synthetic route toward 5β-hydroxy phorbol precursors 13, setting the stage for installation of stereoselective epoxidation.

Throughout the synthetic route laid out in FIG. 7 for both 12-laurate-13-acetate and 12,13-diacetate intermediates, no difference in reactivity was seen except for the expected change in polarity of the resulting intermediates. While in following the route in FIG. 5 compound 7 was obtained in two separate operations. In the scale up effort phorbol 12,13-diacetate (16) was produced in 95% yield in two steps, with no intermediate purification. This was done by subjecting the crude to excess acetic anhydride diesterification following workup of the TBS-protection step, and then quenching with methanol and acidic desilylation using $HClO_4$. It was possible to obtain pure phorbol diacetate 16 in a very short amount of time only at the expense of one chromatographic purification at the end. Both silyl protected phorbol esters 7 and phorbol diacetate 16 can undergo singlet oxygen photooxygenation efficiently to produce 17 and 18b, respectively. Upon scale up, batchwise photosensitized singlet oxygen reaction was challenging due to light penetration issues. To solve that problem, a flow apparatus was used that allowed reproducible conversion from diacetate 16 to diacetate 18b in highly concentrated solutions (ca. 1.0 M). In this manner, 18b was produced in close to 90% yield based on recovery of starting material with minimal usage of d4-methanol, an expensive solvent. In the same flask, upon reduction with triphenyl phosphine ($PPh_3$), desilylation of 17 to 18a can be achieved in 70% by addition of $HClO_4$. Triphenyl phosphine oxide byproduct was challenging to remove from diacetate 18b. Therefore, thiourea was used as an alternative reductant to produce 18b in 90% yield. Photobleached Rose Bengal byproducts often contaminate 18b, and are not easily separated by one chromatographic operation. Treatment with activated charcoal prior to chromatography completely removes the aromatic byproducts from decomposition of Rose Bengal in the singlet oxygen chemistry. Epoxidation of the C5,C6-alkene 18a/b was achieved by mCPBA to afford 19a/b in 83% yield. Subsequently, the primary alcohol at 020 was tosylated selectively to afford 20a/20b in 90% yield. Upon heating tosylate 20a/b in acetone with excess sodium iodide (30 eq), the reductive epoxide ring opening occurred spontaneously to afford exoolefin 21a/b in 95% yield. Having exocyclic olefin 21a/b in hand, 1,3-allylic alcohol transposition was attempted using $ReO_3SiPh_3$ as a catalyst to afford the desired 5β-hydroxyphorbol esters 13a/b in 63% yield. the first time that a 1,3-allylic alcohol transposition via $ReO_3(OSiPh_3)$ can be done selectively on such complicated polyol substrates like 21 alb.

Figure 8A:
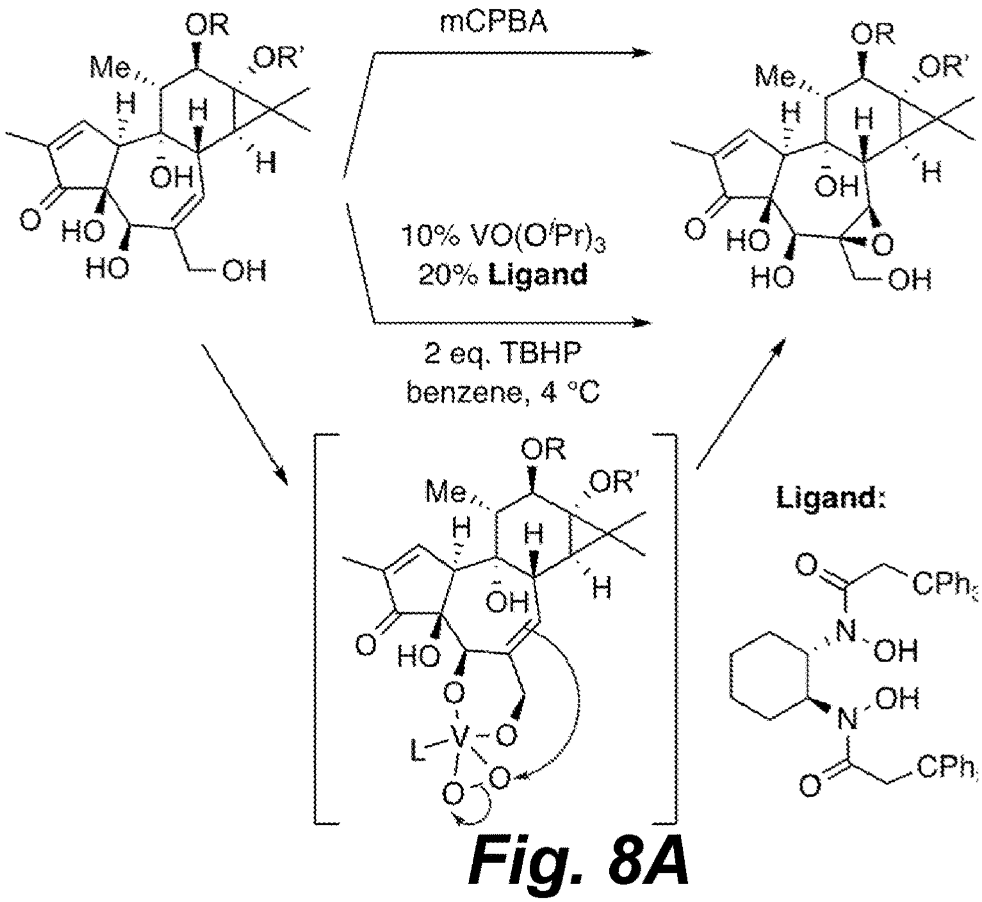
FIG. 8A illustrates attempts to produce α-epoxide via modified Yamamoto's asymmetric allylic epoxidation.
Figure 8B:
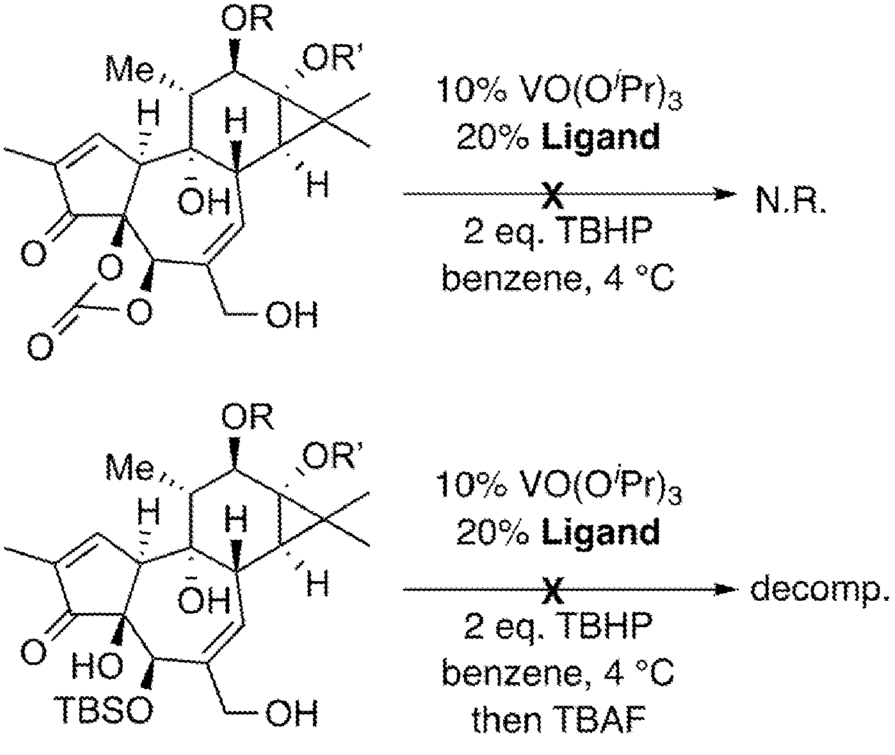
FIG. 8B illustrates attempts to produce α-epoxide via modified Yamamoto's asymmetric allylic epoxidation on protected C5-hydroxy.

Delivering the epoxide to the α face of 13a/b was non-trivial (FIGS. 8A and 8B). Substrate-controlled mCPBA epoxidation gave exclusively the β-epoxide. Modified Yamamoto's delivered the α-epoxide on phorbol diesters with 89:11 dr, the vanadium-based epoxidation chemistry on compounds of type 13a/b afforded the 3-epoxide as the sole product.

It was hypothesized that the 5,20-dial moiety chelated with the 4,5-cyclic carbonate and shut down the reactivity, possibly due to a remarkable conformational change, while the C5-silyl ether gave rise to an inseparable mixture of products that underwent decomposition upon TBAF deprotection. Therefore, the 5,20-diol functionality in 13a/b was protected with 2,2-dimethoxypropane (FIGS. 7A and 7B) so that the resulting cyclic acetonide 22a/22b would create a steric sphere on the β-face, which in turn would encourage the formation of the α-epoxide. The first attempt of epoxidation on 22a with 2 equivalents of mCPBA did not proceed upon 24 hours of stirring. Upon forcing conditions with 30 equivalents of mCPBA, it was possible to isolate, in modest yield, the desired α-epoxide 23a as the only identifiable product.

Dimethyl dioxirane (DMDO) epoxidation was explored as an alternative for scalability, environmental and safety amenability. The reaction by NMR in $CDCl_3$ was first monitored with 1 equivalent of DMDO (0.095 M in acetone), and the desired product 23a was formed in 30% yield, along with competitive formation of aldehyde 24 (5%) and recovery of starting material (50%). When the desired epoxidation in sole acetone was slower than the decomposition pathway, when the reaction in a 3:1 v/v $CHCl_3$/acetone solvent system with 3 equivalents of DMDO (0.095 M in acetone) was performed, the α-epoxide 23a was obtained cleanly and selectively in 95% yield in 6-8 hours, with no detection of the undesired 3-epoxide 26. This substrate-controlled α-selective epoxidation at the C6,C7-olefin on tigliane scaffolds is unprecedented.

Figure 9A:
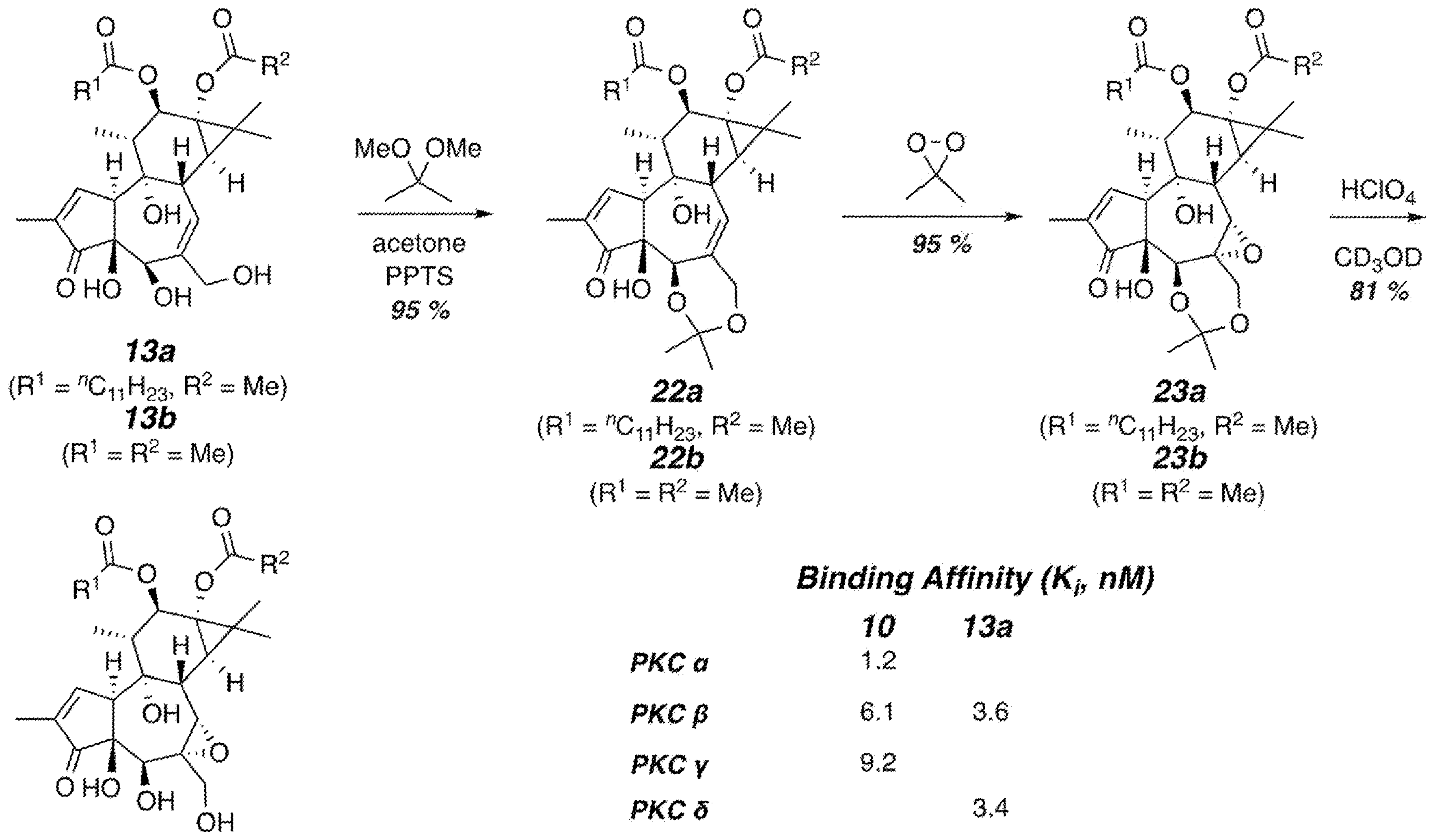
Figure 9B:
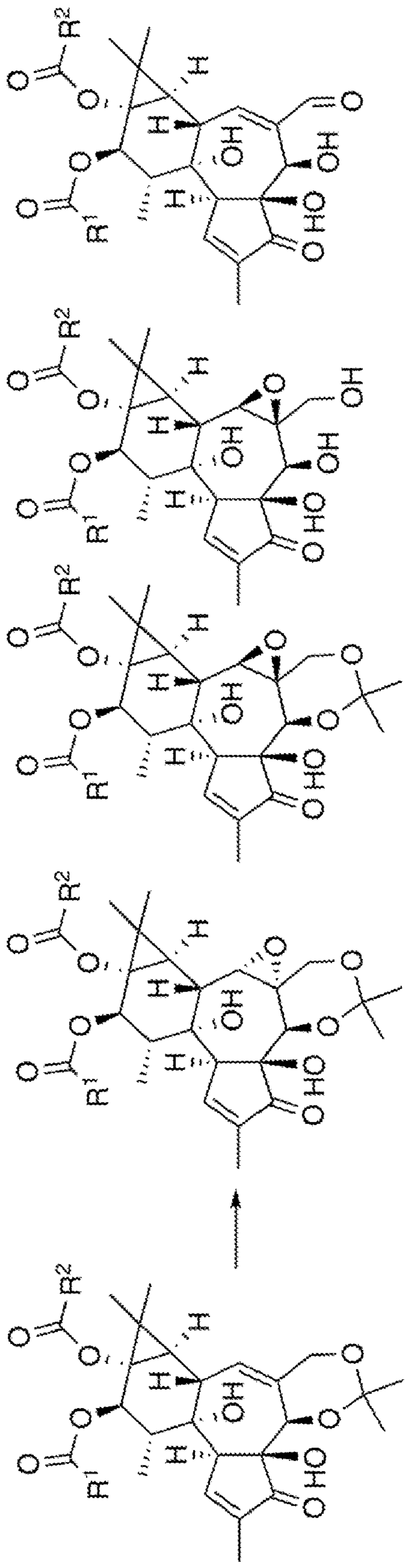
FIG. 9B illustrates an optimization for DMDO epoxidation.

Having α-epoxide 23a in hand, the deprotection of cyclic acetonide using $HClO_4$ in $CD_3OD$ was monitored by NMR to produce 5β-hydroxy-6α,7α-epoxy 10 in 81% yield. Compound 13a and its epoxide 10 were comparatively assessed in a cell-free PKC binding assay, and they were both potent PKC binders in conventional and novel isoforms (FIG. 9A).

Figure 10:
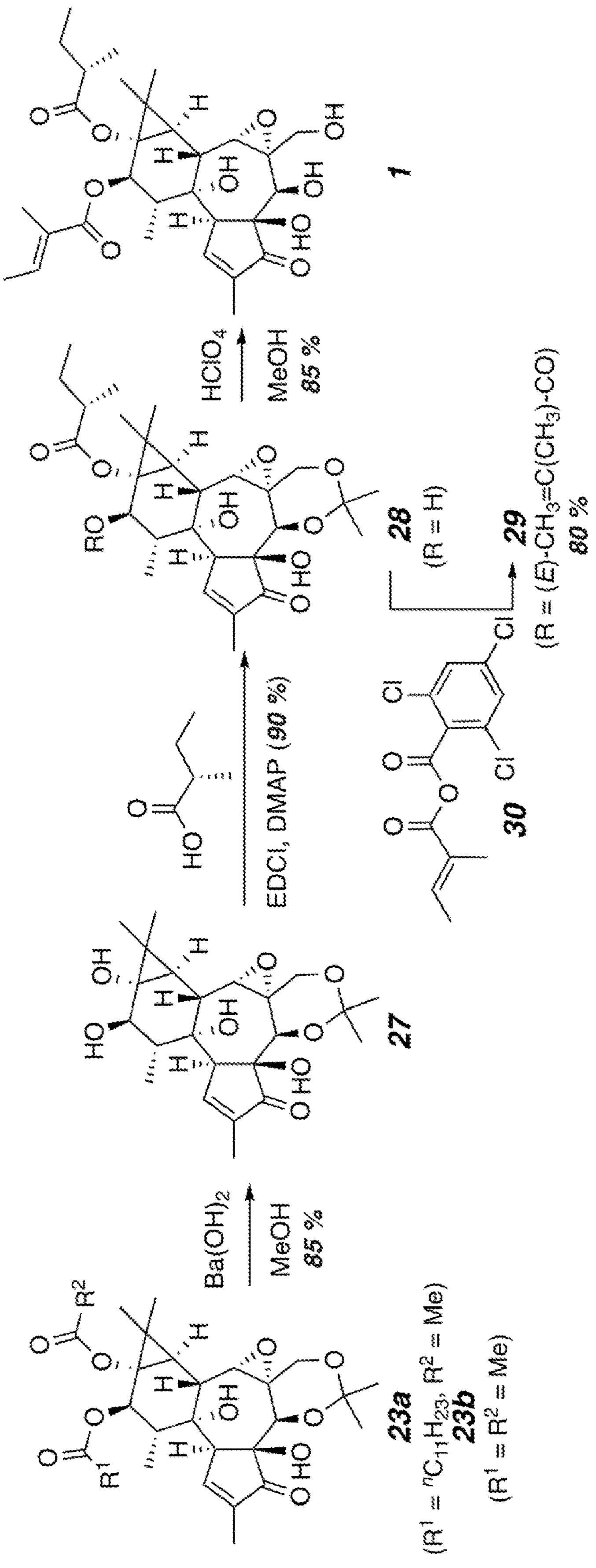
FIG. 10 illustrates efforts toward installation of tigilanol tiglate (EBC-46, 1) esters.

After the first laboratory preparation of a 5β-hydroxy-60, 70-epoxy on the tigliane scaffold had been established, synthetic efforts were scaled up for preparation of tiglianol tigliate (1) and analogs. 23a/b was subjected to saponification via $Ba(OH)_2$ in methanol to produce compound 27 in 85% yield (FIG. 10). While installation of (S)-methylbutanoate at C13 could be achieved via Steglich's EDCI conditions in near quantitative yield, the C12-hydroxy in 28 was inert to Steglich conditions even with multiple equivalents of tiglic acid, EDCI, and DMAP. One-flask Yamaguchi esterification produced bis-ester 29 in modest yield. Treatment of monoester 28 with mixed anhydride 30 yielded the desired bis-ester in 80% yield. Finally, deprotection of the resulting epoxyacetonide 29 in methanol using $HClO_4$ afforded tigilanol tiglate (1) in 85% yield.

Figure 11:
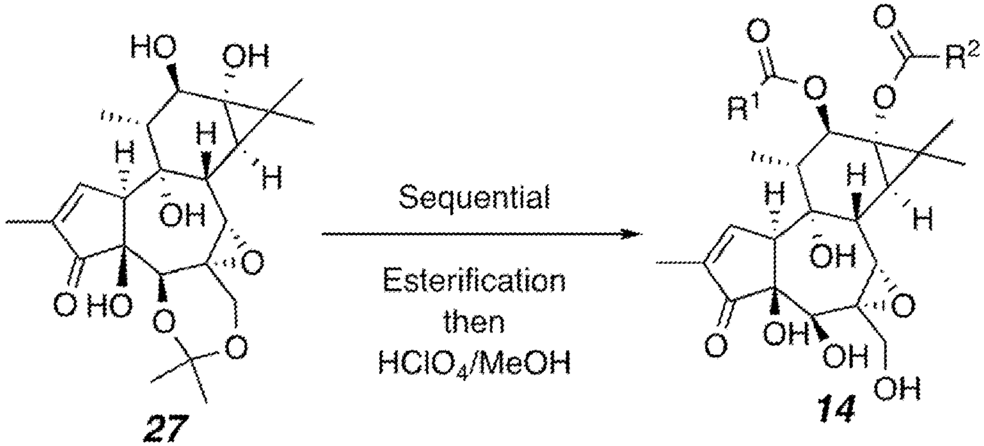
FIG. 11 illustrates the reparation of Analogs and Binding Assays.
Figure 12:
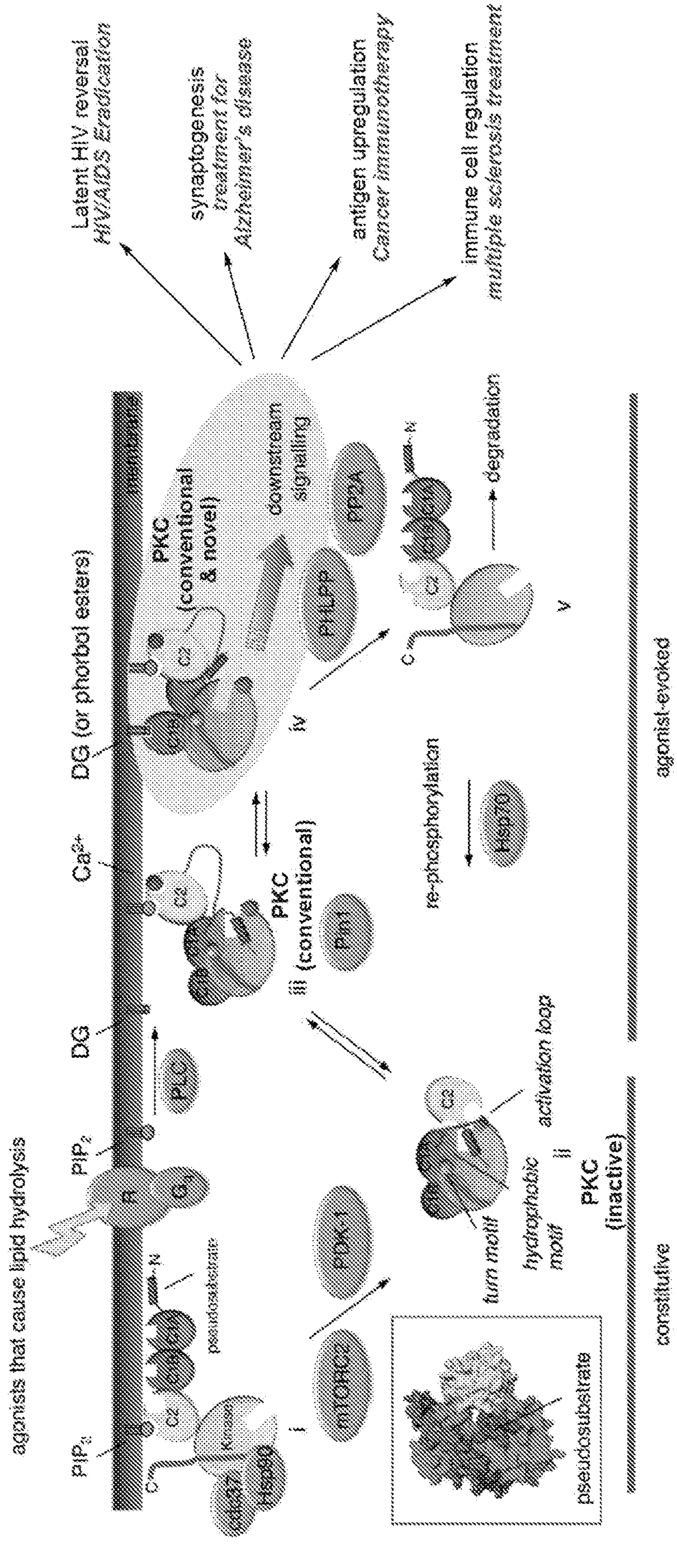
FIG. 12 illustrates Protein Kinase C (PKC) as a therapeutic target.
Figure 13:
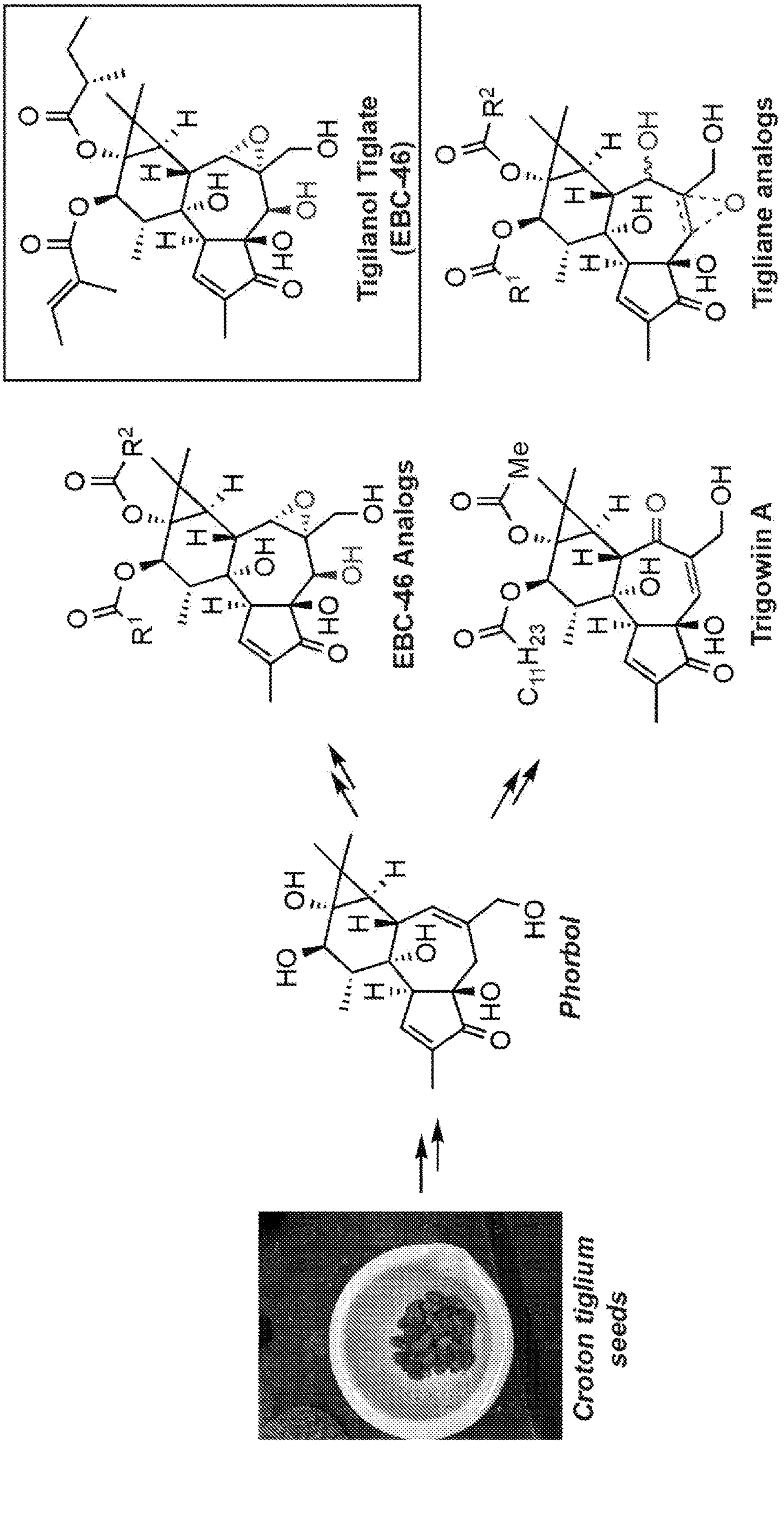
FIG. 13 illustrates Protein Kinase C modulators with diverse architecture

With intermediate 27 in hand, the same sequential esterification strategy was also used to generate and assay a variety of epoxytigliane 14 for their binding affinity to C1 domain of representative conventional and novel PKC isoforms (FIG. 11).

In summary, described is a laboratory preparation of tigilanol tiglate 1 from readily available phorbol from natural sources, including the installation of the 5-β-hydroxy-6, 7-α-epoxy B-ring oxidation pattern that provides a scalable gateway synthesis to functional analogs of tigilanol tiglate as well as other related, clinically relevant diterpenoids.

Example 2

All reactions were carried out in glassware under ambient atmosphere unless otherwise noted. Reactions were concentrated under reduced pressure using a rotary evaporator unless otherwise noted. Commercial reagents were used as received or purified using the methods indicated herein. Dichloromethane, diethyl ether, dimethylformamide, tetrahydrofuran, and toluene were passed through an alumina drying column (Solv-Tek Inc.) using nitrogen pressure; ethyl acetate and hexanes were obtained from Fisher Scientific. Analytical thin-layer chromatography (TLC) was carried out on 250 μm silica gel 60G plates with fluorescent indicator F254 (EMD Millipore). Plates were visualized with UV light and treated with p-anisaldehyde, ceric ammonium molybdate, or potassium permanganate stain with gentle heating. Flash column chromatography was performed using silica gel (230-400 mesh, grade 60, particle size 40 to 63 μm) purchased from Fischer Scientific. NMR spectra were acquired on a Varian INOVA 600 or Varian 400 or Bruker 400 magnetic resonance spectrometer. $^1H$ chemical shifts are reported relative to the residual solvent peak ($CDCl_3$=7.26 ppm, $d_6$-acetone=2.05 ppm, $CD_3OD$=3.31 ppm) as follows: chemical shift (δ), multiplicity (app=apparent, b=broad, s=singlet, d=doublet, t=triplet, q=quartet, m=multiplet, or combinations thereof), coupling constant(s) in Hz, integration. $^{13}C$ chemical shifts are reported relative to the residual solvent peak ($CDCl_3$=77.16 ppm, $d_6$-acetone=206.26 ppm, $CD_3OD$=49.00 ppm). Infrared spectra were acquired on a Nicolet IS 50 FT-IR Spectrometer (ThermoFisher) equipped with an attenuated total reflectance (ATR) assembly. Optical rotations were acquired on a P-2000 Digital Polarimeter (Jasco).

Experimental procedures were generally optimized on a small scale, and the results from these optimized procedures are provided below. Reaction procedures were performed by multiple investigators to ensure reproducibility. Characterization data is provided for all isolable compounds. For some steps, the reaction product could be used without chromatographic purification.

Example 3

Extraction and saponification of phorbol esters from Croton tiglium seeds: Chemicals: Croton seeds (Jamal Ghota, Herbalveda): used without purification MeOH (Fisher, low water): used without purification Cesium Carbonate (Chem Impex, 99.99%): used without purification Cesium Carbonate (AK scientific, 99.9%): used without purification. Phorbol (2) was isolated from Croton tiglium seeds according to the following protocol, adapted from previous isolation reports of phorbol (Pagani et al., *J. Org. Chem.* 13: 1361-1367 (2017); Zimmermann & Franzyk *J. Nat. Prod.* 81: 2134-2137 (2018)). Croton tiglium seeds (500 g) were pulverized in a coffee grinder and the resulting grounds were placed into a cellulose bag. The Soxhlet extractor was loaded with the croton seed grounds and a 2 L round-bottom flask was attached to the bottom. Methanol (1.0 L) was slowly poured through the top of the apparatus. The Soxhlet was fitted with a water-cooled condenser and the methanol in the 2 L collection flask was heated to reflux. After 15 hours at reflux, the collection flask was cooled to room temperature and its contents were concentrated to an oil and stored at 4° C. This process was repeated nine times for a total of 5 kg of seeds. The combined extracts were dispersed in methanol (2.0 L) and placed in a 4 L separatory funnel. The bottom layer was separated and washed with methanol (3×200 mL). The methanol layers were combined and transferred into a 5 L three-necked flask equipped with a mechanical stirring rod. Cesium carbonate (140 g, pH=11) was added portion wise, and the suspension was stirred at room temperature. After stirring for 18 hours, the reaction mixture was analyzed by TLC (15% MeOH/DCM) to confirm the presence of phorbol. 6 M $H_2SO_4$ was added to the reaction mixture until a pH of 5.5 was obtained. The mixture was filtered through a fritted funnel, and the filtrate was concentrated under reduced pressure at 30° C. The resulting oil was suspended in water (1.0 L). The headspace of the flask was flushed with nitrogen, and the flask was stored at 4° C. overnight.

The aqueous suspension was saturated with solid sodium chloride and decanted into a separatory funnel. The aqueous phase was washed with diethyl ether (3×500 mL) upon which TLC confirmed the removal of non-polar impurities (no phorbol present in the combined diethyl ether layers). The aqueous phase was extracted with THE (5×500 mL) or until TLC of the THF layer of the last extraction indicated the absence of phorbol (THF draws a significant amount of water to the organic layer). The combined THF layers were concentrated under reduced pressure at 30° C. To assist in removal of the residual water, the resulting oil was dispersed in absolute ethanol (5×300 mL) and concentrated again to afford a mixture of solid and oil. The mixture was dispersed in methanol (200 mL) and silica gel (200 g) was added. The mixture was concentrated under reduced pressure at 30° C. and dried under high vacuum overnight to afford free floating solid. Purification was accomplished by silica gel vacuum column chromatography (0-15% MeOH/DCM, 9×15 cm) affording phorbol (2) (0.32% w/w, 16.1 g) as a white foam (Note 1). Compound purity was established by TLC (one spot) analysis. Yield and mmol of phorbol isolated were determined by qNMR (dimethyl sulfone internal standard in $CD_3OD$ solvent).

TLC: Rf=0.35 (15% MeOH/DCM), UV active, green spot in p-anisaldehyde $^1$H-NMR: (400 MHz, $CD_3OD$) δ 7.61 (m, 1H), 5.60 (d, J=5.9, 1H), 4.05 (d, J=10.2 Hz, 1H), 3.94 (m, 2H), 3.16 (dd, J=5.7, 5.7 Hz, 1H), 3.09 (m, 1H), 2.57-2.39 (m, 2H), 1.94 (dq, J=10.1, 6.5 Hz, 1H), 1.75 (dd, J=3.0, 1.4 Hz, 3H), 1.26 (s, 3H), 1.14 (s, 3H), 1.07 (d, J=6.5 Hz, 3H), 0.73 (d, J=5.4 Hz, 1H)

$^{13}$C-NMR: (101 MHz, $CD_3OD$, 20 peaks total) δ 209.4, 159.9, 140.5, 132.9, 129.8, 80.7, 78.4, 73.5, 66.9, 61.8, 57.4, 44.8, 38.9, 37.2, 36.1, 25.7, 22.7, 16.4, 14.1, 8.8 The characterization data of the phorbol isolated using this procedure was identical to the previously reported characterization data of phorbol (Wender et al., *J. Am. Chem. Soc.* 119: 7897-7898 (1997); Lee & Cha *J. Am. Chem. Soc.* 123: 5590-5591 (2001); Kawamura et al., *Nature* 532: 90-93 (2016)).

Example 4

Steps 1-2: Conversion of Phorbol (2) to Phorbol Diacetate 3 (C12,C13 Acetate Protection)

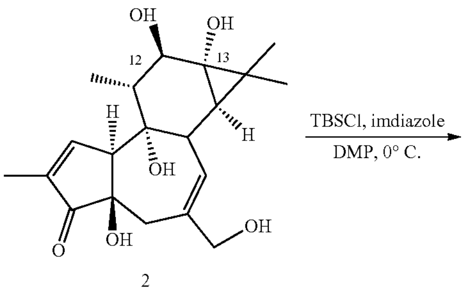

2

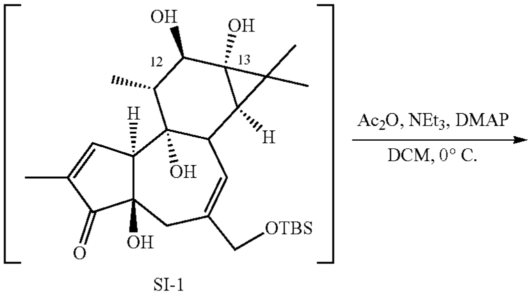

SI-1

-continued

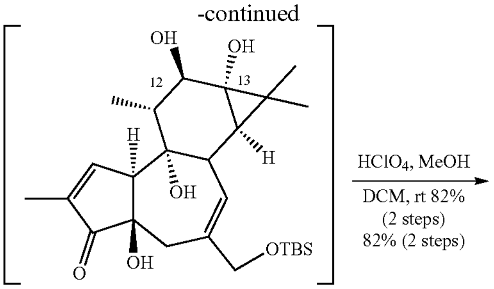

SI-2

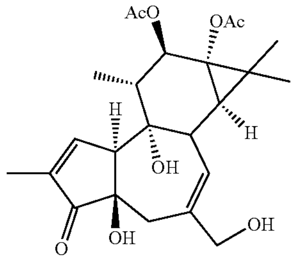

3

Chemicals: TBSCl (TCl, >98%): used without purification; Imidazole (Sigma-Aldrich, >99%): used without purification; Acetic anhydride (Fluka, >99%): used without purification; Triethylamine (Fisher, 99%): used without purification; DMAP (Oakwood): used without purification; $HClO_4$ (Baker, 70%): used without purification To a one-neck, 100 mL round-bottom flask equipped with a stir bar was added phorbol (2) (96.9 mg, 0.266 mmol, 1 equiv) in DMF (2 mL) via syringe. Imidazole (272 mg, 3.99 mmol, 15 equiv) was added directly to the solution while stirring. The homogeneous reaction mixture was cooled in an ice bath (0° C.) and stirred for 15 min. TBSCl (281 mg, 1.86 mmol, 7 equiv) was added directly to the solution while stirring. After stirring for 30 min, TLC analysis indicated complete conversion of 2 and formation of SI-1. The reaction was quenched by pouring directly into a 100 mL Erlenmeyer containing sat. $NH_4Cl$ (10 mL). The reaction mixture was transferred to a separatory funnel, diluted with brine (25 mL) and extracted with EtOAc (3×25 mL) until TLC of the aqueous layer no longer showed product. The combined organic layers were washed with brine (50 mL), dried over $Na_2SO_4$, filtered, and concentrated.

To the resulting crude oil was added DCM (5 mL), acetic anhydride (376 μL, 3.99 mmol, 15 equiv), and triethylamine (556 μL, 3.99 mmol, 15 equiv). The reaction mixture quickly became cloudy. DMAP (9.8 mg, 0.079 mmol, 0.3 equiv) was added directly while stirring and the reaction mixture quickly becomes homogeneous. After stirring for 1 hour at rt, TLC analysis indicated complete conversion of SI-1 and formation of SI-2. The reaction mixture was cooled with an ice bath (0° C.) and stirred for 15 min. MeOH (1 mL) was added via syringe over about 2 min. The reaction mixture was allowed to warm to rt then 70% w/w $HClO_4$ (571 μL, 6.65 mmol, 25 equiv) was added directly via syringe. After stirring for 1 hour at rt, TLC analysis indicated complete conversion of SI-2 and formation of product 3. The reaction was quenched over the course of 5 min with sat. $NaHCO_3$ (10 mL). The reaction mixture was transferred to a separatory funnel and extracted with DCM (3×25 mL) until TLC of the aqueous layer no longer showed product. The combined organic layers were dried over $Na_2SO_4$, filtered, and concentrated. Purification was accomplished by silica gel flash column chromatography (30-70% EtOAc/Hex, 2×15 cm) affording phorbol diacetate 3 (97.1 mg, 82%) as a white foam. Compound purity was established by TLC (one spot) analysis. Excess TBSCl was necessary due to the presence of alcohol impurities carried forward from the phorbol extraction process.

Insufficient washing at this stage resulted in DMF contamination in the final product. Note 3: On large scale, cooling prior to quenching is necessary for controlling the exotherm.

TLC: Rf=0.16 (50% EtOAc/Hex), UV active, green spot in p-anisaldehyde $[\alpha]^{23.20}D=+46.1°$ (c=0.84, $CH_2Cl_1$)

FTIR: (ATR) 3396 (br), 2924, 1705, 1627, 1372, 1327, 1260, 1230, 1140, 1077, 1059, 1018, 977, 944, 911, 890, 804, 734, 702, 617, 574 $cm^{-1}$ $^1$H-NMR: (400 MHz, $CDCl_3$) δ 7.56 (m, 1H), 5.66 (d, J=5.2 Hz, 1H), 5.56 (brs, 1H), 5.37 (d, J=10.4 Hz, 1H), 4.03 (d, J=12.9 Hz, 1H), 3.96 (d, J=13 Hz, 1H), 3.25-3.21 (m, 2H), 2.99 (s, 1H), 2.57 (d, J=18.1 Hz, 1H), 2.47 (d, J=18.1 Hz, 1H), 2.42 (brs, 1H), 2.14 (dq, J=10.3, 6.0 Hz, 1H), 2.07 (s, 3H), 2.06 (s, 3H), 1.74 (dd, J=1.3, 2.8 Hz, 1H), 1.23 (s, 3H), 1.21 (s, 3H), 1.08 (d, J=5.2 Hz, 1H), 0.87 (d, J=6.6 Hz, 1H)

$^{13}$C-NMR: (101 MHz, $CDCl_3$, 24 total peaks) δ 209.2, 173.9, 171.1, 160.9, 140.8, 133.0, 129.2, 78.4, 77.1, 73.8, 68.1, 65.7, 56.1, 43.0, 39.1, 38.6, 36.3, 25.0, 24.0, 21.2 (2C), 16.8, 14.5, 10.2

HRMS calculated for $C_{24}H_{32}NaO_8^+$ $[M+Na]^+$: 471.1989; found: 471.1984

Example 5

Step 3: Conversion of Phorbol Diacetate 3 to C7-Alcohol 4 (Installation of C7-OH)

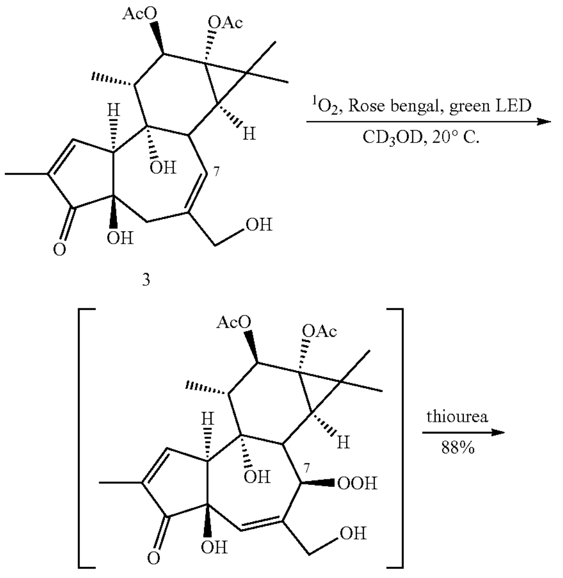

3

SI-3

-continued

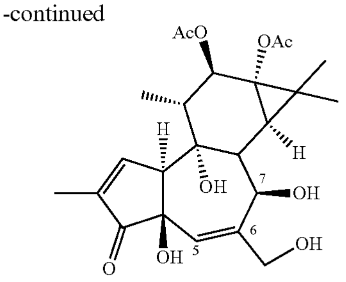

4

Chemicals: Rose Bengal (Sigma-Aldrich, 90%): used without purification; Thiourea (Sigma-Aldrich, >99%): used without purification; $CD_3OD$ (Cambridge Isotope Laboratories, 99.8%): used without purification; Charcoal (JT Baker): used without purification.

Batchwise Photo-Oxidation (Small Scale)

Reaction vessel: Green LED strip lights with an adhesive backing were wrapped around the inside of a 1.2 L crystallizing dish with the lights facing inward. Aluminum foil was fitted around the outside of the crystallizing dish to maximize light saturation. The LED lights were plugged in, and an air hose was fitted to circulate air within the reaction vessel.

Reaction setup: To an 8-dram vial equipped with a stir bar was added 3 (228 mg, 0.508 mmol, 1 equiv.) and Rose Bengal (52 mg, 0.051 mmol, 7.3 mM) followed by $CD_3OD$ (7 mL). The reaction vial was flushed with oxygen gas from a balloon then sealed with Teflon tape and parafilm. The reaction vial was placed into the reaction chamber and irradiated with 535 nm light for 24 hours, at which point TLC analysis indicated complete conversion to hydroperoxide intermediate SI-3. The reaction mixture was added to thiourea (116 mg, 1.52 mmol, 3 equiv) and sonicated for 15 minutes to ensure complete reduction of the hydroperoxide intermediate.

Example 6

Continuous Flow Photo-Oxidation:

Preparation of the unloaded photoreactor. A green LED strip (approximately 16 feet) was coiled around a 1 L Boston-style bottle. The LED-equipped bottle was secured in a one-gallon plastic bag to protect it from the water bath, and Tygon tubing [50 feet, (1/16" inner diameter and 1/8" outer diameter)] was coiled around the exterior of the bag leaving approximately 1' of extra tubing coming off of the top end and the remainder of the excess tubing coming off of the bottom end. This tubing was secured with one layer of parafilm. The tubing was not secured too tightly because it is compressible, and the effective volume of the reactor would be reduced if the tubing is compressed.

Organization of the apparatus: The photoreactor was placed inside of a 2 L beaker, and the beaker was filled with enough water to cover all the coils of tubing. An appropriately-sized (about 1/16th inch) male-to-male adapter was fit on to the peristaltic pump, and a separate 2' piece of the Tygon tubing was attached to the pump inlet. The excess tubing on the bottom of the photoreactor was attached to the pump outlet, and the pump was placed in a centralized location.

Attachment of the oxygen source: A balloon was fixed to a regulator and filled with 02. The regulator was closed, and the outlet was equipped with a 25-gauge needle. This apparatus was mounted above the pump inlet. A 2" section of the inlet tubing was braced with a glass test tube and parafilm, and the needle of the balloon was carefully inserted into the braced tubing such that the needle was pointing towards the pump and the bevel of the tip was facing towards the wall of the tubing. The needle of the oxygen balloon was secured to the inlet tubing with Teflon tape.

Pointing the needle in the direction of the pump minimized the flow rate needed to move solvent through the system. The brace protected the inlet tubing from the needle, and the bevel side of the needle was less likely to cause damage to the tubing when it is facing the wall.

Calibration of the oxygen flow rate vs. pump flow rate: Methanol (50 mL) was placed in a 100 mL pear-shaped flask, and the open end of the pump inlet was positioned directly into the bottom of the flask. The reactor outlet was positioned along the inside wall of the flask. The flow rate of the pump was set to the lowest rate that could effectively pull methanol up the pump inlet. Then, the regulator of the oxygen balloon was opened such that the flow rate of oxygen did not cause the flow of methanol to stop. The flow rate of the pump was then slowly raised until the ratio of methanol: $O_2$ was approximately 1:1. Once an optimal flow rate was achieved, the methanol was emptied into a waste flask.

A ratio of <2:1 $CD_3OD$: 02 is necessary for complete reaction of the alkene without thermal decomposition of the intermediate hydroperoxide. Excess oxygen lowered the capacity of the reactor, thus slowing reaction time. After making any adjustments to the flow rate of either $O_2$ or the pump, the system was equilibrated after one full cycle to assess the ratio.

Loading of the reactor and running the reaction: Once the flow rate was set, the pump was turned off, and the reaction flask was loaded with phorbol diacetate 3 (6.037 g, 13.46 mmol, 1 equiv) and Rose Bengal (34.2 mg, 0.0336 mmol, 1.7 mM) dissolved in $CD_3OD$ (20 mL). The pump was turned on, and after one complete cycle, the green LED strip was turned on, and the exterior of the reactor was lined with aluminum foil. The water bath was maintained at approximately 20° C. throughout the course of the reaction (about 6 hr) using dry ice. Analytical samples were taken from the reaction flask directly to determine the progress of the photooxidation by TLC/NMR. After TLC/NMR analysis indicated that the starting material was completely converted to intermediate SI-3, the pump was stopped.

Quenching the reaction and workup: Thiourea (3.073 g, 40.38 mmol, 3 equiv) was added to a 250 mL flask and the reactor outlet was moved from the reaction flask to the flask containing thiourea. The pump was turned back on, and the reaction mixture was pumped into the thiourea flask. The reaction flask was rinsed with $CH_3OH$ (2×30 mL) to purge the reactor, and the thiourea flask was sonicated for 15 min at room temperature. TLC indicated complete reduction of the hydroperoxide intermediate SI-3, and the solution was transferred to a separatory funnel with EtOAc (500 mL) and brine (100 mL). The layers were separated, and the organic layer was washed with brine (4×100 mL). The combined aqueous layers were back extracted with EtOAc (2×200 mL) and the back extract was again washed with brine (100 mL) to ensure removal of thiourea byproduct (confirmed by TLC). The washed back extract was combined with the original organic layers and dried over $Na_2SO_4$.

Activated charcoal was added (15 g) and the crude mixture was filtered and concentrated to afford the crude product 4 as a white foam (5.511 g, 88%).

Aqueous work-up was sufficient to obtain the product in high purity. As a result, the product was used in the following step without chromatographic purification. Yield of product 4 was determined via crude qNMR (dimethyl terephthalate internal standard in $CD_3OD$ solvent).

TLC: Rf=0.30 (90% EtOAc/Hex), UV active, brown spot in p-anisaldehyde FTIR: (ATR) 3357 (br), 3190, 2922, 2852, 1712, 1658, 1631, 1468, 1423, 1412, 1375, 1263, 1236, 1080, 1059, 1018, 978, 802, 719, 700, 636 $cm^{-1}$ $[\alpha]^{24.6}D$=+4.4° (c=0.21, MeCN)

$^1$H-NMR (400 MHz, $CDCl_3$) δ 7.57 (m, 1H), 6.13 (s, 1H), 5.77 (s, 1H), 5.37 (d, J=9.7 Hz, 1H), 4.76 (d, J=8 Hz, 1H), 4.29 (m, 2H), 4.13 (d, J=5.5 HZ, 1H), 3.89 (s, 1H), 3.82 (brs, 1H), 3.02 (app s, 1H), 2.58 (dd, J=5.5, 8.8 Hz, 1H), 2.19 (dq, J=10.4, 6.1 Hz, 1H), 2.08 (s, 3H), 2.07 (s, 3H), 1.87 (s, 1H), 1.75 (dd, J=1.2, 2.6 Hz, 1H), 1.51 (d, J=5.4 Hz, 1H), 1.18 (s, 3H), 1.17 (s, 3H), 0.89 (d, J=6.2 Hz, 3H)

$^{13}$C-NMR: (101 MHz, $CDCl_3$, 24 peaks total) δ 206.8, 174.5, 171.2, 160.0, 153.3, 134.2, 125.9, 77.0, 75.7, 72.7, 70.0, 66.5, 66.3, 56.5, 48.1, 44.2, 31.6, 25.8, 23.5, 21.3, 21.2, 17.0, 14.7, 10.4

HRMS calculated for $C_{24}H_{32}NaO_9^+$ [M+Na]$^+$ 487.1938; found: 487.1930

Example 7

Step 4: Conversion of C7-Alcohol 4 to β-Epoxide 5 (Installation of C5,C6 β-Epoxide)

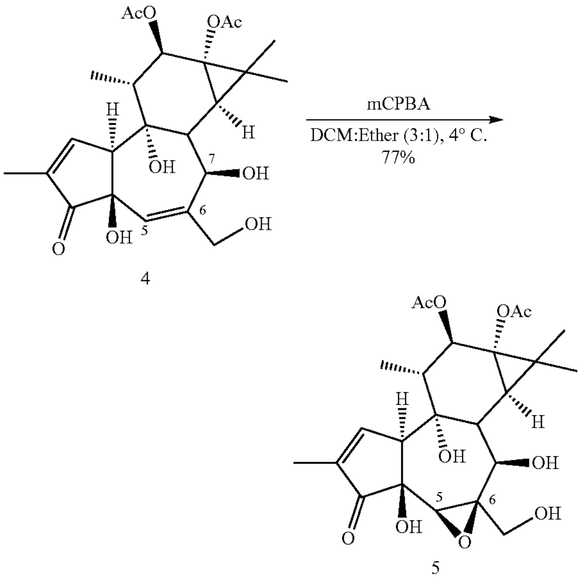

4

5

Chemicals: mCPBA (Sigma-Aldrich, 77%): used without purification.

To a one-neck, 100 mL round-bottom flask equipped with a stir bar was added C7-alcohol 4 (5.51 g, 11.9 mmol, 1 equiv), dichloromethane (45 mL), and diethyl ether (15 mL). The solution was cooled to 4° C. in a 4° C. cold room and stirred for 30 minutes, upon which mCPBA (5.32 g, 23.7 mmol, 2 equiv) was added in a single portion. The reaction was stirred for 18 hours at 4° C. TLC analysis indicated complete conversion to desired β-epoxide 5 as well as minimal formation of the undesired α-epoxide. The reaction was poured into a separatory funnel with 200 mL of a 1:1 v/v mixture of sat. $Na_2SO_3$ and sat. $NaHCO_3$. The layers were separated, and the aqueous layer was extracted with EtOAc (5×100 mL). The combined organic layers were dried over $Na_2SO_4$, filtered, and concentrated. Purification was accomplished by silica gel vacuum column chromatography (20-90% EtOAc/Hex, 9×15 cm) affording 3-epoxide 5 (4.399 g, 77%) as a white solid. Compound purity was established by TLC (one spot) analysis.

TLC: Rf=0.24 (90% EtOAc/Hex), UV active, burgundy spot in p-anisaldehyde

FTIR: (ATR) 3400 (br), 2962, 2924, 2885, 2858, 1709, 1649, 1630, 1456, 1375, 1323, 1259, 1232, 1151, 1130, 1082, 1020, 978, 808, 737 $cm^{-1}$ $[\alpha]^{23.2}D$=+60.0° (c=1.02, $CH_2Cl_2$)

$^1$H-NMR: (400 MHz, $CDCl_3$) δ 7.59 (app s, 1H), 5.75 (s, 1H), 5.30 (d, J=10.6 Hz, 1H), 4.72 (brs, 1H), 4.46 (t, J=9.2 Hz, 1H), 4.05-3.96 (m, 3H), 3.88 (d, J=11.6 Hz, 1H), 3.77 (s, 1H), 2.91 (s, 1H), 2.40 (dd, J=5.3, 9.6 Hz, 1H), 2.20-2.12 (m, 1H), 2.06 (s, 3H), 1.76 (app s, 3H), 1.37 (d, J=5.9 Hz, 1H), 1.17 (s, 3H), 1.15 (s, 3H), 0.84 (d, J=5.9 Hz)

$^{13}$C-NMR: (101 MHz, $CDCl_3$, 24 peaks total) δ 207.2, 174.5, 171.2, 161.1, 134.4, 76.8, 76.1, 71.5, 69.6, 69.0, 66.2, 63.4, 61.4, 57.3, 43.4, 39.3, 31.6, 25.8, 23.3, 21.3, 21.2, 16.7, 14.5, 10.4

Example 8

Srep 5: Conversion or β-Epoxide 5 to Exo-Alkene 6 (Installation of C6,C20 Exo-Alkene)

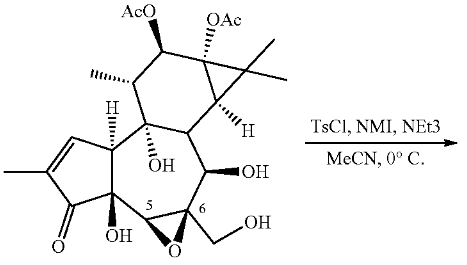

5

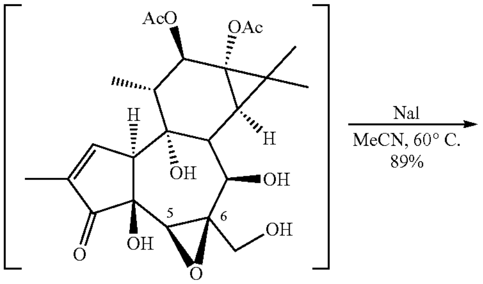

SI-4

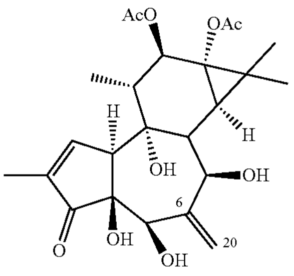

6

Chemicals: TsCl (Acros, >99%): used without purification; Triethylamine (Sigma-Aldrich): distilled from $CaH_2$ prior to use; 1-methyl-1H-imidazole (Sigma-Aldrich, 99%): used without purification Sodium iodide (AK scientific, 98%): used without purification; MeCN (Acros, 99.9%): used without purification To a flame-dried, one-neck, 250 mL round-bottom flask equipped with a stir bar was added β-epoxide 5 (9.945 g, 20.70 mmol, 1 equiv), triethylamine (4.33 mL, 31.05 mmol, 1.5 equiv), NMI (169.9 mg, 2.070 mmol, 0.1 equiv), and anhydrous acetonitrile (100 mL) under nitrogen. The solution was cooled with an ice bath (0° C.) and stirred for 15 minutes. A solution of tosyl chloride (4.735 g, 24.84 mmol, 1.2 equiv) in acetonitrile (10 mL) was prepared in a round-bottom flask then transferred to an addition funnel that was affixed to the reaction vessel. The tosyl chloride was added dropwise to the solution of 5 over 20 minutes, at which point the reaction was left to stir for an additional 30 minutes. TLC analysis indicated complete conversion to the intermediate SI-4. Water (1.5 mL) was added to quench excess tosyl chloride, then sodium iodide (9.307 g, 62.09 mmol, 3 equiv) was added directly in a single portion. The reaction flask was fitted with a reflux condenser and the reaction was refluxed at 60° C. for 20 hours. TLC analysis indicated complete conversion of SI-4 to the desired exo-alkene 6. The reaction was diluted with EtOAc (1 L) and washed with sat. $Na_2S_2O_3$ (3×250 mL) followed by brine (250 mL). The combined aqueous layers were extracted with EtOAc (2×500 mL). The combined organic layers were dried over $Na_2SO_4$, filtered, and concentrated. Purification was accomplished by silica gel vacuum column chromatography (20-55% EtOAc/Hex, 9×15 cm) affording exo-alkene 6 (8.523 g, 89%) as a white solid. Compound purity was established by TLC (one spot) analysis.

Note that dropwise addition of TsCl and maintenance of reaction temperature at 0° C. was necessary to avoid tosylation of the C7 alcohol.

TLC: Rf=0.27 (50% EtOAc/Hex), UV active, pink in p-anisaldehyde

FTIR: (ATR) 3392 (br), 2979, 2956, 2925, 2883, 1716, 1628, 1433, 1375, 1325, 1263, 1236, 1093, 1061, 1018, 978, 916, 814, 737, 436 $cm^{-1}$ $[\alpha]^{24.1}D$=+13.1° (c=0.28, $CH_2Cl_2$)

$^1$H-NMR: (400 MHz, $CDCl_3$) δ 7.71 (m, 1H), 5.74 (brs, 1H), 5.47 (m, 1H), 5.47 (app q, J=1.4 Hz, 1H), 5.41 (app t, J=1.5 Hz, 1H), 5.34 (d, J=10.2 Hz, 1H), 4.89 (brs, 1H), 4.46 (d, J=8.8 Hz, 1H), 4.37 (app t, J=1.7 Hz, 1H), 3.61 (s, 1H), 3.13 (app p, J=2.5 Hz, 1H), 2.25 (dd, J=5.7, 8.9 Hz, 1H), 2.07 (s, 3H), 2.05 (s, 3H), 2.00 (dq, J=10.1, 6.5 Hz, 1H), 1.78 (dd, J=1.3, 2.8 Hz, 1H), 1.53 (d, J=5.8 Hz, 1H), 1.20 (s, 3H), 1.11 (s, 3H), 0.86 (d, J=6.5 Hz, 3H)

$^{13}$C-NMR: (101 MHz, $CDCl_3$, 24 peaks total) δ 210.1, 174.1, 171.1, 162.9, 151.9, 134.5, 111.0, 77.3, 76.0, 74.3, 73.8, 68.2, 66.4, 53.1, 46.3, 44.4, 31.7, 25.8, 23.6, 21.2, 21.1, 17.3, 14.8, 10.1

HRMS calculated for $C_{24}H_{32}NaO_9^+$ [M+Na]$^+$: 487.1938; found: 487.1933

Example 9

Step 6: Conversion of Exo-Alkene 6 to C5β-Hydroxy Phorbol Diacetate 7 (Transposition of C7-OH)

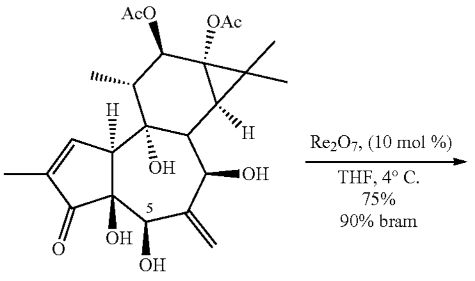

6

-continued

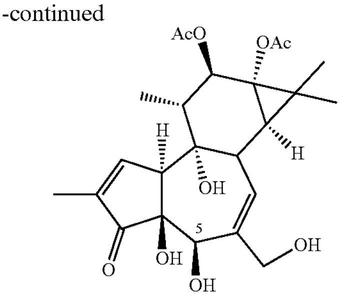

7

Chemicals: $Re_2O_7$ (Alfa Aesar, 99.9%): used without purification; THF (Sigma-Aldrich): freshly distilled.

To a flame-dried, one-neck, 50 mL round-bottom flask equipped with a stirrer was added exo-alkene 6 (1.006 g, 2.166 mmol, 1 equiv) in anhydrous THF (24.0 mL) under argon. Rhenium (VII) oxide (90.0 mg, 0.186 mmol, 0.0858 equiv) was quickly weighed out and directly added to the reaction vessel in a single portion. The rhenium catalyst is stored under $N_2$ in a glovebox and is used as needed.

Residual starting material eluted at 50% EtOAc/Hex. The desired product then elutes at 90% EtOAc/Hex. The flask was sealed with parafilm and cooled to 4° C. in a 4° C. cold room and stirred for 18 hours. TLC indicated significant formation of the desired product 7 as well as residual starting material. The reaction was quenched with sat. $NaHCO_3$ (50 mL) and the aqueous layer was extracted with EtOAc (3×50 mL). The organic layers were combined and dried over $Na_2SO_4$, filtered, and concentrated. Purification was accomplished by silica gel flash column chromatography (20-90% EtOAc/Hex, 4×16 cm) affording C5β-hydroxy phorbol diacetate 7 (762.5 mg, 76%, 90% brsm) as a white solid (Note 2).

Compound purity was established by TLC (one spot) analysis.

Six Grams of C5β-Hydroxy Phorbol Diacetate 7 Prepared from One Reaction (Table 1, Entry 19)

TABLE 1

Conditions screened for rhenium transposition

| Entry | Scale | Catalyst* | Solvent | Temp | Conc. (M) | Result |
|---|---|---|---|---|---|---|
| 1 | 20 mg | $MeReO_3$ | $Et_2O$ | Rt | 0.01 | No reaction |
| 2 | 20 mg | $MeReO_3$ | Toluene | 70° C. | 0.01 | Poor conversion |
| 3 | 8 mg | $MeReO_3$ | MeCN | 55° C. | 0.01 | No reaction |
| 4 | 12 mg | $MeReO_3$ | THF | 55° C. | 0.01 | No reaction |
| 5 | 10 mg | $MeReO_3$ | $Et_2O$ | 55° C. | 0.01 | Poor conversion |
| 6 | 10 mg | $MeReO_3$ | MTBE | 70° C. | 0.01 | Poor conversion |
| 7 | 10 mg | $MeReO_3$ | DCE | 70° C. | 0.01 | Good conversion |
| 8 | 10 mg | $MeReO_3$ | Toluene | 100° C. | 0.01 | Decomposition |
| 9 | 50 mg | $MeReO_3$ | DCE | 70° C. | 0.2 | 62.5% yield, 90.0% brsm |
| 10 | 500 mg | $MeReO_3$ | DCE | 70° C. | 0.2 | 56.8% yield, 74.1% brsm |
| 11 | 10 mg | $Re_2O_7$ | $Et_2O$ | Rt | 0.09 | Product/byproducts |
| 12 | 43 mg | $Re_2O_7$ | DCM | Rt | 0.03 | Product/byproducts |
| 13 | 10 mg | $Re_2O_7$ | DCM | Rt | 0.0056 | Product/byproducts |
| 14 | 23 mg | $Re_2O_7$ | DCM/THF | Rt | 0.012 | Product/byproducts |
| 15 | 17 mg | $Re_2O_7$ | THF | Rt | 0.012 | Product/byproducts |
| 16 | 45.3 mg | $Re_2O_7$ | THF | 4° C. | 0.033 | 72.8% yield, ~90% brsm |
| 17 | 192.3 mg | $Re_2O_7$ | THF | 4° C. | 0.083 | 80.0% yield, ~90% brsm |
| 18 | 1.006 g | $Re_2O_7$ | THF | 4° C. | 0.090 | 75.8% yield, ~90% brsm |
| 19 | 8.2536 g | $Re_2O_7$ | THF | 4° C. | 0.089 | 72.7% yield, ~90% brsm |

*Catalyst loading was usually between 15-20 mol % for test reactions. For the optimized scale-up reactions, catalyst loading was about10 mol %.

TLC: Rf=0.21 (90% EtOAc/Hex, UV active, green spot in p-anisaldehyde)

FTIR: (ATR) 3394 (br), 2958, 2925, 2881, 1701, 1628, 1427, 1373, 1327, 1261, 1230, 1082, 1063, 1016, 978, 933, 914, 877, 804, 733, 702, 617 $cm^{-1}$ $[\alpha]^{23.0}D$=+35.7° (c=0.88, $CH_2Cl_2$)

$^1$H-NMR: (400 MHz, $CDCl_3$) δ 7.62 (m, 1H), 5.64 (brs, 1H), 5.63 (d, J=5.0 Hz, 1H), 5.33 (d, J=10.2 Hz, 1H), 4.34 (s, 1H), 4.20 (d, J=12.3 Hz, 1H), 4.121 (d, J=12.1 Hz, 1H), 4.122 (s, 1H), 3.39 (app t, J=5.4 Hz, 1H), 3.02 (app p, J=2.75 Hz, 1H), 2.10-2.02 (m, 1H), 2.07 (s, 3H), 2.05 (s, 3H), 1.74 (dd, J=1.4, 3.0 Hz, 1H), 1.05 (d, J=5.4 Hz, 1H), 0.9 (d, J=6.5 Hz, 1H)

$^{13}$C-NMR: (101 MHz, $CDCl_3$, 24 peaks total) δ 209.6, 174.1, 171.1, 161.7, 141.2, 134.1, 132.2, 77.0 (2C), 73.7, 70.3, 67.1, 65.7, 53.9, 43.7, 38.7, 36.2, 26.0, 23.8, 21.2, 21.1, 16.7, 14.9, 10.1

HRMS calculated for $C_{24}H_{32}NaO_9^+$ $[M+Na]^+$: 487.1938; found: 487.1933

$McReO_3$ was explored due to its reasonable stability to air and water, permitting a convenient path to scalability. Unfortunately, the desired transposition could only be achieved in select solvents at elevated temperatures. Upon scale-up of the apparent best conditions with $McReO_3$, a significant drop in yield was observed (entry 10). As a result, different rhenium catalysts were explored. A more reactive catalyst, $Re_2O_7$, afforded the desired product at room temperature with minimal byproducts. This catalyst is equally desirable because it is commercially available, albeit it is sensitive to air and water. Upon solvent and temperature optimization, it was found that the desired product could be obtained in an average of 75% yield (nearly quantitative brsm) on multi-gram scale (entry 16-19).

Example 10

Step 7: Conversion of C5β-Hydroxy Phorbol Diacetate 7 to Acetonide 8 (C5,C20 Acetonide Protection)

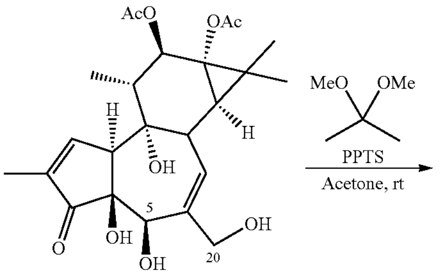

7

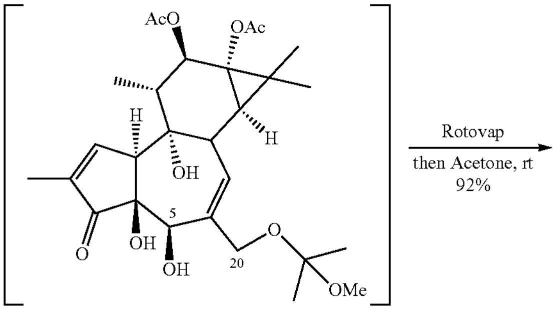

SI-5

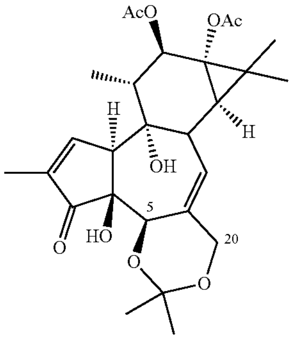

8

Chemicals: 2,2-DMP (Sigma-Aldrich, 98%): used without purification; PPTS (AK scientific, 95%): used without purification; Acetone (Acros, 99.8%): used without purification.

To a flame-dried, one-neck, 250 mL round-bottom flask equipped with a stir bar was added 7 (1.0245 g, 2.2055 mmol, 1 equiv) followed by anhydrous acetone (25.0 mL).

2,2-dimethoxypropane (75.0 mL, 612 mmol, 278 equiv) was added in a single portion followed by PPTS (81.1 mg, 0.323 mmol, 0.146 equiv). The reaction was stirred for 45 minutes at rt. TLC analysis indicated complete conversion to the intermediate SI-5. The stir bar was removed, and the reaction was concentrated to remove excess DMP. Closing of the C20 methyl ketal in the presence of excess DMP resulted in slow reaction times and formation of byproducts.

The crude intermediate was then re-dissolved in anhydrous acetone (25.0 mL) and stirred for an additional 15 minutes at rt. Anhydrous acetone was necessary for this step to avoid hydrolysis of the intermediate SI-5. TLC analysis indicated complete conversion to acetonide 8.

The reaction was quenched with sat. $NaHCO_3$ (100 mL). The aqueous layer was separated and extracted with EtOAc (3×100 mL). The organic layers were combined, dried over $Na_2SO_4$, filtered, and concentrated. Purification was accomplished by silica gel flash chromatography (10-40% EtOAc/Hex, 3×13 cm) affording acetonide 8 (1.0204 g, 92%) as a white solid. This intermediate should be stored under $N_2$ to avoid hydrolysis back to the starting material. Compound purity was established by TLC (one-spot) analysis.

TLC: Rf=0.31 (50% EtOAc/Hex), UV active, green spot in p-anisaldehyde

FTIR: (ATR) 3396 (br), 2991, 2958, 2925, 2854, 1711, 1633, 1456, 1373, 1329, 1259, 1230, 1211, 1163, 1082, 1020, 997, 980, 914, 872, 802, 735 $cm^{-1}$ $[\alpha]^{23.2}D$=+10.6° (c=0.36, $CH_2Cl_2$)

$^1$H-NMR: (400 MHz, $d_6$-acetone) δ 7.54 (m, 1H), 5.37 (d, J=3.7 Hz, 1H), 5.34 (d, J=10.2 Hz, 1H), 5.32 (brs, 1H), 4.56 (s, 1H), 4.55 (d, J=11.8 Hz, 1H), 4.22 (s, 1H), 3.94 (d, J=12.0 Hz, 1H), 3.55-3.52 (m, 1H), 2.99 (pp p, J=2.86 Hz, 1H), 2.01 (s, 6H), 2.04-1.96 (m, 1H), 1.67 (dd, J=1.41, 2.95 Hz, 1H), 1.43 (s, 3H), 1.29 (s, 3H), 1.21 (s, 6H), 1.17 (d, J=6.3 Hz, 1H), 0.83 (d, J=6.5 Hz, 1H)

$^{13}$C-NMR: (101 MHz, $d_6$-acetone, 27 peaks total) δ 205.9, 174.4, 171.4, 159.8, 137.0, 135.0, 126.8, 100.6, 78.0, 77.8, 74.4, 73.3, 68.9, 66.8, 55.4, 45.2, 40.4, 36.9, 29.4, 27.0, 24.0, 21.2, 21.0, 20.3, 17.3, 15.4, 10.2

HRMS calculated for $C_{27}H_{36}NaO_9^+$ $[M+Na]^+$: 527.2251; found: 527.2246

Example 11

Step 8: Conversion of Acetonide 8 to α-Epoxide 9 (Installation of C6,C7 α-Epoxide)

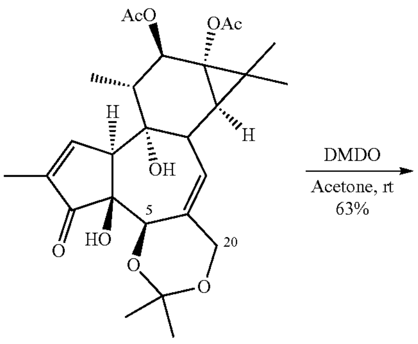

8

-continued

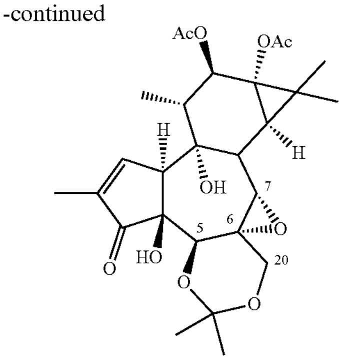

9

Chemicals: OXONE® (Alfa Aesar): used without purification; $NaHCO_3$ (Fisher, >99.7%) used without purification.

To a flame-dried, one-neck, round-bottom flask was added acetonide 8 (1.010 g, 2.002 mmol, 1 equiv). DMDO (81.5 mL, 5.89 mmol, 3 equiv) was added via a graduated cylinder that had been pre-cooled in a −20° C. freezer. The reaction was stirred for 12 hours at rt. NMR analysis indicated about 25% remaining starting material. TLC resolution between 8 and 9 was minimal but could be accomplished using 6% acetone/DCM. NMR was preferred for monitoring the reaction. $CDCl_3$ should be avoided to avoid acidic decomposition of the acetonide. The NMR solvent typically used was $d_6$-acetone.

An additional equivalent of DMDO (27.7 mL, 2.0 mmol, 1 equiv) was added via a graduated cylinder that had been pre-cooled in a −20° C. freezer. The reaction was stirred for an additional 3 hours at rt. NMR analysis indicated complete consumption of starting material.

The reaction was quenched with 2-methyl-2-butene (5 mL) and concentrated directly. Purification was accomplished by silica gel flash chromatography (5-35% EtOAc/Hex, 3×13 cm) affording α-epoxide 9 (650.1 mg, 63%) as a white solid. Compound purity was established by TLC (one spot) analysis.

TLC: Rf=0.32 (50% EtOAc/Hex), UV active, blue spot in p-anisaldehyde

FTIR: (ATR) 3402 (br), 2989, 2925, 2881, 1724, 17091631, 1354, 1373, 1329, 1261, 1227, 1161, 1080, 1020, 980, 916, 881, 833, 735, 636, 615 $cm^{-1}$ $[\alpha]^{23.6}D$=+17.8° (c=0.49, $CH_2Cl_2$)

$^1$H-NMR: (400 MHz, d6-acetone) δ 7.52 (m, 1H), 5.33 (d, J=10.1 Hz), 5.29 (brs, 1H), 4.51 (s, 1H), 4.08 (s, 1H), 3.97 (d, J=12.9 Hz, 1H), 3.90 (app p, J=2.9 Hz, 1H), 3.37 (d, J=12. 9 Hz, 1H), 3.19 (d, J=3.9 Hz, 1H), 3.06 (s, 1H), 2.01 (s, 3H), 1.99 (s, 3H), 1.91 (dq, J=10.2, 6.6 Hz, 1H), 1.66 (dd, J=2.9, 1.4 Hz, 1H), 1.37 (d, J=6.9 Hz, 1H), 1.34 (s, 3H), 1.33 (s, 3H), 1.22 (s, 3H), 1.21 (s, 3H), 0.77 (d, J=6.5 Hz, 3H)

$^{13}$C-NMR (101 MHz, d6-acetone, 27 peaks total) δ 205.8, 174.1, 171.3, 160.7, 134.7, 101.6, 77.9, 77.6, 73.7, 69.6, 66.9, 66.3, 65.4, 61.7, 50.5, 46.6, 37.1, 36.0, 27.4, 24.9, 23.9, 22.9, 21.2, 21.0, 17.5, 15.4, 10.2

HRMS calculated for $C_{27}H_{36}NaO^+$ $[M+Na]^+$: 543.2201; found: 543.2194

Example 12

DMDO Preparation (Large Scale)

A 12 L three-neck flask was equipped with a mechanical stirrer, a condenser, a receiving flask, and a secondary receiving flask according to the diagram below (FIG. S6). The flask was cooled to 0° C. in an ice bath. Acetone (1.5 L), water (1.5 L), and $NaHCO_3$ (1.5 kg) were added directly and stirred for 30 minutes. The condensers and the receiving flasks were cooled to −78° C. OXONE® (1.5 kg) was added portion wise as 150 g aliquots every 10 minutes. After addition of each OXONE® aliquot, the flask was sealed, and pressure was reduced such that a steady stream of DMDO condensed into the primary receiving flask. The system was backfilled with nitrogen before adding the next portion of OXONE®. This was repeated until all OXONE® was added. The reaction was allowed to stir for 1 additional hour after the last portion of OXONE® was added. DMDO was obtained as a yellow solution, and the reaction flask was quenched with sat. $Na_2SO_3$ (500 mL) and diluted with water (2.0 L). Concentration of DMDO was determined via the following titration procedure. Triphenylphosphine (20 mg, 0.076 mmol) was added to a 1-dram vial followed by the solution of DMDO in acetone (0.5 mL, unknown mM). The mixture was stirred at room temperature for 20 minutes, and a 0.1 mL aliquot was removed for $^{31}$P-NMR. The ratio of triphenylphosphine oxide (28 ppm) vs. triphenylphosphine (~7 ppm) and the exact mass of triphenylphosphine were used to calculate the concentration of DMDO in the solution (about 0.07 M). The DMDO solution was stored at −20° C. and was freshly titrated upon usage.

TABLE 2

Conditions screened for α-epoxidation

| Oxidant | Base | Temp | Result |
|---|---|---|---|
| mCPBA | — | Rt | Acetonide removal |
| mCPBA | $Na_2CO_3$ | Rt | Decomposition |
| mCPBA | $NaHCO_3$ | Rt | Decomposition |
| mCPBA | $Cs_2CO_3$ | Rt | Decomposition |
| mCPBA | $NaHCO_3$ | 40° C. | Decomposition |
| mCPBA | $NaHCO_3$ | 0° C. | Decomposition |
| mCPBA | $Na_2HPO_4$ | Rt | Decomposition |
| mCPBA | 2,6-ditertbutyl pyridine | Rt | No reaction |
| TFPAA | $NaHCO_3$ | Rt | Decomposition |
| DMDO (in situ) | $NaHCO_3$ | Rt | No reaction |
| TFDO (in situ) | $NaHCO_3$ | Rt | Decomposition |
| $VO(acac)_2$, $H_2O_2$ | — | Rt | Acetonide removal |
| $MeReO_3$, $H_2O_2$ | — | Rt | Acetonide removal |
| DMDO (3 eq) | — | Rt | 63% yield |

Example 13

Steps 9-10. Conversion of α-Epoxide 9 to Methyl Butanoate 11 (C12,C13 Saponification and C13 Esterification)

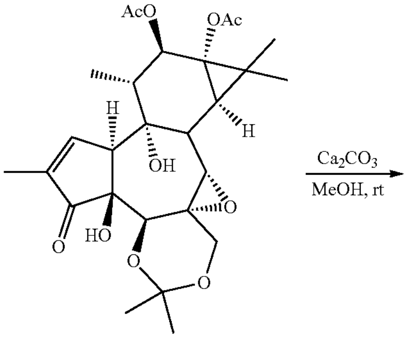

9

-continued

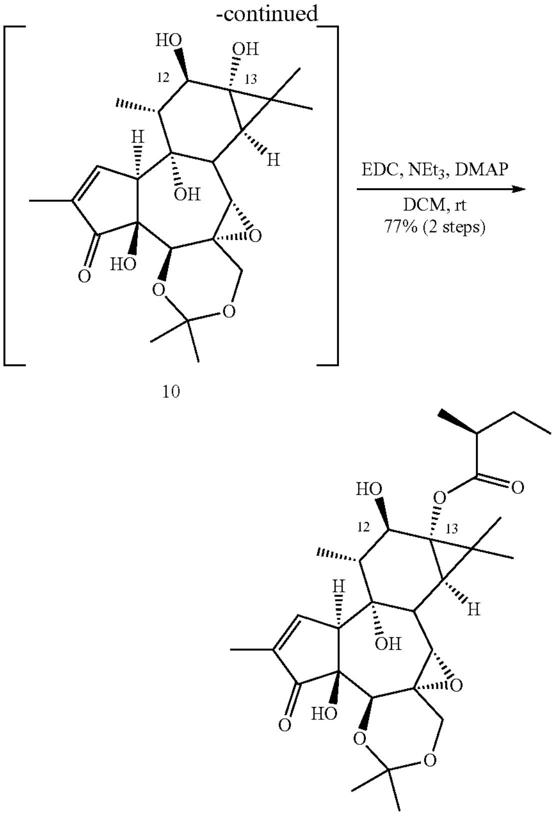

10

11

Chemicals: (S)-2-methylbutanoic acid (Acros, 98%): used without purification; EDC (Oakwood): used without purification; DMAP (Oakwood): used without purification; Triethylamine (Sigma-Aldrich): distilled from $CaH_2$ prior to use To an 8-dram vial equipped with a stir bar was added α-epoxide 9 (2.94 g, 5.65 mmol, 1 equiv). A solution of cesium carbonate (75.0 mg, 0.23 mmol, 0.041 equiv) was prepared in methanol (9 mL) and sonicated to dissolution. This basic solution of methanol was added directly to the reaction vessel as a single portion. The reaction mixture was stirred at room temperature for 18 hours. TLC analysis indicated complete conversion to intermediate 10. The reaction was quenched with sat. $NH_4Cl$ (25 mL), diluted with brine (100 mL), and extracted with EtOAc (5×100 mL) until TLC of the aqueous layer no longer showed product. The resulting oil was directly used in the next step. While diol 10 could be isolated in pure form for characterization, low yields were observed due to its polarity and incompatibility with normal phase silica gel column chromatography. As a result, 10 was used directly in the subsequent step without purification. (Note 1). In a 100 mL round-bottom flask, EDC (3.42 g, 17.8 mmol, 3.15 equiv), triethylamine (2.60 mL, 18.7 mmol, 3.30 equiv), (S)-2 -methylbutanoic acid (1.73 g, 17.0 mmol, 3.0 equiv), and DMAP (138 mg, 1.13 mmol, 0.2 equiv) were dissolved in DCM (75 mL) and sonicated until homogeneous. In a separate 50 mL round-bottom flask, the crude diol 10 was dissolved in anhydrous THE (25 mL) and the DCM solution of activated acid was added directly in one portion. The reaction was stirred at rt for 2 hours. TLC analysis indicated complete consumption of 10 and conversion to methyl butanoate 11. The reaction was quenched with methanol (10 mL) and diluted with brine (50 mL) and 1 M HCl (0.5 mL). The aqueous layer was extracted with DCM (3×50 mL). The combined organic layers were dried over $Na_2SO_4$, filtered, and concentrated. Purification was accomplished by silica gel flash column chromatography (10%-40% EtOAc/Hex, 4×16 cm) affording methyl butanoate 11 (2.27 g, 77% over 2 steps) as a white foam. Compound purity was established by TLC (one spot) analysis.

Compound 10:

TLC: Rf=0.26 (50% Acetone/Hex), UV active, green spot in p-anisaldehyde

FTIR: (ATR) 3399 (br), 2965, 2924, 2879, 1708, 1651, 1627, 1457, 1379, 1325, 1257, 1198, 1154, 1131, 1073, 1022, 979, 934, 801, 732, 601 $cm^{-1}$ $[\alpha]^{23.1}$ D=−8.1° (c=0.20, $CH_2Cl_2$)

$^1$H-NMR: (400 MHz, $CD_3OD$) δ 7.66 (m, 1H), 4.13 (d, J=13.0 Hz, 1H), 4.06 (s, 1H), 4.02 (d, J=9.8 Hz, 1H), 3.75 (p, J=2.7 Hz, 1H), 3.37 (d, J=13.1 Hz, 1H), 3.08 (d, J=7.1 Hz, 1H), 3.02 (s, 1H), 1.74 (dd, J=2.9, 1.3 Hz, 3H), 1.68 (dq, J=9.7, 6.5 Hz, 1H), 1.45 (s, 3H), 1.38 (s, 3H), 1.30 (s, 3H), 1.15 (s, 3H), 0.99 (d, J=6.5 Hz, 3H), 0.95 (d, J=7.1 Hz, 1H)

$^{13}$C-NMR: (101 MHz, $CD_3OD$, 23 peaks total) δ 206.8, 161.4, 134.0, 101.0, 81.3, 77.1, 72.9, 68.9, 65.4, 65.3, 62.2, 61.5, 51.5, 47.4, 36.6, 35.8, 26.4, 23.0, 22.4, 21.5, 16.6, 14.8, 8.6

Compound 11:

TLC: Rf=0.51 (50% EtOAc/Hex), UV active, green spot in p-anisaldehyde

FTIR: (ATR) 3502 (br), 3408 (br), 2970, 2925, 2879, 1711, 1631, 1360, 1377, 1329, 1313, 1267, 1125, 1198, 1180, 1157, 1993, 1030, 985, 924, 881, 833, 735, 526 $cm^{-1}$ $[\alpha]^{23.8}$D=+33.5° (c=0.38, $CH_2Cl_2$)

$^1$H-NMR: (400 MHz, $CDCl_3$): δ 7.53 (m, 1H), 4.07 (s, 1H), 3.96 (d, J=12.9 Hz, 1H), 3.89 (d, J=9.3 Hz, 1H), 3.71 (app p, J=2.8 Hz), 3.57 (s, 1H), 3.53 (d, J=13.0 Hz, 1H), 2.40 (h, J=7.0 Hz), 1.78-1.65 (m, 2H), 1.74, dd, J=1.4, 2.4 Hz, 1H), 1.46 (s, 3H), 1.42 (s, 3H), 1.28 (s, 3H), 1.22 (d, J=7.4 Hz, 1H), 1.19 (s, 3H), 1.15 (d, J=7.0 Hz, 3H), 1.00 (d, J=6.5 Hz, 3H), 0.91 (t, J=7.4 Hz, 3H)

$^{13}$C-NMR (101 MHz, $CDCl_3$, 28 peaks total) δ 205.8, 180.2, 160.4, 134.4, 101.3, 78.5, 77.4, 72.5, 68.6, 68.5, 65.9, 65.7, 61.4, 51.1, 47.2, 41.1, 36.8, 34.4, 28.0, 26.6, 24.7, 23.6, 22.4, 17.5, 16.7, 16.2, 11.8, 10.1

HRMS calculated for $C_{28}H_{40}NaO_9^+$ $[M+Na]^+$: 543.2561; found: 543.2560

Example 14

Step 11. Conversion of Methyl Butanoate 11 to Tiglate 12 (C12 Esterification)

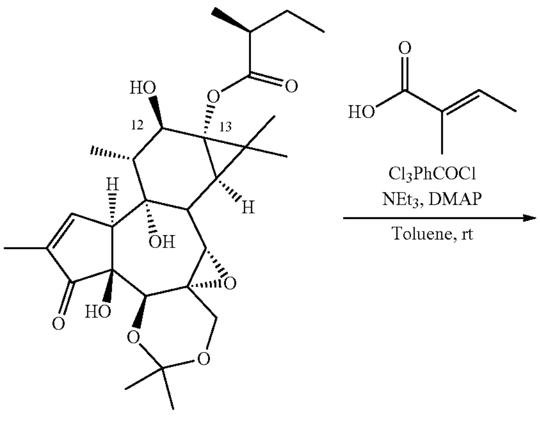

11

-continued

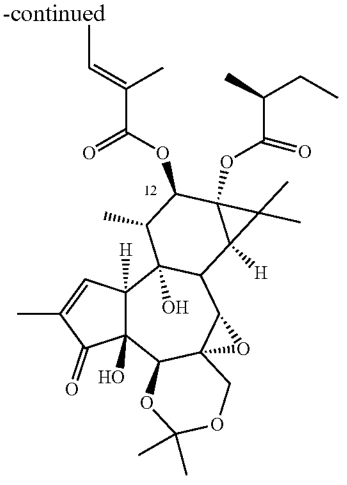

12

Chemicals: 2,4,6-trichlorobenzoyl chloride (TCl, >98%): used without purification; Tiglic acid (TCl, >98%): used without purification; DMAP (Oakwood): used without purification; Triethylamine (Sigma-Aldrich): distilled from $CaH_2$ prior to use.

To a flame-dried 50 mL round-bottom flask equipped with a stir bar was added tiglic acid (580 mg, 5.79 mmol, 2.2 equiv) followed by anhydrous toluene (15 mL). Triethylamine (1.47 mL, 10.5 mmol, 4 equiv) was added in one portion followed by 2,4,6-trichlorobenzoyl chloride (0.822 mL, 5.26 mmol, 2 equiv). This mixture was stirred vigorously at rt for 2 hours. Methyl butanoate 11 (1.37 g, 2.63 mmol, 1 equiv) was dissolved in anhydrous toluene (15 mL) in a separate flask. The substrate solution was added to the previously described solution of in situ generated mixed anhydride in one portion followed by addition of DMAP (836 mg, 6.84 mmol, 2.6 equiv). The reaction mixture was stirred at rt for 2 hours. TLC analysis indicated complete consumption of methyl butanoate 11. The reaction was diluted with sat. $NaHCO_3$ (50 mL) and extracted with EtOAc (3×50 mL). The combined organic layers were dried over $Na_2SO_4$, filtered, and concentrated. Purification was accomplished by silica gel flash column chromatography (20%-40% $Et_2O$/Hex, 2×15 cm) affording tiglate 12 (1.33 g, 84%) as a white foam. Compound purity was established by TLC (one spot) analysis.

TLC: Rf=0.73 (50% EtOAc/Hex), UV active, green spot in p-anisaldehyde

FTIR: (ATR) 3396 (br), 2968, 2925, 2879, 1707, 1651, 1631, 1458, 1375, 1327, 1252, 1225, 1192, 1155, 1130, 1088, 1072, 1026, 978, 931, 733, 586 $cm^{-1}$ $[\alpha]^{23.5}D$=−4.4° (c=1.22, $CH_2Cl_2$)

$^1$H-NMR (400 MHz, $CDCl_3$) δ 7.60 (m, 1H), 6.81 (qq, J=1.3, 7.0 Hz, 1H), 5.94 (brs, 1H), 5.44 (d, J=9.9 Hz, 1H), 4.13 (s, 1H), 4.03 (app p, J=3.0 Hz, 1H), 3.94 (d, J=12.9 Hz, 1H), 3.61 (d, J=12.9 Hz, 1H), 3.34 (d, J=1.0 Hz, 1H), 3.17 (d, J=6.6 Hz, 1H), 3.00 (s, 1H), 2.39 (h, J=7.0 Hz, 1H), 1.93 (dq, J=9.8, 6.5 Hz, 1H), 1.82 (t, J=1.3 Hz, 3H), 1.79 (d, J 7.0 Hz, 3H), 1.76-1.68 (m, 1H), 1.75 (dd, J=1.0, 2.7 Hz, 3H), 1.49 (s, 3H), 1.47 (s, 3H), 1.48-1.40 (m, 1H), 1.29 (s, 3H), 1.27 (d, J=6.7 Hz, 1H), 1.24 (s, 3H), 1.13 (d, 7.0 Hz), 0.93 (t, J=7.4 Hz, 3H), 0.83 (d, J=6.5 Hz, 3H).

$^{13}$C-NMR (101 MHz, $CDCl_3$, 33 peaks total) δ 206.3, 178.9, 167.6, 161.6, 137.7, 134.0, 128.6, 101.2, 76.9, 76.8, 72.8, 68.6, 65.8, 65.7, 65.6, 60.2, 49.2, 46.0, 41.3, 36.4, 36.0, 26.7, 26.3, 25.1, 23.9, 22.2, 17.4, 16.3, 15.1, 14.6, 12.4, 11.8, 10.1

HRMS calculated for $C_{33}H_{47}O_{10}^+$ $[M+H]^+$: 603.3164; found: 603.3153

Example 15

Step 12. Conversion of Tiglate 12 to EBC-46 (1) (Acetonide Deprotection)

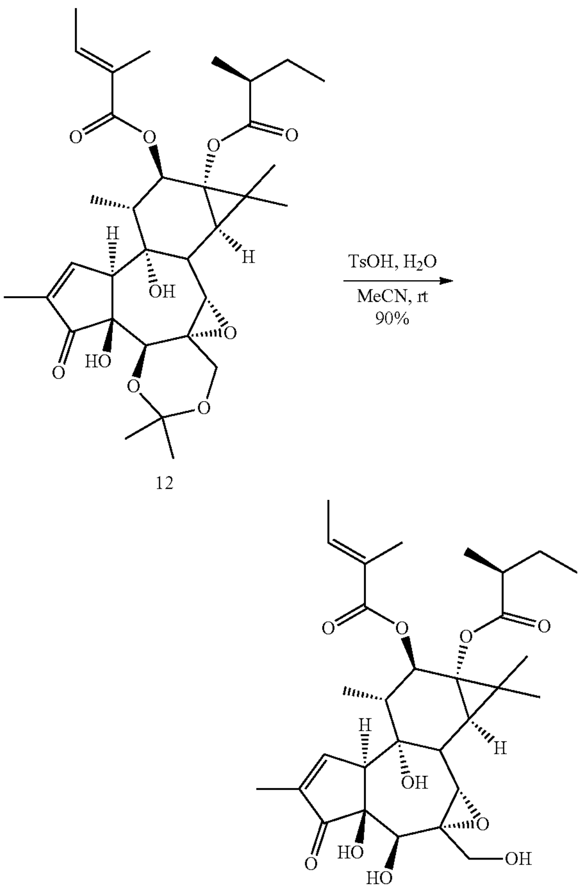

12

1

Chemicals: Tosic acid monohydrate (Sigma-Aldrich, 98%): used without purification.

To an 8-dram vial equipped with a stir bar was added tiglate 12 (1.33 g, 2.21 mmol, 1 equiv) and acetonitrile (9 mL). In a separate 8-dram vial, tosic acid (590 mg, approximately 1 M) was dissolved in water (3 mL). This acidic aqueous solution was added to the solution of the substrate in one portion. The reaction mixture was stirred at it for 21 hours. TLC analysis indicated complete consumption of tiglate 12. The reaction was diluted with sat. $NaHCO_3$ (50 mL) and extracted with EtOAc (3×50 mL). The combined organic layers were dried over $Na_2SO_4$, filtered, and concentrated. Purification was accomplished by silica gel flash column chromatography (20%-70% EtOAc/Hex, 3×13 cm) affording EBC-46 (1) (1.127 g, 90%) as a white solid. Compound purity was established by TLC (one spot) analysis.

Preparative HPLC: Prior to use in biological studies, a sample of EBC-46 was further purified by preparative HPLC using a Varian ProStar 210 Solvent Delivery System with an Agilent ProStar 325 detector set to detect at 254 nm and 210 nm. Separations were performed using a Grace Alltima C18 reverse-phase column (10 μm particle size, 280 mm×22 mm). The mobile phase was a gradient elution from 20% $MeCN/H_2O$ to 70% $MeCN/H_2O$ over 30 min, followed by 100% MeCN for 10 min (flow rate of 5 mL/min). The sample was dissolved in MeCN and 8 mg (0.5 mL) of material was loaded on the column, producing 7 mg of EBC-46. The fractions were concentrated by lyophilization to yield EBC-46 as a white powder in >99% purity.

TLC: Rf=0.11 (50% EtOAc/Hex, UV active, green spot in p-anisaldehyde)

FTIR: (ATR) 3410 (br), 2964, 2925, 2877, 1712, 1651, 1630, 1356, 1379, 1338, 1327, 1257, 1194, 1155, 1134, 1257, 1194, 1155, 1134, 1078, 1024, 980, 935, 802, 436 $cm^{-1}$ $[\alpha]^{23.7}D$=−9.1° (c=0.35, $CH_2Cl_2$)

$^1$H-NMR: (400 MHz, $CDCl_3$) δ 7.73 (m 1H), 6.82 (qq, J=1.5, 7.1 Hz, 1H), 6.04 (brs, 1H), 5.45 (d, J=9.9 Hz, 1H), 4.24 (s, 1H), 4.08 (app p, J=2.8 Hz, 1H), 3.93 (brs, 1H), 3.87 (d, J=12.3 Hz, 1H), 3.81 (d, J=12.6 Hz, 1H), 3.64 (brs, 1H), 3.28 (s, 1H), 3.19 (d, J=6.6 Hz, 1H), 2.39 (h, J=7.0 Hz, 1H), 1.96 (dq, J=9.9, 6.4 Hz, 1H), 1.82 (t, J=1.3 Hz, 3H), 1.79 (app d, J=7.1 Hz, 3H), 1.76 (dd, J=1.0, 3.0 Hz, 1H), 1.77-1.69 (m, 1H), 1.46 (dp, J=14.3, 7.4 Hz, 1H), 1.29 (d, J=6.6 Hz, 1H), 1.27 (s, 1H), 1.24 (s, 1H), 1.14 (d, J=7.0 Hz, 3H), 0.94 (t, J=7.4 Hz, 3H), 0.86 (d, J=6.5 Hz, 3H)

$^{13}$C-NMR: (101 MHz, $CDCl_3$, 30 peaks total) δ 210.1, 179.1, 167.6, 164.9, 137.7, 133.6, 128.6, 77.3, 76.8, 72.5, 71.6, 65.7, 65.4, 64.7, 61.9, 49.1, 46.1, 41.3, 36.3, 36.2, 26.8, 26.3, 23.8, 17.4, 16.3, 15.2, 14.6, 12.4, 11.8, 9.9

HRMS calculated for $C_{30}H_{42}NaO^+$ $[M+Na]^+$: 585.2670; found: 585.2663

The characterization data of the EBC-46 was identical to the previously reported characterization data of EBC-46 (Paul et al., U.S. Pat. No. 9,770,431).

Example 16

SUW400. Conversion of Acetonide 8 to SI-8 (C12,C13 Saponification and C13 Esterification)

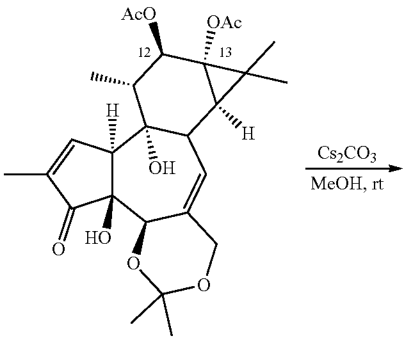

8

-continued

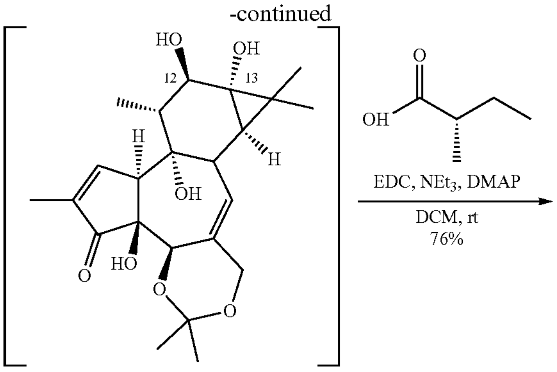

SI-7

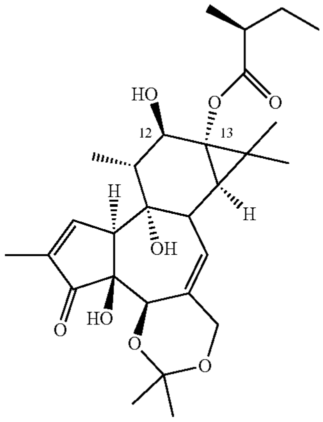

SI-8

Chemicals: (S)-2-methylbutanoic acid (Acros, 98%): used without purification; EDC (Oakwood): used without purification; DMAP (Oakwood): used without purification; Triethylamine (Sigma-Aldrich): distilled from $CaH_2$ prior to use.

To a 2-dram vial equipped with a stir bar was added acetonide 8 (128 mg, 0.253 mmol, 1 equiv). In a separate vial, a solution of cesium carbonate (36.0 mg, 0.110 mmol, 0.436 equiv) was prepared in methanol (2 mL) and sonicated until homogeneous. This basic solution of methanol was added directly to the reaction vessel as a single portion. The reaction mixture was stirred at room temperature for 18 hours. TLC analysis indicated complete conversion to the intermediate SI-7. The reaction was diluted with brine (25 mL) and extracted with EtOAc (5×20 mL) until TLC of the aqueous layer no longer showed product. Quenching with sat. $NH_4Cl$ (normal work-up conditions) led to decomposition of this substrate and was avoided.

The resulting intermediate SI-7 was directly used in the next step. Efforts to purify the diol SI-7 resulted in low yields. As a result, this intermediate was used directly in the subsequent step without chromatographic purification. In a 2-dram vial, EDC (104 mg, 0.544 mmol, 3.15 equiv), triethylamine (79 μL, 0.570 mmol, 3.30 equiv), (S)-2-methylbutanoic acid (52.9 mg, 0.518 mmol, 3.0 equiv), and DMAP (4.2 mg, 0.0345 mmol, 0.2 equiv) were dissolved in DCM (3 mL) and sonicated until homogeneous. In a separate vial, the crude diol SI-7 was dissolved in DCM (1 mL) and the DCM solution of activated acid was added directly in one portion. The reaction was stirred at it for 2 hours. TLC analysis indicated complete conversion to methyl butanoate SI-8. The reaction was quenched with methanol (1 mL) and diluted with brine (25 mL) and 1 M HCl (0.5 mL). The aqueous layer was extracted with DCM (3×10 mL). The combined organic layers were dried over $Na_2SO_4$, filtered, and concentrated. Purification was accomplished by silica gel flash column chromatography (10%-40% EtOAc/Hex, 2×15 cm) affording methyl butanoate SI-8 (48.1 mg, 37% over 2 steps) as a white foam. Compound purity was established by TLC (one spot) analysis.

TLC: Rf=0.48 (50% EtOAc/Hex), UV active, green spot in p-anisaldehyde

FTIR: (ATR) 3399 (br), 2965, 2926, 2878, 1706, 1633, 1460, 1378, 1328, 1263, 1232, 1196, 1159, 1083, 1022, 990, 909, 872 $cm^{-1}$ $[\alpha]^{24.0}D$=+23.4° (c=0.22, $CH_2Cl_2$)

$^1$H-NMR: (400 MHz, $d_6$-acetone) δ 7.61 (m, 1H), 5.41 (d, J=3.5 Hz, 1H), 4.96 (brs, 1H), 4.58 (d, J=12.0 Hz, 1H), 4.43 (s, 1H), 4.24 (s, 1H), 4.21 (d, J=3.9 Hz, 1H), 3.98 (d, J=12.0 Hz, 1H), 3.90 (dd, J=9.5, 4.0 Hz, 1H), 3.51 (m, 1H), 3.00 (app p, J=2.8 Hz, 1H), 2.42 (h, J=7.0 Hz, 1H), 1.87 (dq, J=9.5, 6.5 Hz, 1H), 1.75-1.63 (m, 4H), 1.54-1.42 (m, 4H), 1.33 (s, 3H), 1.24 (s, 6H), 1.14 (d, J=7.0 Hz, 3H), 1.08 (d, J=6.3 Hz, 1H), 1.05 (d, J=6.5 Hz, 3H), 0.92 (t, J=7.4 Hz, 3H).

$^{13}$C-NMR (101 MHz, $d_6$-acetone, 28 peaks total) δ 205.9, 160.3, 136.5, 134.8, 127.6, 100.6, 77.9, 77.8, 74.5, 73.4, 69.2, 69.0, 60.7, 56.1, 47.5, 42.1, 40.8, 36.6, 27.3, 27.0, 24.4, 20.3, 17.6, 16.9, 16.3, 14.6, 12.1, 10.3

HRMS calculated for $C_{23}H_{40}NaO_8^+$ $[M+Na]^+$: 527.2615; found: 527.2619

Example 17

SUW400. Conversion of SI-8 to SUW400 (13) (C12 Esterification and Deprotection)

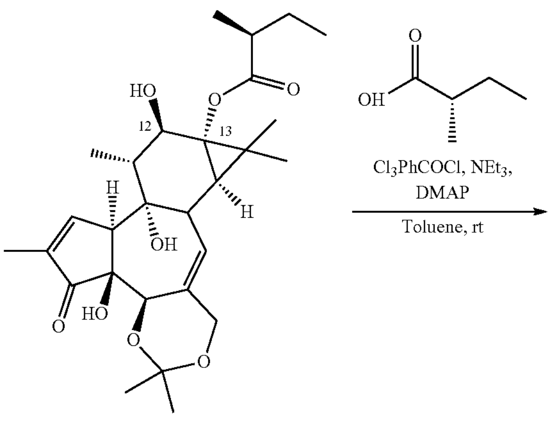

SI-8

-continued

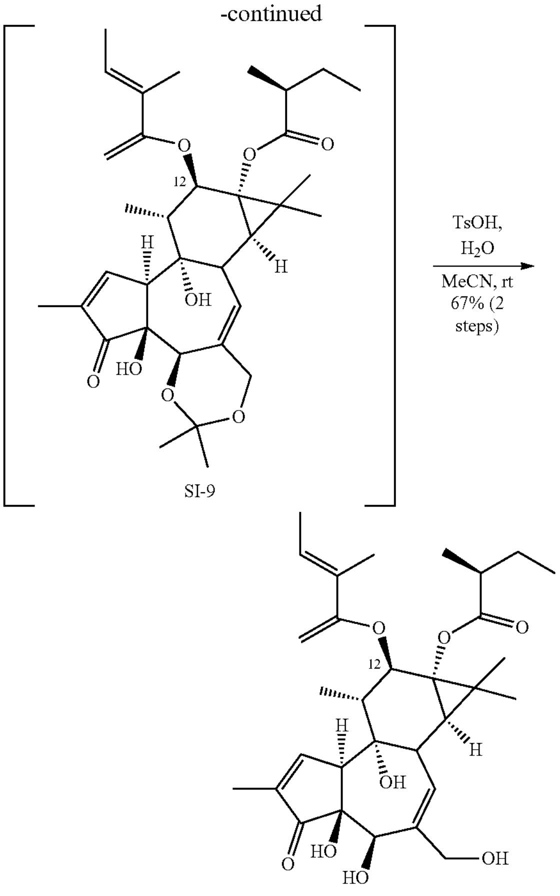

SI-9

13

Chemicals: 2,4,6-trichlorobenzoyl chloride (TCl, >98%): used without purification: Tiglic acid (TCl, >98%): used without purification: DMAP (Oakwood): used without purification: Triethylamine (Sigma-Aldrich): distilled from $CaH_2$ prior to use: Tosic acid monohydrate (Sigma-Aldrich. 98%): used without purification.

To a 2-dram vial was added tiglic acid (5.6 mg, 0.056 mmol, 2.0 equiv) followed by anhydrous toluene (0.5 mL). Triethylamine (16 μL, 0.112 mmol, 4 equiv) was added in one portion followed by 2,4,6-trichlorobenzoyl chloride (8.3 μL, 0.053 mmol, 1.9 equiv). This mixture was stirred vigorously at rt for 2 hours. In a separate vial, methyl butanoate SI-8 (14.1 mg, 0.028 mmol, 1 equiv) was dissolved in anhydrous toluene (0.5 mL). The substrate solution was added to the previously described solution of in situ generated mixed anhydride in one portion followed by addition of DMAP (8.9 mg, 0.073 mmol, 2.6 equiv). The reaction mixture was stirred at rt for 1 hour. TLC analysis indicated complete consumption of methyl butanoate SI-8. The reaction was diluted with sat. $NaHCO_3$ (10 mL) and extracted with EtOAc (3×10 mL). The combined organic layers were dried over $Na_2SO_4$, filtered, and concentrated.

Tiglate SI-9 was used directly in the following step without purification. To a 2-dram vial equipped with a stir bar was added crude tiglate SI-9 and acetonitrile (0.75 mL). In a separate 2-dram vial, tosic acid (3.4 mg, about 1 M) was dissolved in water (0.25 mL). This acidic aqueous solution was added to the solution of the substrate in one portion. The reaction mixture was stirred at rt for 2 hours. TLC analysis indicated complete consumption of tiglate SI-9. The reaction was diluted sat. $NaHCO_3$ (5 mL) and extracted with EtOAc (3×5 mL). The combined organic layers were dried over $Na_2SO_4$, filtered, and concentrated. Purification was accomplished by silica gel flash column chromatography (20%-70% EtOAc/Hex, 3×13 cm) affording SUW400 (13) (10.2 mg, 67% over 2 steps) as a white solid. Compound purity was established by TLC (one spot) analysis. Prior to use in biological studies, a sample of SUW400 was further purified by preparative HPLC. See SI-44 for HPLC purification procedure.

TLC: Rf=0.24 (50% EtOAc/Hex), UV active, green spot in p-anisaldehyde

FTIR: (ATR) 3400 (br), 3357, 2958, 2924, 2858, 1709, 1462, 1379, 1259, 1128, 1084, 1020, 800 $cm^{-1}$ $[\alpha]^{23.0}D=-4.9°$ (c=0.05, $CH_2Cl_2$)

$^1H$-NMR: (400 MHz, $CDCl_3$) δ 7.67 (m, 1H), 6.83 (qq, J=1.3, and 7.0 Hz, 1H), 5.94 (brs, 1H), 5.73 (d, J=4.9 Hz, 1H), 5.45 (d, J=10.1 Hz, 1H), 4.35 (s, 1H), 4.24 (d, J=12.8 Hz, 1H), 4.20 (d, J=12.4 Hz, 1H), 3.79 (brs, 1H), 3.49 (app t, J=5.8 Hz, 1H), 3.02 (app p, J=2.8 Hz, 1H), 2.39 (h, J=7.0 Hz, 1H), 2.10 (dq, J=9.8, 6.6 Hz, 1H), 1.83 (app t, J=1.2 Hz, 1H), 1.80-1.78 (m, 6H), 1.77-1.70 (m, 2H), 1.51-1.42 (m, 1H), 1.26 (s, 3H), 1.22 (s, 3H), 1.14 (d, J=7.0 Hz, 1H), 1.04 (d, J=5.6 Hz, 1H), 0.94 (t, J=7.4 Hz, 3H), 0.93 (d, J=7.5 Hz, 3H)

$^{13}C$-NMR: (101 MHz, $CDCl_3$, 30 peaks total) δ 209.8, 179.4, 167.7, 162.2, 139.9, 137.7, 134.2, 133.2, 128.6, 77.2, 76.9, 73.5, 72.2, 68.1, 65.4, 53.9, 44.5, 41.4, 39.1, 36.8, 26.4, 26.3, 23.9, 17.2, 16.3, 15.1, 14.6, 12.4, 11.8, 10.1

HRMS calculated for $C_{30}H_{41}O_9^+$ $[M-H]^-$: 545.2756; found: 545.2759

Example 18

SUW401. Conversion of α-Epoxide 9 to SUW401 (14) (Acetonide Deprotection)

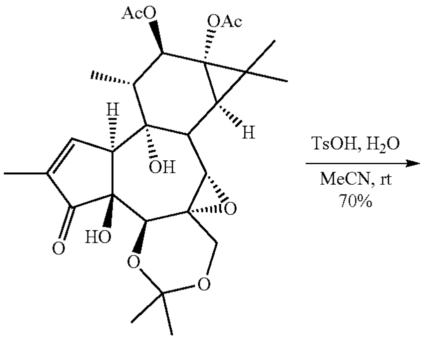

9

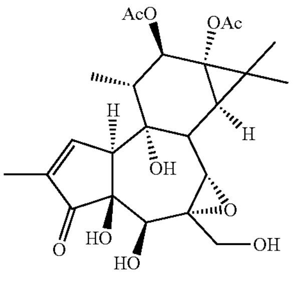

14

Chemicals: Tosic acid monohydrate (Sigma-Aldrich, 98%): used without purification To a 2-dram vial equipped with a stir bar was added α-epoxide 9 (12 mg, 0.023 mmol, 1 equiv) and acetonitrile (0.3 mL). In a separate 2-dram vial, tosic acid (4.6 mg, about 1 M) was dissolved in water (0.1 mL). This acidic aqueous solution was added to the solution of the substrate in one portion. The reaction mixture was stirred at rt for 21 hours. TLC analysis indicated complete consumption of α-epoxide 9. The reaction was diluted sat. $NaHCO_3$ (5 mL) and extracted with EtOAc (3×5 mL). The combined organic layers were dried over $Na_2SO_4$, filtered, and concentrated. Purification was accomplished by silica gel flash column chromatography (20%-70% EtOAc/Hex, 3×13 cm) affording SUW401 (14) (8.0 mg, 70%) as a white solid. Compound purity was established by TLC (one spot) analysis. Prior to use in biological studies, a sample of SUW401 was further purified by preparative HPLC.

TLC: Rf=0.27 (90% EtOAc/Hex), UV active, green spot in p-anisaldehyde

FTIR: (ATR) 3502 (br), 3481 (br), 3399 (br), 1959, 2925, 1717, 1628, 1455, 1375, 1327, 1261, 1242, 1165, 1081, 1021, 980, 921, 736 $cm^{-1}$ $[\alpha]^{22.7}D=+18.4°$ (c=0.38, $CH_2Cl_2$)

$^1H$-NMR: (400 MHz, $CDCl_3$) δ 7.75 (m, 1H), 5.39 (d, J=10.0 Hz, 1H), 4.26 (s, 1H), 4.07 (t, J=2.8 Hz, 1H), 3.91 (d, J=12.5 Hz, 1H), 3.82 (d, J=12.5 Hz, 1H), 3.30 (s, 1H), 3.19 (d, J=6.6 Hz, 1H), 2.13 (m, 4H), 2.10 (s, 3H), 1.96 (m, 1H), 1.80 (dd, J=2.9, 1.3 Hz, 3H), 1.36 (d, J=6.7 Hz, 1H), 1.27 (s, 3H), 1.25 (s, 3H), 0.90 (d, J=6.5 Hz, 3H)

$^{13}C$-NMR: (101 MHz, $CDCl_3$, 24 peaks total) δ 210.0, 173.7, 171.0, 164.6, 133.7, 77.3, 76.8, 72.5, 71.7, 66.0, 65.4, 64.7, 61.9, 49.1, 45.6, 36.1, 35.9, 26.6, 23.8, 21.2 (2C), 17.1, 15.2, 9.9

HRMS calculated for $C_{24}H_{33}O_{10}^+$ $[M+H]^+$: 481.2069; found: 481.2063

Example 19

SUW402. Conversion of SI-1 to SI-10 (C13 Esterification)

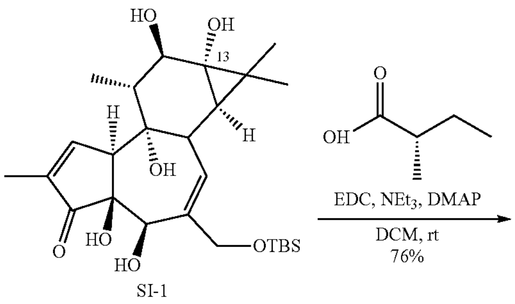

SI-1

-continued

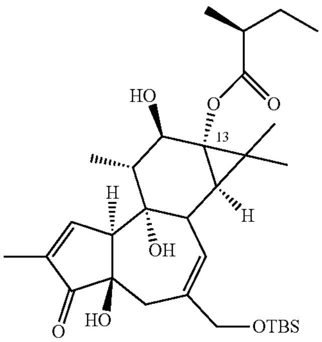

SI-10

Chemicals: (S)-2-methylbutanoic acid (Acros, 98%): used without purification; EDC (Oakwood): used without purification; DMAP (Oakwood): used without purification; Triethylamine (Sigma-Aldrich): distilled from $CaH_2$ prior to use.

To a 2-dram vial equipped with a stir bar was added SI-1 (34 mg, 0.072 mmol, 1 equiv) in 1.0 mL DCM. In a separate vial, EDC (43 mg, 0.23 mmol, 3.15 equiv), triethylamine (33 μL, 0.24 mmol, 3.30 equiv), (S)-2-methylbutanoic acid (22 mg, 0.22 mmol, 3.0 equiv), and DMAP (2.6 mg, 0.022 mmol, 0.2 equiv) were dissolved in DCM (1 mL) and sonicated until homogeneous. The DCM solution of activated acid was added to the substrate in one portion. The reaction was stirred at rt for 2 hours. TLC analysis indicated complete conversion to methyl butanoate SI-10. The reaction was quenched with methanol (1 mL) and diluted with brine (5 mL) and 1 M HCl (0.1 mL). The aqueous layer was extracted with DCM (3×10 mL). The combined organic layers were dried over $Na_2SO_4$, filtered, and concentrated. Purification was accomplished by silica gel flash column chromatography (10%-40% EtOAc/Hex, 3×10 cm) affording methyl butanoate SI-10 (27 mg, 67%) as a white foam. Compound purity was established by TLC (one spot) analysis.

TLC: Rf=0.15 (50% EtOAc/Hex), UV active, green spot in p-anisaldehyde

FTIR: (ATR) 3415 (br), 2957, 2927, 2857, 1710, 1697, 1628, 1462, 1378, 1328, 1256, 1193, 1135, 1084, 836, 776 $cm^{-1}$ $[\alpha]^{23.2}D=+50.5°$ (c=0.17, $CH_2Cl_2$)

$^1$H-NMR: (400 MHz, $CDCl_3$) δ 7.58 (m, 1H), 5.61 (d, J=5.5 Hz, 1H), 4.01 (s, 2H), 3.94 (d, J=9.7 Hz, 1H), 3.16 (m, 2H), 2.54-2.33 (m, 3H), 2.15 (s, 1H), 2.06-1.94 (m, 1H), 1.79 (m, 3H), 1.72 (m, 1H), 1.53-1.41 (m, 2H), 1.27 (s, 3H), 1.22 (s, 3H), 1.17 (d, J=7.3 Hz, 3H), 1.09 (d, J=6.5 Hz, 3H), 1.00 (d, J=5.6 Hz, 1H), 0.94 (t, J=7.4 Hz, 4H), 0.88 (s, 9H), 0.06 (d, J=2.7 Hz, 6H)

$^{13}$C-NMR: (101 MHz, $CDCl_3$) δ 209.2, 179.7, 160.7, 140.7, 133.0, 127.9, 78.3, 77.8, 73.6, 68.1, 67.9, 56.9, 45.0, 41.3, 39.2, 38.5, 35.7, 26.6, 26.1 (3C), 23.9, 18.5, 17.1, 16.6, 15.1, 11.8, 10.2, −5.1 (2C)

HRMS calculated for $C_{31}H_{50}NaO_8^+$ $[M+Na]^+$: 585.3218; found: 585.3219

Example 20

SUW402. Conversion of SI-10 to SUW402 (15) (C12 Esterification and Deprotection)

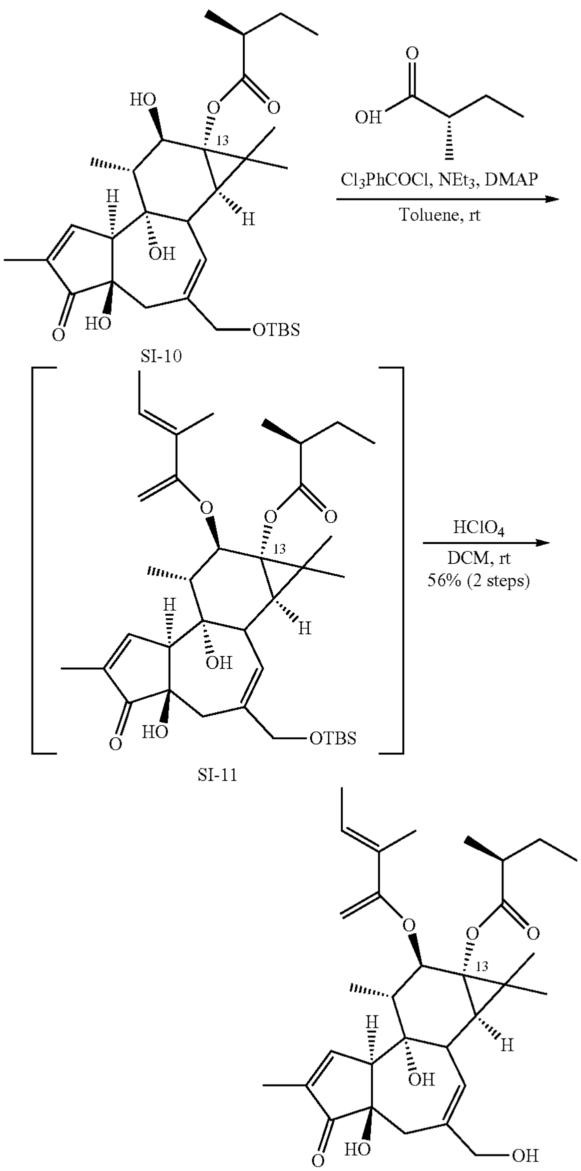

SI-10

SI-11

15

Chemicals: 2,4,6-trichlorobenzoyl chloride (TCl, >98%): used without purification; Tiglic acid (TCl, >98%): used without purification; DMAP (Oakwood): used without purification; Triethylamine (Sigma-Aldrich): distilled from $CaH_2$ prior to use $HClO_4$ (Baker, 70%): used without purification.

To a 2-dram vial was added tiglic acid (10.2 mg, 0.102 mmol, 2.2 equiv) followed by anhydrous toluene (0.5 mL). Triethylamine (26 μL, 0.19 mmol, 4 equiv) was added in one portion followed by 2,4,6-trichlorobenzoyl chloride (15 μL, 0.093 mmol, 2 equiv). This mixture was stirred vigorously at rt for 2 hours. In a separate vial, methyl butanoate SI-10 (26.2 mg, 0.0465 mmol, 1 equiv) was dissolved in anhydrous toluene (0.5 mL). The substrate solution was added to the previously described solution of in situ generated mixed anhydride in one portion followed by addition of DMAP (14.8 mg, 0.121 mmol, 2.6 equiv). The reaction mixture was stirred at rt for 1 hour. TLC analysis indicated complete consumption of methyl butanoate SI-10. The reaction was diluted with sat. $NaHCO_3$ (10 mL) and extracted with DCM (3×10 mL). The combined organic layers were dried over $Na_2SO_4$, filtered, and concentrated affording crude tiglate SI-11.

Tiglate SI-11 was used directly in the following step without purification. To a 2-dram vial equipped with a stir bar was added crude tiglate SI-11 and DCM (1.0 mL). 70% w/w $HClO_4$ (40 μL, 0.47 mmol, 10 equiv) was added to the reaction mixture in one portion. The reaction mixture was stirred at rt for 1 hour. TLC analysis indicated complete consumption of tiglate SI-11. The reaction was quenched with sat. $NaHCO_3$ (10 mL) and extracted with DCM (3×10 mL). The combined organic layers were dried over $Na_2SO_4$, filtered, and concentrated. Purification was accomplished by silica gel flash column chromatography (20%-60% EtOAc/Hex, 3×10 cm) affording SUW402 (15) (13.8 mg, 56% over 2 steps) as a white solid. Compound purity was established by TLC (one spot) analysis. Prior to use in biological studies, a sample of SUW402 was further purified by preparative HPLC.

TLC: Rf=0.34 (50% EtOAc/Hex), UV active, green spot in p-anisaldehyde

FTIR: (ATR) 3399, 2965, 2924, 2879, 1707, 1651, 1460, 1377, 1332, 1259, 1193, 1131, 1072, 1016, 976, 946, 805, 734 $cm^{-1}$ $[\alpha]^{22.7}D=+34.0°$ (c=0.24, $CH_2Cl_2$)

$^1H$-NMR: (400 MHz, $CDCl_3$) δ 7.63 (m, 1H), 6.85 (qq, J=1.4 Hz, 7.1 Hz, 1H), 5.86 (brs, 1H), 5.73 (d, J=5.5 Hz, 1H), 5.50 (d, J=10.2 Hz, 1H), 4.08 (d, J=13.0 Hz, 1H), 4.03 (d, J=12.9 Hz, 1H), 3.32-3.25 (m, 2H), 2.62-2.47 (m, 2H), 2.42 (h, 7.0 Hz, 1H), 2.20 (m, 9H), 1.88 1.84 (m, 3H), 1.84-1.78 (m, 6H), 1.78-1.71 (m, 1H), 1.49 (dq, J=14.0, 7.2 Hz, 1H), 1.31 (s, 3H), 1.24 (s, 3H), 1.16 (d, J=7.0 Hz, 3H), 1.06 (d, J=5.3 Hz, 1H), 0.96 (t, J=7.4 Hz, 3H), 0.91 (d, J=6.5 Hz, 3H)

$^{13}C$-NMR: (101 MHz, $CDCl_3$, 30 peaks total) δ 209.1, 179.3, 167.7, 161.1, 140.4, 137.6, 133.0, 129.5, 128.7, 78.4, 76.9, 73.9, 68.2, 65.5, 56.3, 43.6, 41.4, 39.3, 38.8, 36.8, 26.3, 26.2, 24.0, 17.2, 16.3, 14.6, 14.6, 12.4, 11.8, 10.3.

HRMS calculated for $C_{30}H_{42}NaO_8^+$ $[M+Na]^+$: 553.2772; found: 553.2773

Example 21

PKC Binding Assay Protocol

The protein kinase C (PKC) affinity of EBC-46 and EBC-46 analogs was performed via competition with $^3H$-phorbol-12,13-dibutyrate ($^3H$-PDBu). This procedure entailed a glass-fiber filtration method to determine bound radioligand.

Preparation of PKC binding assay buffer: To a 50 mL polypropylene tube was added Tris-HCl (pH 7.4, 1 M, 1 mL), KCl (1 M, 2 mL), $CaCl_2$ (0.1 M, 30 μL), and bovine serum albumin (BSA, 40 mg, Sigma-Aldrich). This mixture was diluted to 20 mL with deionized $H_2O$ and mixed gently. The buffer was stored on ice until use. The final concentration of these constituents is shown in the following table:

TABLE 3

PKC binding assay buffer composition

| Constituent | Stock Concentration | Quantity | Final Concentration |
|---|---|---|---|
| pH 7.4 Tris-HCl | 1.0M | 1.0 mL | 50 mM |
| KCl | 1.0M | 2.0 mL | 100 mM |
| $CaCl_2$ | 0.10M | 30 μL | 0.15 mM |
| BSA | — | 40 mg | 2 mg/mL |
| Deionized $H_2O$ | — | Final vol of 20 mL | — |

Preparation of phosphatidylserine (PS) vesicles: For every two assays, 3.5 mg phosphatidylserine (Avanti Polar Lipids, porcine, 25 mg/mL $CHCl_3$ solution) was concentrated by removing chloroform under a stream of nitrogen followed by reduced pressure. The solid PS was suspended as vesicles in freshly prepared PKC binding assay buffer (3.5 mL) by sonicating six times for 30 sec, with a 30 sec rest between sonications (VWR 50HT sonicator). The resulting milky cloudy mixture (1 mg/mL) was stored on ice until use.

Preparation of PKC isoform solution: Assay PKC was prepared by dissolving a 4 μg aliquot of the indicated recombinant human PKC isoform (Invitrogen) into 11.6 mL of PKC binding assay buffer (this amount is sufficient for two assays). The diluted PKC was stored on ice for immediate use.

Preparation of $^3H$-PDBu solution: $^3H$-PDBu (American Radiolabeled Chemicals, Inc.; 1 mCi/mL acetone solution; specific activity: 20 Ci/mmol) was diluted 10-fold with DMSO. The resulting 500 nM stock solution was further diluted with DMSO to 30 nM.

Preparation of analog compound dilutions: Compound dilutions were prepared by serially diluting from a chosen "high" concentration by factors of 4. For each analog compound, seven concentrations were used to define the inhibition curve (i.e. for SUW400, the analog concentrations used were 15000 nM, 3750 nM, 937.5 nM, 234.375 nM, 58.6 nM, 14.6 nM, and 3.7 nM).

"Master Mix" solution: To a polypropylene tube was added 3.3 mL of 1 mg/mL PS vesicles solution, 11 mL of PKC isoform solution, and 1.1 mL of 30 nM $^3H$-PDBu solution. The resulting solution was vortexed to mix and stored on ice.

Materials: Glass-fiber filters (Whatman GF/B) were prepared by soaking them in a solution of aqueous polyethyleneimine (10% by vol, 18 mL) in deionized water (600 mL) for at least 1 hour.

500 mL "rinsing buffer" of 20 mM Tris, pH 7.4 was cooled on ice for the duration of the incubation period and for the remainder of the assay.

Example 22

PKC binding assay protocol: Triplicate data points were obtained for each analog concentration. For each data point, 280 μL of "Master Mix" Solution and 20 μL of analog compound at a specified concentration were added to a polypropylene tube. Non-specific $^3H$-PDBu binding was assessed in triplicate by substitution of the analog compound with unlabeled PDBu (20 μL of a 75 μM stock, assay concentration: 5 μM). Maximal $^3H$-PDBu binding was assessed in triplicate by substitution of the analog compound with 20 μL DMSO. The solutions were vortexed to mix, incubated at 37° C. for 10 min, and incubated on ice for at least 30 min prior to filtration. Using a Brandel Harvester, the assay contents from each polypropylene tube were vacuum-filtered through polyethylenimine-soaked filters, washing with rinsing buffer (3×) and drying first under vacuum for 5 min and then under ambient conditions for at least 2 hours. The resulting filters had circular perforations for each data point, which were removed with forceps and placed in a scintillation vial. Scintillation vials were filled with Bio-Safe II scintillation fluid (5 mL) and measured for radioactivity using a Beckman LS 6000SC scintillation counter. Counts per minute (cpm) were averaged for each triplicate dilution. The data were plotted-cpm vs. log(concentration)-using Excel and an IC50 was determined using least squares regression analysis. $K_i$ values were calculated using the equation: K; =150/(1+([$^3$H-PDBu]/$K_d$)). The $K_d$ of $^3$H-PDBu for PKC isoforms was measured separately via saturation binding experiments under identical conditions.

Example 23

PKCβI-GFP Translocation Assay Protocol

Cell culture: Chinese hamster ovary factor K1 (CHO-K1, ATCC) cells were cultured in F-12 Kaighn's media (Hyclone, 10% fetal bovine serum, 1% penicillin/streptomycin added, referred to as F-12+/+ below) at 37° C. in an incubator (5% $CO_2$). Cell cultures were maintained by splitting cells 1:4 when they reached 75-100% confluency (every 2-3 days) as follows:

Media was aspirated (taking care not to disturb adherent cells) and 0.75 mL of TrypLE® Express (Gibco) was added and incubated for 10 minutes in a 37° C. incubator (5% $CO_2$) to remove the cells from a 6-well plate. The cell suspension was quenched with 1 mL of F-12+/+ media and centrifuged for 5 mins at 1000 rpm in a 15 mL Falcon tube. The supernatant was aspirated, and the cells were resuspended in 1 mL of F-12+/+ media. 250 μL of this cell solution was added to 2.25 mL of F-12+/+ media in one well of a 6-well plate. Transfection: Cells were grown to confluency (about 1.2 million cells) in one well of a 6-well plate. F-12+/+ was aspirated and cells were washed with PBS. 2 mL of fresh F-12−/− was then added to each well, taking care not to disturb adherent cells. For each well of CHO-K1 cells, 12.5 μL Lipofectamine 2000 reagent (Invitrogen) was added to 250 μL Opti-MEM reduced serum media (Invitrogen) in a polypropylene tube and incubated for 20 minutes at RT. Meanwhile, for each well, 4 μg of PKCβ-GFP pDNA and 250 μL Opti-MEM reduced serum media was added to a separate polypropylene tube. 250 μL of the Lipofectamine 2000 suspension was added to the DNA suspension and the solution incubated for 30 minutes at RT. 500 μL of the Lipofectamine/DNA suspension was added to the respective wells of the 6-well plate. The cells were then incubated at 37° C. (5% CO2) for about 24 hours.

Plating on chambered coverglass slides: After incubation, the media was aspirated, and cells were washed with PBS (2.0 mL) and trypsinized with TrypLE® Express (750 μL) for 10 minutes in a 37° C. incubator (5% $CO_2$). The cell suspension was then quenched with 1 mL of F-12+/+ media in a 15 mL Falcon tube and centrifuged for 5 minutes at 1000 rpm. The supernatant was removed, and the cell suspension was then diluted with 2.5 mL F-12+/+. 200 μL aliquots were added to 4 wells of a Lab-Tek II 4-well chambered coverglass slide (Fisher). The cell suspension in each well was directly diluted with 600 μL of additional F-12+/+. The resulting samples were incubated for about 24 hours prior to imaging.

Dosing an acquiring data: Fluorescent images were obtained using an Airyscan2 LSM980 inverted confocal microscope. Prior to analysis, media was aspirated and 800 μL of PBS (Hyclone, without Cat or Mgt) supplemented with glucose (10 mM) was added to each well of the chambered coverglass slide. EBC-46 and EBC-46 analogs were diluted to the appropriate concentration in 200 μL of 10 mM glucose in PBS. Cells were located for imaging and data was imaged at 30 second intervals following the addition of compound (set to t=0) for 5.5 mins. Data were recorded at 37° C. and 5% $CO_2$. Images were exported as .czi files and fluorescence intensity was analyzed using FIJI (NIH) software. To monitor the translocation, small cytosolic regions of interest were selected in each cell, and fluorescence intensity values were normalized and plotted vs. time.

Example 24

Computational methodologies and data: Computational methodologies were performed based on the protocols by Hoye et al., (Willoughby et al., *Nat. Protoc.* 9, 3, 643-660 (2014); Willoughby et al., *Nat. Protoc.* 15: 2277 (2020)). Structures of compound 1 were generated using the 2D Sketcher on Schrödinger Maestro and were first subjected to conformational search using Monte Carlo/Molecular Mechanics algorithm on MacroModel (Schrödinger Suite 2016) (Force Field: OPLS_2005; implicit solvent model: $CHCl_3$; convergence threshold: 0.001) with an energy window for conformers generated within 5.02 kcal/mol. Maximum iterations were adjusted to 5000.

Upon completion of a conformer search by molecular mechanics, the lowest energy conformer was further optimized, and their frequency calculations performed, by density functional theory (DFT), using M06-2X$^3$/6−31+G(d,p) and the implicit solvent model IEF-PCM. Visualization of ligand interactions with the C1 domain of protein kinase C-b (PKC) was accomplished on Schrödinger Maestro.

Docking of tigilanol tiglate (1) and analogs to the ligand binding site of PKC-C1 was conducted with Schrödinger Glide. Ligand preparation was conducted using standard parameters on LigPrep (Schrödinger Suite 2016) using the DFT-optimized geometries for each compound (Force Field: OPLS_2005, maximum 32 conformers per ligand). The receptor (PDB:1 PTR) was prepared using standard parameters with the Protein Preparation Wizard (Schrödinger Suite 2016) and residue side chain flexibility was permitted for residues lining the binding pocket (Met239, Ser240, Pro241, Thr242, Leu251, Trp252, Gly253, Leu254, Val255, Gln257). The receptor grid was generated based on the centroid of the cognate ligand (phorbol-13-acetate) with grid box parameters of 15 Å×15 Å×15 Å from the grid center. Docking of 1 to PKC-C1 was performed on Glide (Schrödinger Suite 2016) and the results of the lowest energy binding pose were visualized on Schrödinger Maestro. Docking parameters were benchmarked based on correct prediction of the cognate ligand binding pose reported in the X-ray crystal structure.

TABLE 4

Atomic coordinates for DFT minimized tigilanol tiglate (1)

| Center # | Atomic # | X | Y | Z |
|---|---|---|---|---|
| 1 | 6 | −3.49025 | 0.65004 | −0.08366 |
| 2 | 6 | −2.5266 | 0.342656 | −1.23442 |
| 3 | 6 | −2.80012 | 1.435622 | −2.23729 |

TABLE 4-continued

Atomic coordinates for DFT minimized tigilanol tiglate (1)

| Center # | Atomic # | X | Y | Z |
|---|---|---|---|---|
| 4 | 6 | −3.87405 | 2.194458 | −1.94854 |
| 5 | 6 | −4.43006 | 1.723031 | −0.67478 |
| 6 | 6 | −1.06674 | −0.02539 | −0.87937 |
| 7 | 6 | −1.03842 | −0.94305 | 0.37972 |
| 8 | 6 | −2.08894 | −2.03353 | 0.550672 |
| 9 | 6 | −3.55149 | −1.85729 | 0.639632 |
| 10 | 6 | −4.3167 | −0.56771 | 0.345349 |
| 11 | 6 | 0.349854 | −1.54024 | 0.590196 |
| 12 | 6 | 1.544893 | −0.67908 | 0.281817 |
| 13 | 6 | 1.334279 | 0.674606 | −0.36217 |
| 14 | 6 | −0.12 | 1.167849 | −0.54552 |
| 15 | 6 | 1.232577 | −1.01516 | 1.712174 |
| 16 | 8 | −2.82309 | 1.236226 | 1.020264 |
| 17 | 8 | −5.46472 | 2.079574 | −0.13013 |
| 18 | 6 | −4.50067 | 3.297879 | −2.73648 |
| 19 | 1 | −2.87301 | −0.57855 | −1.71725 |
| 20 | 8 | −0.63457 | −0.69483 | −2.05101 |
| 21 | 6 | −4.32238 | −2.8432 | 1.50304 |
| 22 | 8 | −4.29144 | −2.49433 | 2.872902 |
| 23 | 6 | 0.746982 | 0.058472 | 2.666716 |
| 24 | 6 | 2.140016 | −2.02324 | 2.39522 |
| 25 | 1 | 0.463693 | −2.59729 | 0.355316 |
| 26 | 6 | −0.07118 | 2.28497 | −1.59152 |
| 27 | 8 | 2.747993 | −1.30574 | −0.15444 |
| 28 | 6 | 2.831739 | −1.79328 | −1.39784 |
| 29 | 6 | 4.176047 | −2.42812 | −1.6638 |
| 30 | 8 | 1.91934 | −1.73264 | −2.20077 |
| 31 | 6 | 4.452824 | −3.53423 | −0.63489 |
| 32 | 6 | 3.366644 | −4.60742 | −0.60372 |
| 33 | 1 | −1.23129 | −0.2742 | 1.219611 |
| 34 | 8 | 2.034823 | 1.682661 | 0.388587 |
| 35 | 6 | 3.277659 | 2.018691 | −0.01241 |
| 36 | 6 | 3.948355 | 3.015312 | 0.871516 |
| 37 | 8 | 3.801712 | 1.555132 | −1.0052 |
| 38 | 6 | 3.322537 | 3.453609 | 1.975824 |
| 39 | 6 | 3.835852 | 4.437792 | 2.978458 |
| 40 | 6 | 5.275787 | −1.35942 | −1.65994 |
| 41 | 6 | 5.317412 | 3.418016 | 0.397636 |
| 42 | 8 | −2.94751 | −2.45397 | −0.51017 |
| 43 | 8 | −5.05775 | −0.22567 | 1.511983 |
| 44 | 1 | −2.22347 | 1.516063 | −3.1538 |
| 45 | 1 | −1.71245 | −2.87476 | 1.137434 |
| 46 | 1 | −5.00976 | −0.81344 | −0.47507 |
| 47 | 1 | 1.790988 | 0.621199 | −1.35507 |
| 48 | 1 | −0.46732 | 1.597294 | 0.398688 |
| 49 | 1 | −3.44203 | 1.223878 | 1.766874 |
| 50 | 1 | −5.54381 | 3.060457 | −2.96591 |
| 51 | 1 | −4.50082 | 4.227951 | −2.15998 |
| 52 | 1 | −3.96373 | 3.46474 | −3.67204 |
| 53 | 1 | 0.269787 | −1.04889 | −1.96219 |
| 54 | 1 | −5.35568 | −2.92616 | 1.138184 |
| 55 | 1 | −3.84474 | −3.82124 | 1.405593 |
| 56 | 1 | −4.74607 | −1.64421 | 2.954718 |
| 57 | 1 | 0.231343 | 0.885824 | 2.178655 |
| 58 | 1 | 0.0702 | −0.38016 | 3.408315 |
| 59 | 1 | 1.60637 | 0.481484 | 3.196498 |
| 60 | 1 | 3.074856 | −1.54862 | 2.711342 |
| 61 | 1 | 1.635793 | −2.41392 | 3.284791 |
| 62 | 1 | 2.389824 | −2.86388 | 1.744899 |
| 63 | 1 | 0.055701 | 1.868738 | −2.59621 |
| 64 | 1 | −0.96699 | 2.907322 | −1.57055 |
| 65 | 1 | 0.781834 | 2.939003 | −1.3862 |
| 66 | 1 | 4.094538 | −2.87166 | −2.66151 |
| 67 | 1 | 5.418608 | −3.98671 | −0.88549 |
| 68 | 1 | 4.562174 | −3.07449 | 0.35449 |
| 69 | 1 | 3.604642 | −5.38805 | 0.123261 |
| 70 | 1 | 2.393304 | −4.18485 | −0.32675 |
| 71 | 1 | 3.252035 | −5.07863 | −1.585 |
| 72 | 1 | 2.329804 | 3.05665 | 2.175592 |
| 73 | 1 | 3.856714 | 3.97935 | 3.972828 |
| 74 | 1 | 4.834176 | 4.810137 | 2.749782 |
| 75 | 1 | 3.153817 | 5.292251 | 3.042866 |
| 76 | 1 | 5.074073 | −0.57254 | −2.39047 |
| 77 | 1 | 5.352566 | −0.89205 | −0.67453 |
| 78 | 1 | 6.233914 | −1.82653 | −1.90365 |
| 79 | 1 | 5.263583 | 3.842657 | −0.60889 |
| 80 | 1 | 5.776826 | 4.151077 | 1.059343 |
| 81 | 1 | 5.972394 | 2.543858 | 0.336999 |
| 82 | 1 | −5.67582 | 0.483563 | 1.268572 |

We claim:

1. A method for the synthesis of tigilanol tiglate, precursors, and analogs thereof, the method comprising the steps as shown in the schema shown in FIG. 3 of the disclosure.

2. A method for the synthesis of tigilanol tiglate, the method comprising the steps as shown in the schema shown in FIG. 3 of the disclosure.

3. A method of isolating Phorbol (2) from Croton tiglium seeds, the method comprising the steps of:

(a) pulverizing Croton tiglium seeds;

(b) extracting the pulverized seeds by refluxing with methanol and concentrating the product thereof to an oil;

(c) extracting the oil with a plurality of methanol washes and pooling the methanol washes;

(d) adding cesium carbonate to the methanol washes with prolonged stirring (e) acidifying the product of the preceding step with 6M sulfuric acid to a pH of 5.5;

(f) filtering the acidified product and concentrating the filtrate therefrom under reduced pressure at 30° C.;

(g) saturating the aqueous suspension from step (f) sodium chloride;

(h) washing the aqueous phase with diethyl ether;

(i) extracting the diethyl ether with tetrahydrofuran (THF) and concentrating the THF extract under reduced pressure at 30° C.; drying the THF extract concentrate and purifying by silica gel vacuum column chromatography.

* * * * *